United States Patent
Vo-Dinh et al.

(10) Patent No.: US 12,173,355 B2
(45) Date of Patent: *Dec. 24, 2024

(54) NANO-PLASMONIC MOLECULAR PROBES AND METHODS OF USE

(71) Applicant: Duke University, Durham, NC (US)

(72) Inventors: Tuan Vo-Dinh, Chapel Hill, NC (US); Hsin-Neng Wang, Durham, NC (US); Andrew Fales, Durham, NC (US)

(73) Assignee: Duke University, Durham, NC (US)

( * ) Notice: Subject to any disclaimer, the term of this patent is extended or adjusted under 35 U.S.C. 154(b) by 1215 days.

This patent is subject to a terminal disclaimer.

(21) Appl. No.: 16/809,674

(22) Filed: Mar. 5, 2020

(65) Prior Publication Data

US 2020/0291463 A1    Sep. 17, 2020

Related U.S. Application Data

(63) Continuation of application No. 14/861,353, filed on Sep. 22, 2015, now Pat. No. 10,633,695, which is a continuation of application No. PCT/US2013/059312, filed on Sep. 11, 2013.

(60) Provisional application No. 61/804,346, filed on Mar. 22, 2013.

(51) Int. Cl.
*C12Q 1/68* (2018.01)
*A61K 31/713* (2006.01)
*C12Q 1/6825* (2018.01)

(52) U.S. Cl.
CPC .......... *C12Q 1/6825* (2013.01); *A61K 31/713* (2013.01)

(58) Field of Classification Search
None
See application file for complete search history.

(56) References Cited

U.S. PATENT DOCUMENTS

| | | |
|---|---|---|
| 7,285,835 B2 | 10/2007 | Rizzo et al. |
| 7,699,979 B2 | 4/2010 | Li et al. |
| 7,951,535 B2 | 5/2011 | Vo-Dinh et al. |
| 8,045,152 B2 | 10/2011 | Halas et al. |
| 9,561,292 B1 | 2/2017 | Vo-Dinh et al. |
| 9,987,358 B2 | 6/2018 | Vo-Dinh et al. |

(Continued)

FOREIGN PATENT DOCUMENTS

| | | |
|---|---|---|
| WO | 2007044057 A2 | 4/2007 |
| WO | 2010009106 A1 | 1/2010 |

OTHER PUBLICATIONS

Juzenas, P.; Chen, W.; Sun, Y.-P.; Neto Coelho, M.A.; Generalov, R.; Generalova, N.; Christensen, I. L. Adv. Drug Delivery Rev. 2008, 60, (15), 1600-1614.

(Continued)

*Primary Examiner* — Arthur S Leonard
(74) *Attorney, Agent, or Firm* — NK Patent Law

(57) ABSTRACT

Plasmonics-active nanoprobes are provided for detection of target biomolecules including nucleic acids, proteins, and small molecules. The nucleic acids that can be detected include RNA, DNA, mRNA, microRNA, and small nucleotide polymorphisms (SNPs). The nanoprobes can be used in vito in sensitive detection methods for diagnosis of diseases and disorders including cancer. Multiplexing can be performed using the nanoprobes such that multiple targets can be detected simultaneously in a single sample. The methods of use of the nanoprobes include detection by a visible color change. The nanoprobes can be used in vivo for treatment of undesireable cells in a subject.

20 Claims, 24 Drawing Sheets

Specification includes a Sequence Listing.

(56) References Cited

U.S. PATENT DOCUMENTS

| | | |
|---|---|---|
| 2006/0228725 A1 | 10/2006 | Salafsky |
| 2007/0212695 A1 | 9/2007 | Aivazachvili et al. |
| 2008/0266555 A1 | 10/2008 | Murphy et al. |
| 2009/0017480 A1 | 1/2009 | Porter et al. |
| 2009/0023135 A1 | 1/2009 | Sun et al. |
| 2009/0098540 A1 | 4/2009 | Baeumner et al. |
| 2009/0137418 A1 | 5/2009 | Miller et al. |
| 2009/0303461 A1 | 12/2009 | Sun et al. |
| 2010/0234579 A1 | 9/2010 | Mirkin et al. |
| 2010/0254911 A1 | 10/2010 | Sharma et al. |
| 2011/0052671 A1 | 3/2011 | Zasadzinski et al. |
| 2011/0269148 A1 | 11/2011 | Huang et al. |
| 2012/0168671 A1 | 7/2012 | Wang et al. |
| 2012/0225457 A1 | 9/2012 | Lee et al. |

OTHER PUBLICATIONS

Kennedy, L. C.; Bickford, L. R.; Lewinski, N. A.; Coughlin, A. J.; Hu, Y.; Day, E. S.; West, J. L.; Drezek, R. A. Small 2011, 7, (2), 169-183.
Ruoslahti, E.; Bhatia, S. N.; Sailor, M. J. J. Cell Biol. 2010, 188, (6), 759-768.
Peer, D.; Karp, J. M.; Hong, S.; Farokhzad, O. C.; Margalit, R.; Langer, R. Nat. Nanotechnol. 2007, 2, (12), 751-760.
Hu, M.; Chen, J.; Li, Z.-Y.; Au, L.; Hartland, G. V.; Li, X.; Marquez, M.; Xia, Y. Chem. Soc. Rev. 2006, 35, (11), 1084-1094.
Boisselier, E.; Astruc, D. Chem. Soc. Rev. 2009, 38, (6), 1759-1782.
Weissleder, R. Nat. Biotechnol. 2001, 19, (4), 316-317.
Guerrero-Martínez, A.; Barbosa, S.; Pastoriza-Santos, I.; Liz-Marzán, L. M. Curr. Opin. Colloid Interface Sci. 2011, 16, (2), 118-127.
Yuan, H.; Khoury, C. G.; (Co-First Author); Hwang, H.; Wilson, C. M.; Grant, G. A.; Vo-Dinh, T. Nanotechnology 2012, 23, (7), 075102.
Austin, L. A.; Kang, B.; Yen, C.-W.; El-Sayed, M. A. J. Am. Chem. Soc. 2011, 133, (44), 17594-17597.
Tkachenko, A. G.; Xie, H.; Liu, Y.; Coleman, D.; Ryan, J.; Glomm, W. R.; Shipton, M. K.; Franzen, S.; Feldheim, D. L. Bioconjugate Chem. 2004, 15, (3), 482-490.
Tong, L.; Wei, Q.; Wei, A.; Cheng, J.-X. Photochem. Photobiol. 2009, 85, (1), 21-32.
Hutter, E.; Maysinger, D. Microsc. Res. Tech. 2010, 74, (7), 592-604.
Van De Broek, B.; Devoogdt, N.; D'Hollander, A.; Gijs, H.-L.; Jans, K.; Lagae, L.; Muyldermans, S.; Maes, G.; Borghs, G. ACS Nano 2011, 5, (6), 4319-4328.
Huang, X.; Kang, B.; Qian, W.; Mackey, M. A.; Chen, P. C.; Oyelere, A. K.; El-Sayed, I. H.; El-Sayed, M. A. J. Biomed. Opt. 2010, 15, (5), 058002.
Au, L.; Zheng, D.; Zhou, F.; Li, Z.- Y.; Li, X.; Xia, Y. ACS Nano 2008, 2, (8), 1645-1652.
Kim, J.; Park, S.; Lee, J. E.; Jin, S. M.; Lee, J. H.; Lee, I. S .; Yang, I.; Kim, J.-S.; Kim, S. K.; Cho, M.-H.; Hyeon, T. Angew. Chem., Int. Ed. Engl. 2006, 45, (46), 7754-7758.
Patel, L.; Zaro, J.; Shen, W.-C. Pharm. Res. 2007, 24, 1977-1992.
Khalil, I. A.; Kogure, K.; Akita, H.; Harashima, H. Pharmacol. Rev. 2006, 58, (1), 32-45.
Lévy, R.; Shaheen, U.; Cesbron, Y. Nano Rev. 2010, 1, 4889.
Lundqvist, M.; Stigler, J.; Elia, G.; Lynch, I.; Cedervall, T.; Dawson, K. A. Proc. Natl. Acad. Sci. U. S. A. 2008, 105, (38), 14265-14270.
Torchilin, V. P. Adv. Drug Delivery Rev. 2008, 60, (4-5), 548-558.
Wei, Y.; Jana, N. R.; Tan, S. J.; Ying, J. Y. Bioconjugate Chem. 2009, 20, (9), 1752-1758.
Zhao, M.; Kircher, M. F.; Josephson, L.; Weissleder, R. Bioconjugate Chem. 2002, 13, (4), 840-844.
Rao, K. S.; Reddy, M. K.; Horning, J. L.; Labhasetwar, V. Biomaterials 2008, 29, (33), 4429-4438.
Tian, X.-H.; Wei, F.; Wang, T.-X.; Wang, D.; Wang, J.; Lin, X.-N.; Wang, P.; Ren, L. Mater. Lett. 2012, 68.
Wadia, J. S.; Stan, R. V.; Dowdy, S. F. Nat. Med. 2004, 10, (3), 310-315.
Ruan, G.; Agrawal, A.; Marcus, A. I.; Nie, S. J. Am. Chem. Soc. 2007, 129, (47), 14759-14766.
Pallaoro, A.; Braun, G. B.; Moskovits, M. Proc. Natl. Acad. Sci. U. S. A. 2011, 108, (40), 16559-16564.
Lewin, M.; Carlesso, N.; Tung, C. H.; Tang, X. W.; Cory, D.; Scadden, D. T.; Weissleder, R. Nat. Biotechnol. 2000, 18, (4), 410-414.
Krpetic, Z.; Saleemi, S.; Prior, I. A.; See, V.; Qureshi, R.; Brust, M. ACS Nano 2011, 5, (6), 5195-5201.
Berry, C. C.; De La Fuente, J. M.; Mullin, M.; Chu, S. W. L.; Curtis, A. S. G. IEEE Trans. Nanobioscience 2007, 6, (4), 262-269.
Durr, N. J.; Weisspfennig, C. T.; Holfeld, B. A.; Ben-Yakar, A. J. Biomed. Opt. 2011, 16, (2), 026008.
Pan, L.; He, Q.; Liu, J .; Chen, Y.; Ma, M.; Zhang, L.; Shi, J. J. Am. Chem. Soc. 2012, 120320133341008.
Panté, N.; Kann, M. Mol. Biol. Cell 2002, 13, (2), 425-434.
Mishra, A.; Lai, G. H.; Schmidt, N. W.; Sun, V. Z.; Rodriguez, A. R.; Tong, R.; Tang, L.; Cheng, J.; Deming, T. J.; Kamei, D. T.; Wong, G. C. L. Proc. Natl. Acad. Sci. U. S. A. 2011, 108, (41), 16883-16888.
Zhang, L. W.; Monteiro-Riviere, N. A. Toxicol. Sci. 2009, 110, (1), 138-155.
Iversen, T.-G.; Skotland, T.; Sandvig, K. Nano Today 2011, 6, (2), 176-185.
Chen S, Wang ZL, Ballato J, Foulger SH, Carroll DL. J Am Chem Soc. Dec. 31, 2003;125(52):16186-7.
Hao F, Nehl CL, Hafner JH, Nordlander P. Nano Lett. Mar. 2007;7(3):729-32.
Senthil Kumar P, Pastoriza-Santos I, Rodríguez-González B, Garcia De Abajo FJ, Liz-Marzán LM. Nanotechnology. 2008; 19(1):015606-12.
Steel, A. B.; Herne, T. M.; Tarlov, M. J. Anal. Chem. 1998, 70, 4670-7.
Herne, T. M.; Tarlov, M. J. J. Am. Chem. Soc. 1997, 119, 8916-20.
Burgess, J. D.; Hawkridge, F. M. Langmuir 1997, 13, 3781-6.
Boncheva, M.; Scheibler, L.; Lincoln, P.; Vogel, H.; Akerman, B. Langmuir 1999, 15, 4317-20.
Potyrailo RA, Conrad RC, Ellington AD, Hieftje GM. Anal Chem. American Chemical Society; Aug. 1998;70(16):3419-25.
Hainfeld et al., The British Journal of Radiology, 79, 248, 2006.
USPTO; Non-Final Office Action for U.S. Appl. No. 15/785,615 dated Nov. 18, 2019, 10 pages.
USPTO; Non-Final Office Action for U.S. Appl. No. 15/785,615 dated Feb. 8, 2019, 18 pages.
USPTO; Final Office Action for U.S. Appl. No. 15/785,615 dated Jun. 27, 2019, 20 pages.
USPTO; Non-Final Office Action for U.S. Appl. No. 13/888,226 dated Jan. 12, 2017.
USPTO; Non-Final Office Action for U.S. Appl. No. 13/888,226 dated Jan. 11, 2016.
USPTO; Final Office Action for U.S. Appl. No. 13/888,226 dated Jun. 28, 2016.
USPTO; Non-Final Office Action for U.S. Appl. No. 15/408,563 dated Sep. 8, 2017.
USPTO; Non-Final Office Action for U.S. Appl. No. 13/971,822 dated Jun. 15, 2016.
USPTO; Non-Final Office Action for U.S. Appl. No. 15/442,731 dated Jul. 28, 2017.
USPTO; Final Office Action for U.S. Appl. No. 15/442,731 dated Sep. 18, 2018.
USPTO; Final Office Action for U.S. Appl. No. 15/442,731 dated Jun. 15, 2018.
USPTO; Non-Final Office Action for U.S. Appl. No. 14/024,565 dated Jan. 20, 2016.
USPTO; Final Office Action for U.S. Appl. No. 14/024,565 dated Oct. 26, 2016.
WIPO; International Preliminary Report on Patentability for International Patent Application No. PCT/US2013/059312 dated Sep. 22, 2015, 12 pages.

(56) References Cited

OTHER PUBLICATIONS

ISA/KR; International Search Report and Written Opinion for International Patent Application No. PCT/US2013/059312 dated Dec. 5, 2013, 16 pages.
USPTO; Non-Final Office Action for U.S. Appl. No. 14/861,353 dated May 30, 2019.
USPTO; Non-Final Office Action for U.S. Appl. No. 14/861,353 dated Dec. 21, 2017.
USPTO; Non-Final Office Action for U.S. Appl. No. 14/861,353 dated Sep. 1, 2016.
USPTO; Final Office Action for U.S. Appl. No. 14/861,353 dated Jul. 24, 2018.
USPTO; Final Office Action for U.S. Appl. No. 14/861,353 dated Apr. 18, 2017.
Arosio, Daniela, et al., "Cyclic RGD Functionalized Gold Nanoparticles for Tumor Targeting", Bioconjugate Chemistry, ACS Publications, 2011, vol. 22, pp. 664-672.
"Viruses" (Wikipedia.com; accessed Nov. 24, 2012).
"How many species of bacteria are there" (wisegeek.com; accessed Jan. 21, 2014).
"Fungi" (Wikipedia.com; accessed Jun. 3, 2013).
"Plant" (Wikipedia.com; accessed Aug. 28, 2015).
"Mammal" (Wikipedia.com; accessed Sep. 22, 2011).
"Murinae" (Wikipedia.com; accessed Mar. 18, 2013).
"Fish" (Wikipedia.com; accessed Nov. 2, 2014).
"List of sequenced bacterial genomes" (Wikipedia.com; accessed Jan. 24, 2014).
"List of infectious diseases" (Wikipedia.com, accessed Sep. 13, 2018).
Wabuyele et al., Plasmonics nanoprobes: detection of single-nucleotide polymorphisms in the breast cancer BRCA1 gene. Anal Bioanal Chem (2010), vol. 398, pp. 729-736.
Whitcombe, et al., Detection of PCR products using selfprobing amplicons and fluorescence. Nat. Biotechnol, 1999, vol. 17, pp. 804-807.
Wang, et al., "Multiplex detection of breast cancer biomarkers using plasmonic molecular sentinel nanoprobes", Nanotechnology, 2009.
Buzdin, et al., "Stem-Loop Oligonucleotides as Hybridization Probes and Their Practical Use in Molecular Biology and Biomedicine", Nucleic Acids Hybridization Modern Applications, Spring Press, Chapter 4, 2007, pp. 85-96.
Hrelescu et al.: "Single gold nanostars enhance Raman scattering", 2009, Appl. Phys. Lett. 94: 153113, 3 pages.
Dondapati et al.: Label-free biosensing based on single gold nanostarts as plasmonic transducers:, 2010, ACS Nano 4: 6318-6322.
Schütz et al.: "Hydrophilically stabilized gold nanostars as SERS labels for tissue imaging of the tumor suppressor p63 by immuno-SERS microscopy", 2011, Chem. Commun. 47: 4216-4218, Published online Feb. 28, 2011.
Alric et al.: "Gadolinium chelate coated gold nanoparticles as contrast agents for both X-ray computed tomography and magnetic resonance imaging", 2008, J. Am. Chem. Soc. 130: 5908-5915.
Jang et al.: "Gold nanorod-photosensitizer complex for near-infrared fluorescence imaging and photodynamic/photothermal therapy in vivo", 2011, ACS Nano 5: 1086-1094, Published online Jan. 18, 2011.
Rodriguez-Lorenzo et al.: "Plasmonic nanosensors with inverse sensitivity by means of enzyme-guided crystal growth". Nature Materials, May 27, 2012, vol. 11, No. 7, pp. 604-607.
Kievit, F. M.; Zhang, M. Adv. Mater. (Weinheim, Ger.) 2011, 23, (36), H217-47.
Shi, J.; Votruba, A. R.; Farokhzad, O. C.; Langer, R. Nano Lett. 2010, 10, (9), 3223-3230.
Farrell, D.; Alper, J.; Ptak, K.; Panaro, N. J.; Grodzinski, P.; Barker, A. D. Acs Nano 2010, 4, (2), 589-594.
Chadwick, S.; Kriegel, C.; Amiji, M. Adv. Drug Delivery Rev. 2010, 62, (4-5), 394-407.
Riehemann, K.; Schneider, S. W.; Luger, T. A.; Godin, B.; Ferrari, M.; Fuchs, H. Angew. Chem., Int. Ed. Engl. 2009, 48, (5), 872-897.
Wang, X.; Yang, L.; Chen, Z. G.; Shin, D. M. CA Cancer J Clin 2008, 58, (2), 97-110.
Nie, S.; Xing, Y.; Kim, G. J.; Simons, J. W. Annu. Rev. Biomed. Eng. 2007, 9, 257-288.
Hahn, M. A.; Singh, A. K.; Sharma, P.; Brown, S. C.; Moudgil, B. M. Anal. Bioanal. Chem. 2011, 399, (1), 3-27.
Ghosh, P.; Han, G.; De, M.; Kim, C. K.; Rotello, V. M. Adv. Drug Delivery Rev. 2008, 60, (11), 1307-1315.
Huang, L.; Liu, Y. Annu. Rev. Biomed. Eng. 2011, 13, (1), 507-530.
James F Hainfeld, Daniel N Slatkin and Henry M Smilowitz, The use of gold nanoparticles to enhance radiotherapy in mice, Phys. Med. Biol. 49, 2004.
Sang Hyun Cho, Estimation of tumour dose enhancement due to gold nanoparticles during typical radiation treatments: a preliminary Monte Carlo study, Phys. Med. Biol. 50, 2005.
Minelli, C.; Lowe, S. B.; Stevens, M. M., Engineering Nanocomposite Materials for Cancer Therapy, Small 2010, 6, (21), 2336-2357.
Janib, S. M.; Moses, A. S.; Mackay, J. A. Imaging and drug delivery using theranostic nanoparticles, Adv. Drug Deliver. Rev. 2010, 62, (11), 1052-1063.
Lammers, T.; Kiessling, F.; Hennink, W. E.; Storm, G., Nanotheranostics and Image-Guided Drug Delivery: Current Concepts and Future Directions, Mol. Pharm. 2010, 7, (6), 1899-1912.
Kie, J.; Lee, S.; Chen, X., Nanoparticle-based theranostic agents, Adv. Drug Deliver. Rev. 2010, 62, (11), 1064-1079.
Mura, S.; Couvreur, P., Nanotheranostics for personalized medicine, Adv Drug Deliv Rev 2012, 64, (13), 1394-416.
Vo-Dinh, T.; Hiromoto, M. Y. K.; Begun, G. M.; Moody, R. L., Surface-enhanced Raman spectrometry for trace organic analysis, Anal. Chem. 1984, 56, (9), 1667-1670.
Vo-Dinh, T.; Meier, M.; Wokaun, A., Surface-enhanced Raman spectrometry with silver particles on stochastic- post substrates, Anal. Chim. Acta. 1986, 181, (0), 139-148.
Vo-Dinh, T., Surface-enhanced Raman spectroscopy using metallic nanostructures. Trends Analyt. Chem, 1998, 17, (8-9), 557-582.
Vo-Dinh, T.; Dhawan, A.; Norton, S. J.; Khoury, C. G.; Wang, H.-N.; Misra, V.; Gerhold, M.D., Plasmonic Nanoparticles and Nanowires: Design, Fabrication and Application in Sensingt, J. Phys. Chem. C 2010, 114, (16), 7480-7488.
Fales, A. M.; Yuan, H.; Vo-Dinh, T. Silica-Coated Gold Nanostars for Combined Surface-Enhanced Raman Scattering (SERS) Detection and Singlet-Oxygen Generation: A Potential Nanoplatform for Theranostics. Langmuir 2011, 27, (19), 12186-12190.
Yuan, H.; Fales, A. M.; Vo-Dinh, T. TAT Peptide-Functionalized Gold Nanostars: Enhanced Intracellular Delivery and Efficient NIR Photothermal Therapy Using Ultralow Irradiance. J. Am. Chem. Soc. 2012, 134, (28), 11358-11361.
Yuan, H.; Khoury, C. G.; Wilson, C. M.; Grant, G. A.; Bennett, A. J.; Vo-Dinh, T. In vivo particle tracking and photothermal ablation using plasmon-resonant gold nanostars. Nanomedicine 2012, 8, (8), 1355-63.
Bálint, Š.; Rao, S.; Marro, M.; Miškovský, P.; Petrov, D. Monitoring of local pH in photodynamic therapy-treated live cancer cells using surface-enhanced Raman scattering probes. J. Raman Spectrosc. 2011, 42, (6), 1215-1221.
Kircher, M. F.; De La Zerda, A.; Jokerst, J. V.; Zavaleta, C. L.; Kempen, P. J.; Mittra, E.; Pitter, K.; Huang, R.; Campos, C.; Habte, F.; Sinclair, R.; Brennan, C. W.; Mellinghoff, I. K.; Holland, E. C.; Gambhir, S. S. A brain tumor molecular imaging strategy using a new triple-modality MRI-photoacoustic-Raman hanoparticle. Nat Med 2012, 18, (5), 829-834.
Alvarez-Puebla, R. A.; Liz-Marzan, L. M. SERS-Based Diagnosis and Biodetection. Small 2010, 6, (5), 604-610.
Kneipp, J.; Kneipp, H.; Wittig, B.; Kneipp, K. Following the Dynamics of pH in Endosomes of Live Cells with SERS Nanosensorst. J. Phys. Chem. C 2010, 114, (16), 7421-7426.
Kneipp, J.; Kneipp, H.; Rice, W. L.; Kneipp, K. Optical Probes for Biological Applications Based on Surface-Enhanced Raman Scattering from Indocyanine Green on Gold Nanoparticles. Anal. Chem. 2005, 77, (8), 2381-2385.
Kneipp, J.; Kneipp, H.; Rajadurai, A.; Redmond, R. W.; Kneipp, K. Optical probing and imaging of live cells using SERS labels. J. Raman Spectrosc. 2009, 40, (1), 1-5.

(56) References Cited

OTHER PUBLICATIONS

Qian, X. M.; Nie, S. M. Single-molecule and single-nanoparticle SERS: from fundamental mechanisms to biomedical applications. Chem. Soc. Rev. 2008, 37, (5), 912-920.

Faulds, K.; Smith, W. E.; Graham, D. Evaluation of Surface-Enhanced Resonance Raman Scattering for Quantitative DNA Analysis. Anal. Chem. 2003, 76, (2), 412-417.

Rodriguez-Lorenzo, L.; Krpetic, Z.; Barbosa, S.; Alvarez-Puebla, R. A.; Liz-Marzan, L. M.; Prior, I. A.; Brust, M. Intracellular mapping with SERS-encoded gold nanostars. Integr. Biol. 2011, 3, (9), 922-926.

Küstner, B.; Gellner, M.; Schutz, M.; Schoppler, F.; Marx, A.; Strobel, P.; Adam, P.; Schmuck, C.; Schlucker, S. Sers Labels for Red Laser Excitation: Silica-Encapsulated SAMs on Tunable Gold/Silver Nanoshells. Angew. Chem. Int. Edit. 2009, 48, (11), 1950-1953.

Cao, Y. C.; Jin, R.; Nam, J.-M.; Thaxton, C. S.; Mirkin, C. A. Raman Dye-Labeled Nanoparticle Probes for Proteins. J. Am. Chem. Soc. 2003, 125, (48), 14676-14677.

Wang, G.; Park, H.-Y.; Lipert, R.J.; Porter, M. D. Mixed Monolayers on Gold Nanoparticle Labels for Multiplexed Surface-Enhanced Raman Scattering Based Immunoassays. Anal. Chem. 2009, 81, (23), 9643-9650.

Gregas, M. K.; Yan, F.; Scaffidi, J.; Wang, H.-N.; Vo-Dinh, T. Characterization of nanoprobe uptake in single cells: spatial and temporal tracking via SERS labeling and modulation of surface charge. Nanomedicine: NBM 2011, 7, (1), 115-122.

Gregas, M. K.; Scaffidi, J. P.; Lauly, B.; Vo-Dinh, T. Surface-Enhanced Raman Scattering Detection and Tracking of Nanoprobes: Enhanced Uptake and Nuclear Targeting in Single Cells. Appl. Spectrosc. 2010, 64, (8), 858-866.

Zavaleta, C. L.; Smith, B. R.; Walton, I.; Doering, W.; Davis, G.; Shojaei, B.; Natan, M. J.; Gambhir, S. S. Multiplexed imaging of surface enhanced Raman scattering nanotags in living mice using noninvasive Raman spectroscopy. Proc. Natl. Acad. Sci. U S A 2009, 106, (32), 13511-13516.

Keren, S.; Zavaleta, C.; Cheng, Z.; De La Zerda, A.; Gheysens, O.; Gambhir, S. S. Noninvasive molecular imaging of small living subjects using Raman spectroscopy. Proc. Natl. Acad. Sci. U S A 2008, 105, (15), 5844-5849.

Kim, J.-H.; Kim, J.-S.; Choi, H.; Lee, S.-M.; Jun, B.-H.; Yu, K.-N.; Kuk, E.; Kim, Y.-K.; Jeong, D.H.; Cho, M.-H.; Lee, Y. S. Nanoparticle Probes with Surface Enhanced Raman Spectroscopic Tags for Cellular Cancer Targeting. Anal. Chem. 2006, 78, (19), 6967-6973.

Lam, M.; Oleinick, N. L.; Nieminen, A.-L. Photodynamic Therapy-induced Apoptosis in Epidermoid Carcinoma Cells. J. Biol. Chem. 2001, 276, (50), 47379-47386.

Tang, W.; Xu, H.; Kopelman, R.; Philbert, M. A. Photodynamic Characterization and In Vitro Application of Methylene Blue-containing Nanoparticle Platforms. Photochem. Photobiol. 2005, 81, (2), 242-249.

Rossi, L. M.; Silva, P. R.; Vono, L. L. R.; Fernandes, A. U.; Tada, D. B.; Baptista, M. C. S. Protoporphyrin X Nanoparticle Carrier: Preparation, Optical Properties, and Singlet Oxygen Generation. Langmuir 2008, 24, (21), 12534-12538.

Lee, S. J.; Koo, H.; Lee, D.-E.; Min, S.; Lee, S.; Chen, X.; Choi, Y.; Leary, J. F.; Park, K.; Jeong, S. Y.; Kwon, I. C.; Kim, K.; Choi, K. Tumor-homing photosensitizer-conjugated glycol chitosan nanoparticles for synchronous photodynamic imaging and therapy based on cellular on/off system. Biomaterials 2011, 32, (16), 4021-4029.

Bechet, D.; Couleaud, P.; Frochot, C.; Viriot, M.-L.; Guillemin, F.; Barberi-Heyob, M. Nanoparticles as vehicles for delivery of photodynamic therapy agents. Trends Biotechnol. 2008, 26, (11), 612-621.

Roy, I.; Ohulchanskyy, T. Y.; Pudavar, H. E.; Bergey, E. J.; Oseroff, A. R.; Morgan, J.; Dougherty, T. J.; Prasad, P. N. Ceramic-Based Nanoparticles Entrapping Water-Insoluble Photosensitizing Anticancer Drugs: A Novel Drug-Carrier System for Photodynamic Therapy. J. Am. Chem. Soc. 2003, 125, (26), 7860-7865.

Ohulchanskyy, T. Y.; Roy, I.; Goswami, L. N.; Chen, Y.; Bergey, E. J.; Pandey, R. K.; Oseroff, A. R.; Prasad, P. N. Organically Modified Silica Nanoparticles with Covalently Incorporated Photosensitizer for Photodynamic Therapy of Cancer. Nano Lett. 2007, 7, (9), 2835-2842.

Kim, S.; Ohulchanskyy, T. Y.; Pudavar, H. E.; Pandey, R. K.; Prasad, P. N. Organically Modified Silica Nanoparticles Co-encapsulating Photosensitizing Drug and Aggregation-Enhanced Two-Photon Absorbing Fluorescent Dye Aggregates for Two-Photon Photodynamic Therapy. J. Am. Chem. Soc. 2007, 129, (9), 2669-2675.

Yan, F.; Kopelman, R. The Embedding of Meta-tetra(Hydroxyphenyl)-Chlorin into Silica Nanoparticle Platforms for Photodynamic Therapy and Their Singlet Oxygen Production and pH-dependent Optical Properties. Photochem. Photobiol. 2003, 78, (6), 587-591.

Lu, J.; Liong, M.; Zink, J. I.; Tamanoi, F. Mesoporous Silica Nanoparticles as a Delivery System for Hydrophobic Anticancer Drugs. Small 2007, 3, (8), 1341-1346.

Yuan, H.; Fales, A. M.; Khoury, C. G.; Liu, J.; Vo-Dinh, T., J. Raman Spectrosc. 2012., 44 (2) 234-239.

Fernández-López, C.; Mateo-Mateo, C.; Álvarez-Puebla, R. N. A.; Pérez-Juste, J.; Pastoriza-Santos, I.; Liz-Marzán, L. M. Highly Controlled Silica Coating of PEG-Capped Metal Nanoparticles and Preparation of SERS-Encoded Particlest. Langmuir 2009, 25, (24), 13894-13899.

USPTO; Final Office Action for U.S. Appl. No. 15/785,615 dated May 29, 2020, 10 pages.

Santos-Cuevas, Clara L., "Design, preparation, in vitro and in vivo evaluation of 99mTc-N2S2-Tat(49-57)-pombesin: A target-specific hybrid radiopharmaceutical", Elsevier: International Journal of Pharmaceutics, 375, (2009), 75-83.

USPTO; Non-Final Office Action for U.S. Appl. No. 15/785,615 dated May 27, 2021, 15 pages.

ANSI: "American National Standard for Safe Use of Lasers", Laser Institute of America, Orlando, FL, Z136.Jan. 2007, Revision of ANSI Z136.Jan. 2000, approved Mar. 16, 2007, pp. 1-5, pp. 80-81, pp. 246-249, 22 pages total.

Bartczak, D. et al.: "Interactions of Human Endothelial Cells with Gold Nanoparticles of Different Morphologies", Small 2012, 8, No. 1, pp. 122-130, published online: Nov. 18, 2011, 9 pages total.

USPTO: Non-final Office Action for co-pending U.S. Appl. No. 17/712,479, mailed Aug. 15, 2024, 41 pages.

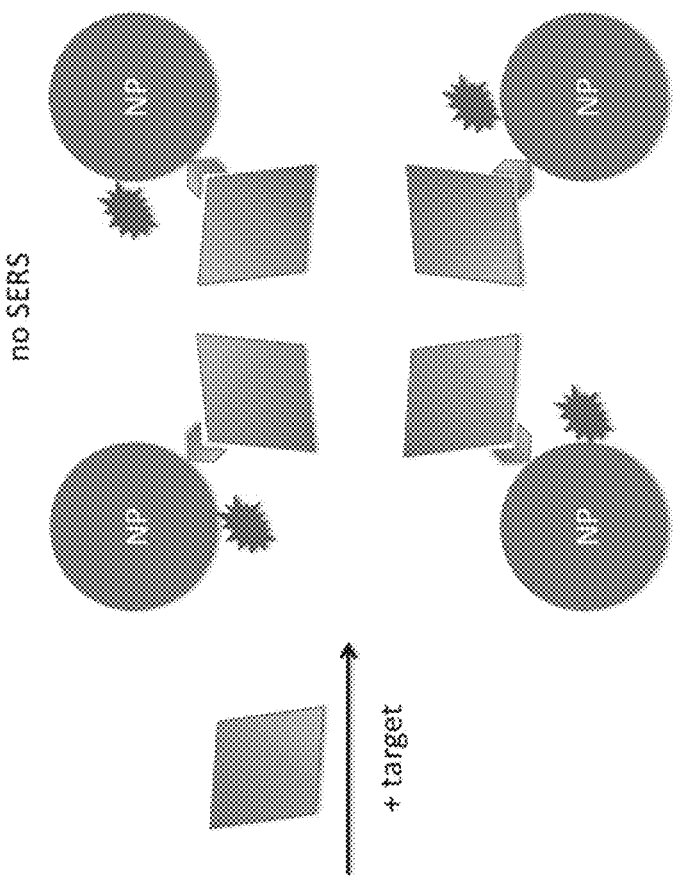
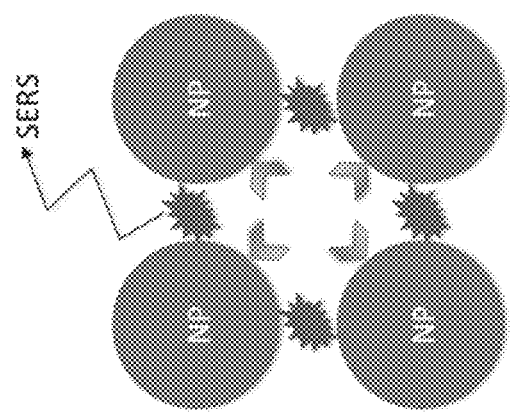
FIG. 9

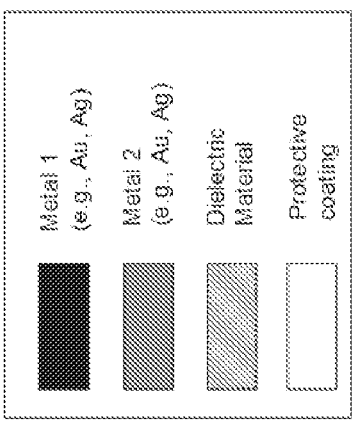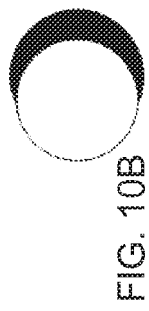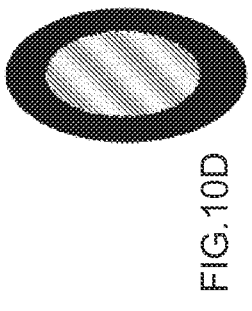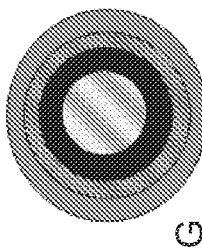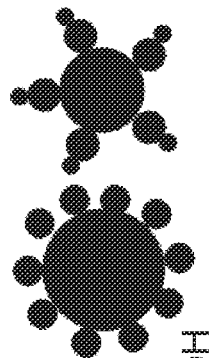

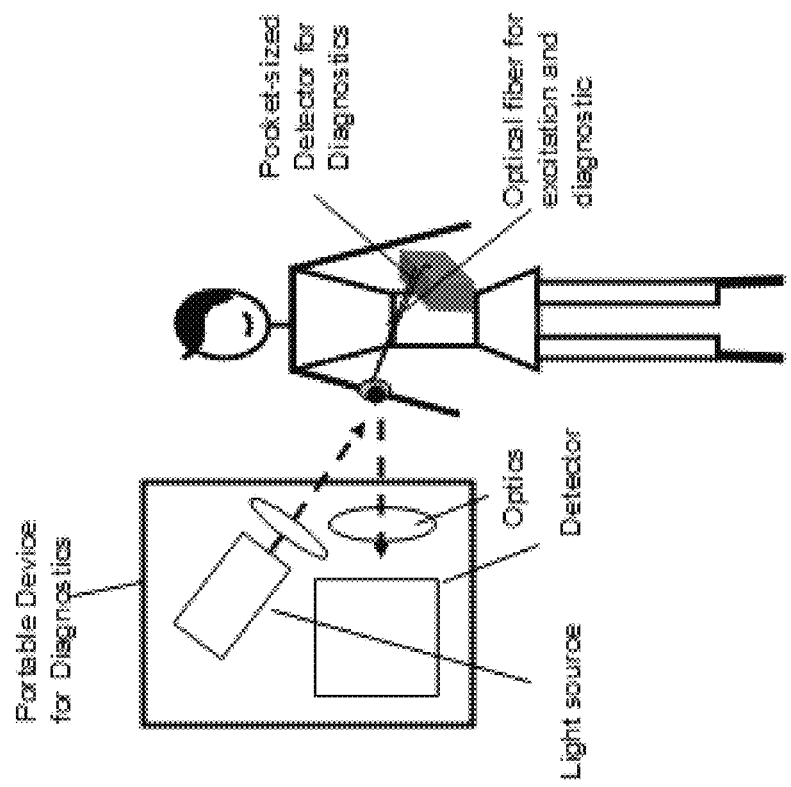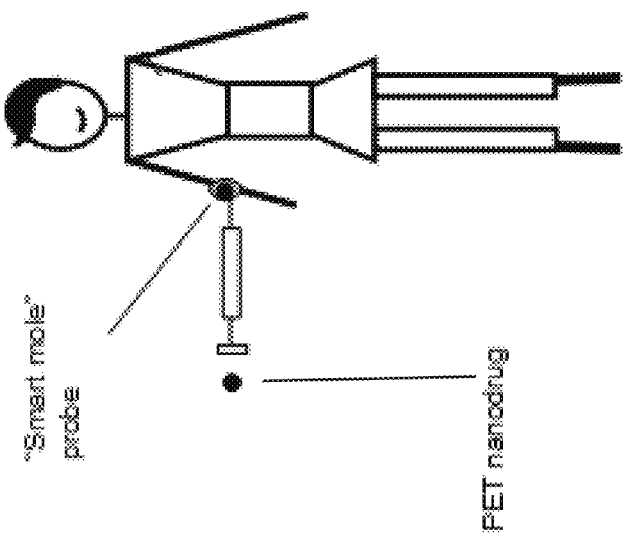

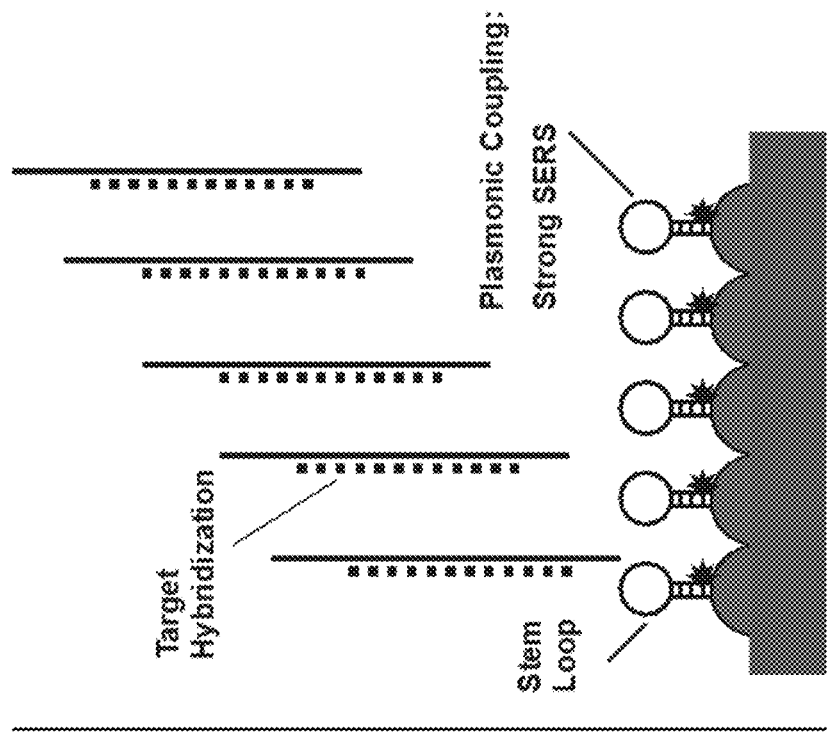
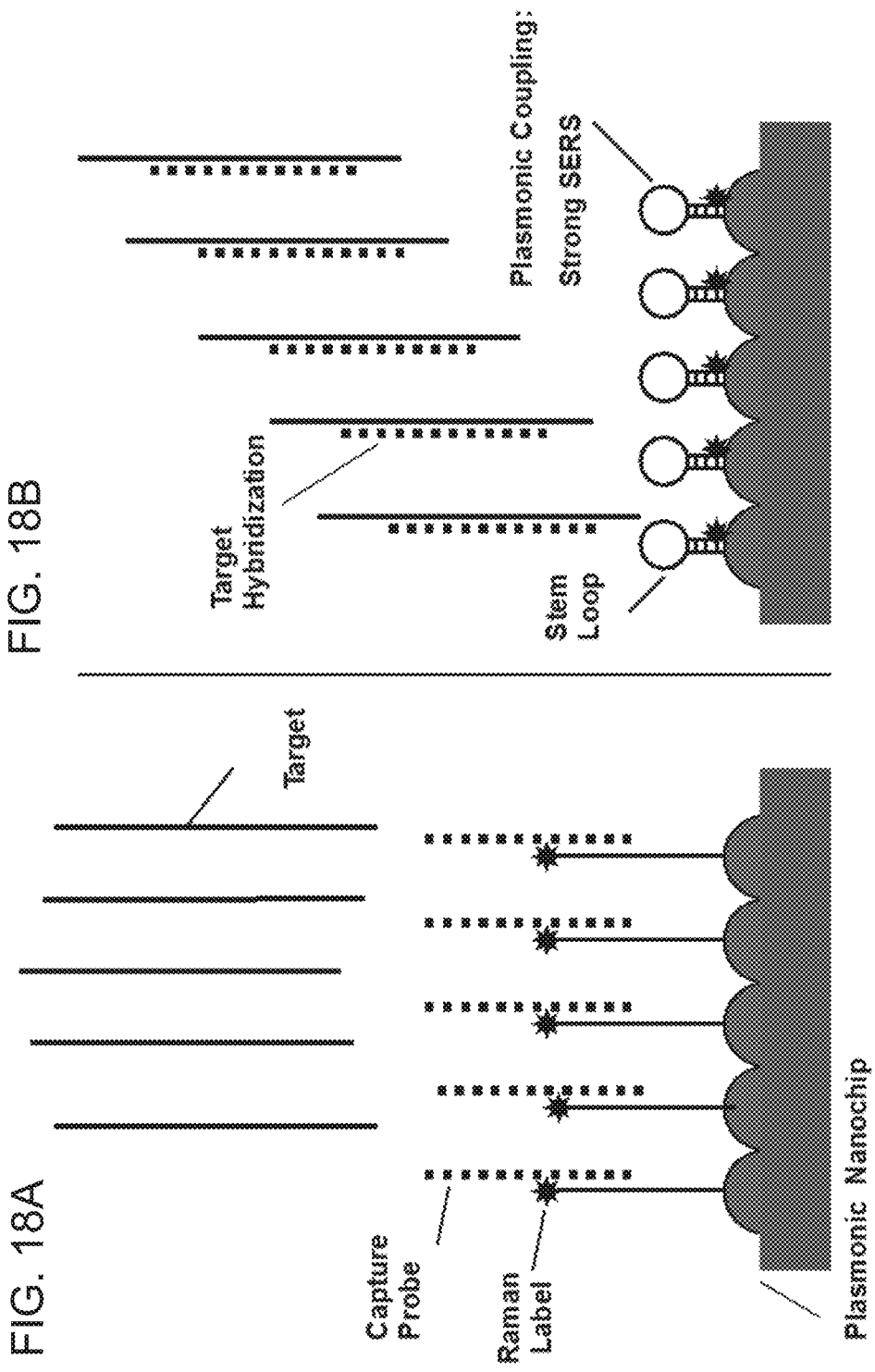
FIG. 18A
FIG. 18B

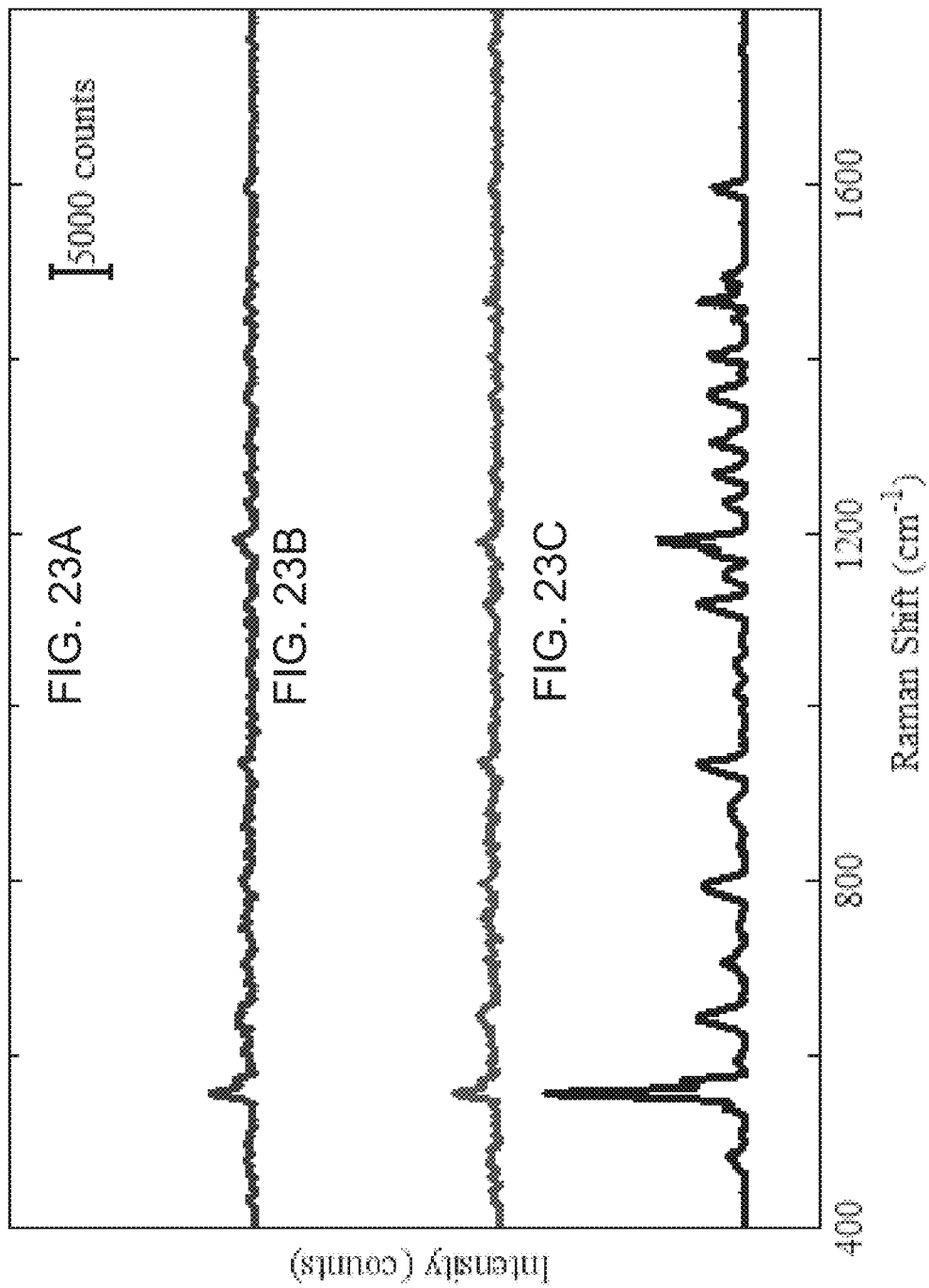

SEQUENCE LISTING

```
<160> NUMBER OF SEQ ID NOS: 4

<210> SEQ ID NO 1
<211> LENGTH: 28
<212> TYPE: DNA
<213> ORGANISM: Homo sapiens

<400> SEQUENCE: 1
ctctataagt ggtgtaggga ttatagag                                  28

<210> SEQ ID NO 2
<211> LENGTH: 28
<212> TYPE: DNA
<213> ORGANISM: Homo sapiens

<400> SEQUENCE: 2
gaaagcgact ctataatccc tacaccac                                  28

<210> SEQ ID NO 3
<211> LENGTH: 50
<212> TYPE: DNA
<213> ORGANISM: Homo sapiens

<400> SEQUENCE: 3
aaagctgagg aggtggtgta gggattatag agtcgctttc aagataaatt          50

<210> SEQ ID NO 4
<211> LENGTH: 40
<212> TYPE: DNA
<213> ORGANISM: Homo sapiens

<400> SEQUENCE: 4
tcatccatga caactttggt atcgtggaag gactcatgac                     40
```

NANO-PLASMONIC MOLECULAR PROBES AND METHODS OF USE

CROSS REFERENCE TO RELATED APPLICATIONS

This application is a continuation application of U.S. patent application Ser. No. 14/861,353 filed Sep. 22, 2015, which is a continuation application of International Patent Application No. PCT/US2013/059312 filed Sep. 11, 2013, which claims priority to U.S. Provisional Patent Application No. 61/804,346 filed Mar. 22, 2013, the disclosures of which are incorporated herein by reference in their entireties. This application is related to U.S. patent application Ser. No. 14/024,565 filed Sep. 11, 2013, U.S. patent application Ser. No. 13/888,226 filed May 6, 2013, and U.S. patent application Ser. No. 13/971,822 filed Aug. 20, 2013, the disclosures of which are incorporated herein by reference in their entireties.

STATEMENT OF GOVERNMENT SUPPORT

This invention was made with U.S. Government support under the National Institutes of Health Grant No. T32 EB001040 and the Defense Advanced Research Projects Agency Grant No. HR0011-13-2-003. The U.S. Government has certain rights in the invention.

TECHNICAL FIELD

The present disclosure relates to nano-plasmonic molecular probes and their methods of use for in vitro and in vivo detection, diagnosis and therapy.

BACKGROUND

In plasmonics and enhanced electromagnetic fields there are two main sources of electromagnetic enhancement: (1) the laser electromagnetic field is enhanced due to the addition of a field caused by the polarization of the metal particle; (2) in addition to the enhancement of the excitation laser field, there is another enhancement due to the molecule radiating an amplified emission (luminescence, Raman, etc.) field, which further polarizes the metal particle, thereby acting as an antenna to further amplify a Raman/Luminescence signal.

Electromagnetic enhancements are divided into two main classes: a) enhancements that occur only in the presence of a radiation field, and b) enhancements that can occur even in the absence of a radiation field. The first class of enhancements is further divided into several processes. Plasma resonances on the substrate surfaces, also called surface plasmons, provide a major contribution to electromagnetic enhancement. An effective type of plasmonics-active substrate consists of nanostructured metal particles, protrusions, or rough surfaces of metallic materials. Incident light irradiating these surfaces excites conduction electrons in the metal, and induces excitation of surface plasmons leading to Raman/Luminescence enhancement. At the plasmon frequency, the metal nanoparticles (or nanostructured roughness) become polarized, resulting in large field-induced polarizations and thus large local fields on the surface. These local fields increase the Luminescence/Raman emission intensity, which is proportional to the square of the applied field at the molecule. As a result, the effective electromagnetic field experienced by the analyte molecule on theses surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence).

Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents has thus introduced a much more selective and efficient phototherapy strategy.

One of several phenomena that can enhance the efficiency of light emitted (Raman or luminescence) from molecules adsorbed on or near a metal nanostructure is Raman scatter known as the surface enhanced Raman scattering (SERS) effect. The use of SERS measurement for a variety of chemicals including several homocyclic and heterocyclic polyaromatic compounds has been reported. [T. Vo-Dinh, M. Y. K. Hiromoto, G. M. Begun and R. L. Moody, "*Surface-enhanced Raman spectroscopy for trace organic analysis,*" *Anal. Chem.*, vol. 56, 1667, 1984]. Extensive research has been devoted to understanding and modeling the Raman enhancement in SERS since the mid 1980's. For example, Kerker published models of electromagnetic field enhancements for spherical silver nanoparticles and metallic nanoshells around dielectric cores as far back as 1984 [M. M. Kerker, *Acc. Chem. Res.*, 17, 370 (1984)]. Kerker's work illustrated theoretical calculations of electromagnetic enhancements for isolated spherical nanospheres and nanoshells at different excitation wavelengths. In his calculations, the intensity of the normally weak Raman scattering process was increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

The theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface. It has been widely accepted that the electromagnetic (EM) enhancement contributes the main part of enormous enhancement factor which greatly increases the intrinsically weak normal Raman scattering cross-section. Theoretical studies of EM effects have shown that the enhanced EM fields are confined within only a tiny region near the surface of the particles, and the SERS enhancement (G) falls off as $G=[r/(r+d)]^{1/2}$ for a single molecule located a distance d from the surface of a metal nanoparticle of radius r [K. Kneipp, H. Knepp, I. Itzkan, R. R Dasar, M. S. Feld, *J. phys. Condens. Matter* 14, R597 (2002)]. Thus, the EM enhancement factor G strongly decreases with increased distance between the analyte and metal surface.

A label-free detection system that uses a SERS-based "Molecular Sentinel" (MS) probe for multiplexed detection of gene targets has been published [T. Vo-Dinh, "*SERS Molecular Probe for Diagnostics and Therapy and Methods of Use Thereof*", U.S. Pat. No. 7,951,535 (2011)]. The MS nanoprobe is composed of a DNA hairpin probe (30-45 nucleotides) and metal nanoparticles. One end of the hairpin is tagged with a SERS-active label. At the other end, the probe is modified with a thiol group to covalently bond with the nanoparticle. The sequence within the loop region is complementary to the specific sequence being targeted for detection. In the absence of the target, the Raman label is in close proximity to the metal surface (closed state), and a strong SERS signal is detected due to the 'plasmonic' enhancement mechanism near the metallic nanoparticle. The SERS enhancement (G) falls off as $G=[r/(r+d)]^{1/2}$ for a single analyte molecule located a distance d from the surface of a metal nanoparticle of radius r. The electromagnetic SERS enhancement strongly decreases with increased distance, due to a total intensity decay of $(1/d)^{1/2}$. In the presence of the specific DNA target, hybridization disrupts the stem-loop configuration (open state) and separates the Raman label from the metal nanoparticle. The SERS signal is therefore significantly quenched.

Molecular sentinels (MS) have been used to detect single nucleotide polymorphisms (SNPs) in a multiplex fashion. Specifically, the MS plasmonic nanoprobe method has be used to perform multiplex detection of invasive breast cancer markers in a homogenous solution assay without washing or separation steps. This design comprised two MS nanoprobes, EBRR2-MS and KI-67-MS, to target the erbB-2 and ki-67 cancer genes, respectively. The results showed that only the SERS peaks associated with the complementary MS nanoprobes were significantly quenched when in the presence of the target DNA.

In addition to the EM enhancement contributed from individual particles, it has been observed that the EM field is particularly strong in the interstitial space between the particles. It is believed that the anomalously strong Raman signal originates from "hot spots", i.e., regions where clusters of several closely-spaced nanoparticles are concentrated in a small volume. The high-intensity SERS then originates from the mutual enhancement of surface plasmon local electric fields of several nanoparticles that determine the dipole moment of a molecule trapped in a gap between metal surfaces. This effect is also referred to as interparticle coupling or plasmonic coupling in a network of nanoparticles (NPs), and the effect can produce a further enhancement in addition to the enhancement from individual particles. The problem of predicting the electromagnetic field in the gaps between metal nanoparticles under optical illumination has attracted interest in recent years because of the very large field enhancements induced in the particle gaps arising from surface plasmon resonances.

To investigate this feature, the electric field was calculated surrounding a finite chain of metal nanospheres or nanospheroids when illuminated with coherent light [S. J. Norton and T. Vo-Dinh, "*Optical response of linear chains of nanospheres and nanospheroids,*" *J. Opt. Soc. Amer.* 25, 2767-2775 (2007)]. The chain structure consists of nanoparticles aligned closely with small gaps between them. A method was developed applicable to spheres and spheroids which avoided the use of translational formulas at the expense of the numerical, but allowed for straightforward evaluation of certain simple integrals. In this work, the quasi-static approximation was assumed, but the basic approach could be extended to the full-wave problem, in which retardation affects were accounted for. The approach was illustrated by computing the electric field in the gaps between two spheres and between two spheroids over a range of frequencies so that the induced plasmon resonances were evident. At frequencies matching the plasmon resonances, very large field enhancements were observed to occur. It was also demonstrated how the field enhancement varied with the aspect ratio of a prolate spheroid.

Plots were generated showing the calculated values of the magnitude of the electric field between two spheres and between two prolate spheroids with two different aspect ratios. The plots showed the calculated value of the field magnitude over a range of wavelengths at a point on axis in the gap midway between the two particles. The magnitude of the incident electric field was unity; thus, the plots showed the field enhancement relative to the incident field. The observed peaks corresponded to the frequencies of the plasmon resonances. Because of the assumption of a uniform incident electric field (the quasi-static approximation), the enhancement is scale invariant; that is, the enhancement only depends on the ratio of the gap width to the particle size (e.g., the radius of a sphere or, for a spheroid, the lengths of the semi-major and semi-minor axes).

In the calculations, three pairs of particles were compared with different gaps between them: a pair of identical spheres of unit radius, and a pair of prolate spheroids with two different aspect ratios but equal in volume to that of the sphere. It was noted that the plasmon resonance red-shifted with increasing aspect ratio. In addition, for a given gap width, the two spheroids produced a noticeably larger enhancement than the two spheres. This was expected, since the smaller curvature at the spheroid ends creates a larger surface charge density and a larger field. The increased field that was observed at the ends was attributed to the "lighting rod effect." The pair of nanospheres having an aspect ratio of 4 and a 2% gap showed an electric field enhancement in the gap of over 700 at the peak of the plasmon resonance. The total SERS signal was approximately proportional to the fourth power of the electric field magnitude, giving a total SERS enhancement of over $4\times10^{10}$. However, a spatially averaged enhancement would be much less than this observed peak value. [Ref: S. J. Norton and T. Vo-Dinh, "*Optical response of linear chains of nanospheres and nanospheroids,*" *J. Opt. Soc. Amer.* 25, 2767-2775 (2007)].

The detection of nucleic acid (DNA or RNA) sequences is critical for many applications ranging from clinical diagnostics, environmental monitoring, food safety inspection, to homeland security. For medical applications nucleic acid biomarkers, such as DNA, mRNA and microRNA, have long been considered as valuable diagnostic indicators to monitor the presence of diseases and their progression. These biomarkers have great potential for early diagnosis and as therapeutic targets for effective treatment of diseases. Therefore, much effort has been devoted to the development of sensitive, selective and practical techniques for the detection of nucleic acid biomarkers.

There has been increasing interest in the use of surface-enhanced Raman scattering (SERS) for detection of nucleic acid sequences of interest (e.g. nucleic acid sequences associated with a given disease). The SERS effect greatly increases the Raman scattering cross-section enabling the use of SERS for extremely sensitive detection of the analytes. The enhancement mechanism for SERS mainly comes from intense localized electromagnetic (EM) fields arising from surface plasmon resonance in metallic nanostructures with sizes on the order of tens of nanometers. Reports on the large SERS enhancement factors of $10^{12}$-$10^{15}$ have inspired the development of new sensing materials allowing sensitive detection of analytes, even down to single molecules. Together with the narrow linewidth and the molecular specific vibrational bands, SERS has now been considered as a powerful spectroscopy approach for biochemical analysis and medical diagnostics.

With recent advances in nanotechnology, a variety of different approaches have been developed to detect DNA or RNA molecules using SERS-active metallic (e.g. silver and gold) nanoparticles or nanostructured substrates. A variety of SERS plasmonic platforms have been developed for chemical and biological sensing, including a label-free detection system that uses SERS-based "Molecular Sentinel" (MS) nanoprobes for multiplexed detection of gene targets. The MS nanoprobe consists of a "stem-loop" DNA probe having a Raman label molecule at one end and a metallic nanoparticle at the other end. The detection principle of MS is based on the plasmonic enhancement mechanism near the metallic nanoparticle (i.e. the enhanced EM fields are confined near the surface of metallic nanoparticles). Upon recognition of targets, hybridization between stem-loop probes and target strands disrupts the stem-loop configuration and moves the Raman label away from the metal surface. This switches the probe conformation from a closed stem-loop structure to an open linear duplex, leading to a decrease in the SERS signal ("On-to-Off") as the SERS enhancement strongly decreases with increased distance between the dye and metallic nanostructured surface.

New nano-plasmonic compositions having improved properties and methods of use are desireable to take advantage of the tunability of the spectral properties of the metal nanoparticles.

SUMMARY OF THE INVENTION

In one embodiment, a method is provided for detecting nucleic acid targets, comprising: contacting a nanoprobe directed to a nucleic acid target with the target under conditions suitable for the target to hybridize with the nanoprobe, wherein the nanoprobe comprises: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder nucleic acid complementary to the placeholder binding sequence and complementary to the target, wherein the placeholder nucleic acid is hybridized to the placeholder sequence in the absence of the target such that formation of the hairpin structure is prevented; and an optical label attached to the oligonucleotide, irradiating the sample with electromagnetic radiation from an excitation source; and detecting the electromagnetic radiation originated by the label, wherein a level of electromagnetic radiation originated by the label in the presence of the target is changed due to movement of the label into the vicinity of the nanoparticle electromagnetic enhancement upon formation of the hairpin structure.

In one embodiment, a nanoprobe is provided for detecting nucleic acid targets, comprising: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder nucleic acid complementary to the placeholder binding sequence and complementary to the target, wherein the placeholder nucleic acid is hybridized to the placeholder sequence in the absence of the target such that formation of the hairpin structure is prevented; and an optical label attached to the oligonucleotide.

In one embodiment, a method is provided for detecting nucleic acid targets, comprising: contacting a nanoprobe directed to a nucleic acid target with the target under conditions suitable for the target to hybridize with the nanoprobe, wherein the nanoprobe comprises: at least one silver-coated gold nanostar resulting from a process comprising reducing aqueous silver ($Ag^+$) to solid silver ($Ag^0$) onto gold nanostar seeds under conditions such that the silver-coated gold nanostars are produced; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder nucleic acid complementary to the placeholder binding sequence and complementary to the target, wherein the placeholder nucleic acid is hybridized to the placeholder sequence in the absence of the target such that formation of the hairpin structure is prevented; and an optical label attached to the oligonucleotide; irradiating the sample with electromagnetic radiation from an excitation source; and detecting the electromagnetic radiation originated by the label, wherein a level of electromagnetic radiation originated by the label in the presence of the target is changed due to movement of the label into the vicinity of the nanoparticle electromagnetic enhancement upon formation of the hairpin structure.

In one embodiment, a method is provided for detecting protein and small molecule targets, comprising: contacting a nanoprobe directed to a protein target or a small molecule target with the target under conditions suitable for the nanoprobe to bind to the target, wherein the nanoprobe comprises: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder aptamer bound to the placeholder binding sequence such that formation of the hairpin structure is prevented, wherein the placeholder aptamer is capable of binding to the target; and an optical label attached to the oligonucleotide, irradiating the sample with electromagnetic radiation from an excitation source; and detecting the electromagnetic radiation originated by the label, wherein a level of electromagnetic radiation originated by the label in the presence of the target is changed due to movement of the label into the vicinity of the nanoparticle electromagnetic enhancement upon formation of the hairpin structure.

In one embodiment, a method is provided for detecting nucleic acid targets, comprising: contacting a first and a second nanoprobe directed to a nucleic acid target with the target under conditions suitable for the target to hybridize with the nanoprobes, wherein the first and the second nanoprobes comprise: at least one metal nanoparticle; an oligonucleotide probe attached at one end to the nanoparticle, the probe of the first nanoprobe including a sequence that is complementary to a first half of the target and the probe of the second nanoprobe including a sequence that is complementary to a second half of the target; and a first label attached to the first probe and a separate second label attached to the second probe, irradiating the sample with electromagnetic radiation from an excitation source; and detecting the electromagnetic radiation originated by both of the first and second labels, wherein a level of electromagnetic radiation originated by the labels in the presence of the target is changed upon hybridization of the probes with the target due to movement of the labels in between the nanoparticles.

In one embodiment, a pair of nanoprobes are provided for detecting nucleic acid targets, each of a first and a second nanoprobe comprising: at least one metal nanoparticle; an oligonucleotide probe attached at one end to the nanoparticle, the probe of the first nanoprobe including a sequence that is complementary to a first half of a target and the probe of the second nanoprobe including a sequence that is complementary to a second half of the target; and a first label attached to the first probe and a separate second label attached to the second probe.

In one embodiment, a method is provided for detecting protein targets, comprising: contacting a first and a second nanoprobe directed to a protein target with the target under conditions suitable for the nanoprobes to bind to the target, wherein the first and the second nanoprobes comprise: at least one metal nanoparticle; a bioreceptor attached to the nanoparticles, the bioreceptor of the first nanoprobe capable of binding to a first site on the protein target and the bioreceptor of the second nanoprobe capable of binding to a second site on the protein target; and a first label attached to the first bioreceptor and a separate second label attached to the second bioreceptor, irradiating the sample with electromagnetic radiation from an excitation source; and detecting the electromagnetic radiation originated by both of the first and second labels, wherein a level of electromagnetic radiation originated by the labels in the presence of the target is changed upon binding of each of the bioreceptors to the target due to movement of the labels in between the nanoparticles.

In one embodiment, a pair of nanoprobes are provided for detecting protein targets, each of a first and a second nanoprobe comprising: at least one metal nanoparticle; a bioreceptor attached to the nanoparticle, the bioreceptor of the first nanoprobe capable of binding to a first site on a protein target and the bioreceptor of the second nanoprobe capable of binding to a second site on the protein target; and a first label attached to the first bioreceptor and a separate second label attached to the second bioreceptor.

In one embodiment, a method is provided for detecting protein targets, comprising: contacting a nanoprobe comprising: at least one metal nanoparticle; a ligand attached to the nanoparticle capable of binding to a protein target; and an optical label attached to the nanoparticle, with the target under conditions suitable for both the nanoprobe to bind to the target and for the nanoparticles to self assemble into closely packed arrays in the absence of the target such that electromagnetic field enhancement occurs between neighboring nanoparticles, irradiating the sample with electromagnetic radiation from an excitation source; and detecting the electromagnetic radiation originated by the label, wherein a level of electromagnetic radiation originated by the label is decreased upon binding of the ligand to the target due to movement of the metal nanoparticles further apart such that the label is less affected by electromagnetic field enhancement between neighboring nanoparticles.

In one embodiment, a nanoprobe is provided for detecting protein targets, comprising: at least one metal nanoparticle; a ligand attached to the nanoparticle capable of binding to a protein target; and an optical label attached to the nanoparticle.

In one embodiment, a silver-coated gold nanostar is provided resulting from a process comprising reducing aqueous silver ($Ag^+$) to solid silver ($Ag^0$) onto gold nanostar seeds under conditions such that the silver-coated gold nanostars are produced.

In one embodiment, a nanoprobe is provided comprising: a silver-coated gold nanostar resulting from a process comprising reducing aqueous silver ($Ag^+$) to solid silver ($Ag^0$) onto gold nanostar seeds under conditions such that the silver-coated gold nanostars are produced; and an optical label capable of absorbing electromagnetic radiation originated as a result of excitation of the nanostar with excitation radiation.

In one embodiment, a method is provided for treating undesirable cells comprising: contacting an undesirable cell with the silver-coated gold nanostar resulting from a process comprising reducing aqueous silver ($Ag^+$) to solid silver ($Ag^0$) onto gold nanostar seeds under conditions such that the silver-coated gold nanostars are produced and having an optical label; and irradiating the sample with electromagnetic radiation from an excitation source, wherein the optical label is capable of absorbing electromagnetic radiation from one or both of electromagnetic radiation originated as a result of excitation of the nanostar and directly from the excitation radiation, and wherein the undesirable cells are damaged by one or both of thermal energy direct from the radiation and thermal energy emitted as a result of excitation of the nanostar.

In one embodiment, a method is provided for treating undesirable cells comprising: contacting an undesirable cell with a nanoprobe of the present disclosure; and irradiating the sample with electromagnetic radiation from an excitation source, wherein the optical label is capable of absorbing electromagnetic radiation from one or both of electromagnetic radiation originated as a result of excitation of the nanoparticle and directly from the excitation radiation, and wherein the undesirable cells are damaged by one or both of thermal energy direct from the radiation and thermal energy emitted as a result of excitation of the nanoparticle.

In one embodiment, a method is provided for detecting nucleic acid targets, comprising: contacting a nanoprobe directed to a nucleic acid target with the target under conditions suitable for the target to hybridize with the nanoprobe, wherein the nanoprobe comprises: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; and a placeholder nucleic acid complementary to the placeholder binding sequence and complementary to the target, wherein the placeholder nucleic acid is hybridized to the placeholder sequence in the absence of the target such that formation of the hairpin structure is prevented; and detecting a color change in the presence of the target upon formation of the hairpin structure. The color change can be a visible color change.

In one embodiment, a method is provided for detecting nucleic acid targets, comprising: contacting a pair of nanoprobes having at least one metal nanoparticle and an oligonucleotide probe attached at one end to the nanoparticle, the probe of the first nanoprobe including a sequence that is complementary to a first half of a target and the probe of the second nanoprobe including a sequence that is complementary to a second half of the target, with a target under conditions suitable for the target to hybridize with the nanoprobes; and detecting a color change in the presence of the target upon hybridization of the probes with the target. The color change can be a visible color change.

In one embodiment, a method is provided for detecting nucleic acid targets, comprising: contacting a pair of nanoprobes having at least one metal nanoparticle and a bioreceptor attached to the nanoparticle, the bioreceptor of the first nanoprobe capable of binding to a first site on a protein target and the bioreceptor of the second nanoprobe capable of binding to a second site on the protein target, with a target under conditions suitable for the target to bind to the nanoprobes; and detecting a color change in the presence of the target upon binding of the bioreceptors to the target. The color change can be a visible color change.

In one embodiment, a method is provided for detecting nucleic acid targets, comprising: contacting a nanoprobe having at least one metal nanoparticle and a ligand attached to the nanoparticle capable of binding to a protein target, with a target under conditions suitable for the target to bind to the nanoprobe; and detecting a color change in the presence of the target upon binding of the ligand to the target. The color change can be a visible color change.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

FIG. 9 is a schematic diagram illustrating the plasmonic nanoprobe for detection of protein targets according to embodiments of the present disclosure.

FIGS. 10A-10K are schematic diagrams showing various embodiments of plasmonics-active nanoparticles of according to the present disclosure: A) Metal nanoparticle; B) Dielectric nanoparticle core covered with metal nanocap; C) Spherical metal nanoshell covering dielectric spheroid core; D) Oblate metal nanoshell covering dielectric spheroid core; E) Metal nanoparticle core covered with dielectric nanoshell; F) Metal nanoshell with protective coating layer; G) Multi layer metal nanoshells covering dielectric spheroid core; H) Multi-nanoparticle structures; I) Metal nanocube and nanotriangle/nanoprism; J) Metal cylinder; and K) legend.

FIGS. 16A-16B are schematic diagrams showing use of the plasmonic nanoprobes as an in vive diagnostic according to embodiments of the present disclosure.

FIGS. 18A-18B are schematic diagrams illustrating the iMS-on-Chip system according to embodiments of the present disclosure.

FIGS. 23A-23C are a series of graphs showing SERS spectra of the RSAD2-iMS nanoprobes in the presence or absence of complementary DNA targets according to embodiments of the present disclosure. A) Blank (no target DNA present). B) In the presence of 1 µM non-complementary DNA (negative control). C) In the presence of 1 µM complementary target DNA.

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "a cell" means at least one cell and can include a number of cells.

Unless otherwise defined, all technical terms used herein have the same meaning as commonly understood by one of ordinary skill in the art to which this disclosure belongs.

As used herein, the term "nanostar" or "NS" means a nanoparticle which has a single core section with two or more protrusions emitting from the core section of the nanoparticle. These protrusions are usually conical or pyramidal in form, but not always.

As used herein, the terms "nanoprobe" and "nano-plasmonic probe" and "nano-plasmonic molecular probe" and "plasmonics-active nanoprobe" and "nanosensor" and "sensor" and "biosensor" are used herein interchangeably for the purposes of the specification and claims and are meant to refer to the molecular probes of the present disclosure comprising one or more plasmonics-active nanoparticles and an attached molecular label such as, for example, a Raman dye; the molecular probes useful for detecting biological targets including, but not limited to, nucleic acids, proteins, and cells. An inverse molecular sentinel (iMS) is one type of nanoprobe provided by the present disclosure. Thus, the iMS nanoprobe is herein referred to interchangeably as "iMS", "iMS nanoprobe", "iMS sensor", "iMS biosensor", sensor, biosensor, etc.

Figure 1:
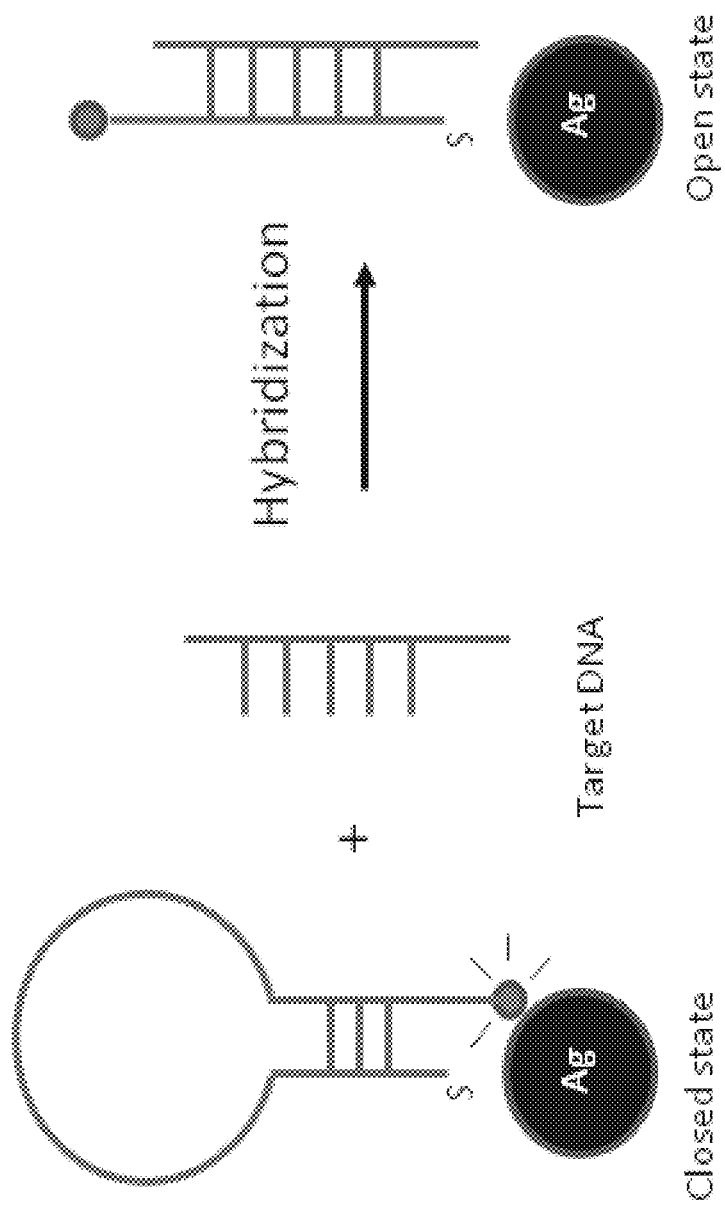
FIG. 1 is a schematic diagram showing a DNA hairpin structure attached to a metallic nanoparticle to form a molecular detector termed a "molecular sentinel" (MS). The MS involves an "On-to-Off" negative-contrast signaling scheme.

In one embodiment, the present disclosure provides a detection approach that incorporates a SERS effect modulation scheme associated with metallic nanoparticles and a DNA hairpin structure. Previously, a DNA hairpin structure was attached to a metallic nanoparticle to form a molecular detector that was termed a "molecular sentinel" (MS). The MS involves an "On-to-Off" negative-contrast signaling scheme shown in FIG. 1. Here, a new "Off-to-On" detection scheme is provided based on an "inverse Molecular Sentinel" (iMS) (FIG. 2). FIG. 2 illustrates the iMS nanoprobe having a Raman label at one end of an oligonucleotide that is immobilized onto a metallic nanoparticle (NP) via a Au-thiol bond formed on the other end of the olionucleotide. The label can be attached at any distance from the nanoparticle such that the label is not affected by electromagnetic enhancement of the nanoparticle when the nanoprobe is in the Off state.

Figure 2A:
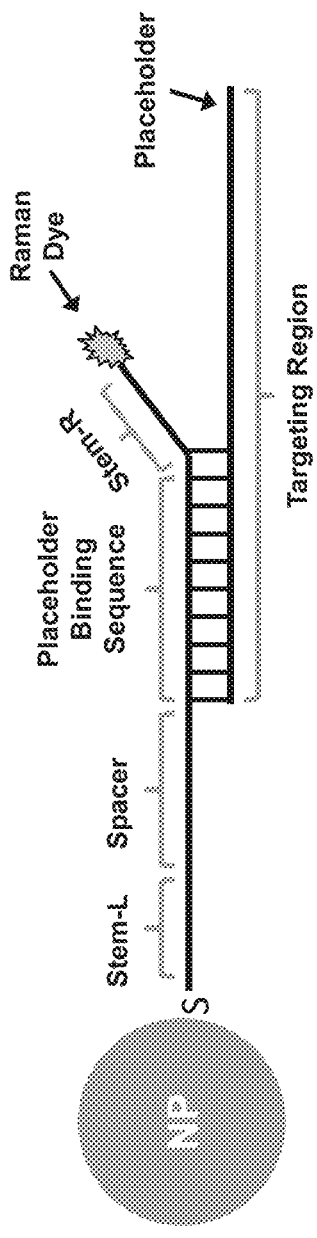
FIGS. 2A-2C illustrate an "Off-to-On" detection scheme based on an "inverse Molecular Sentinel" (iMS) nanoprobe according to embodiments of the present disclosure. A) The nanoprobe is shown having an oligonucleotide attached at one end to a nanoparticle (NP), the oligonucleotide including a spacer, and a stem-L and a stem-R sequence capable of hybridizing to form a hairpin structure, a placeholder binding sequence in between the stem-L and stem-R sequences, the nanoprobe also including a placeholder complementary to the placeholder binding sequence and to the target (targeting region), and a Raman dye attached to the oligonucleotide. B) The nanoprobe is similar to that shown in (A) except that the spacer region is absent, a greater region of the placeholder is hybridized to the placeholder binding sequence, and the stem-R region overlaps with the placeholder binding sequence. C) The nanoprobe is similar to that shown in (A) except that the stem-R region overlaps with the placeholder binding sequence.
Figure 2B:
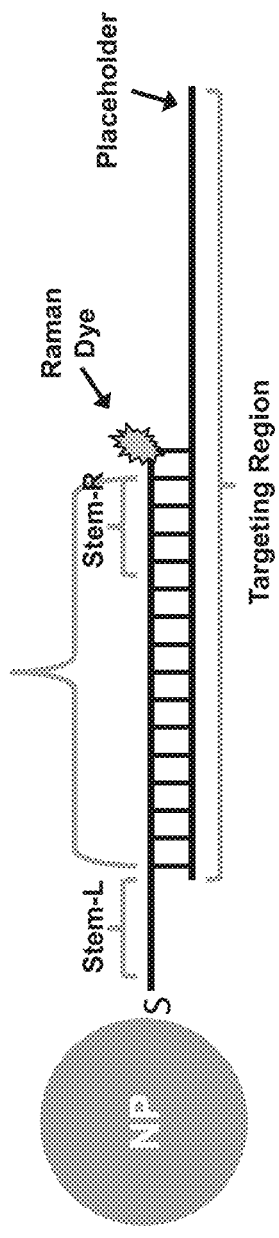
Figure 2C:
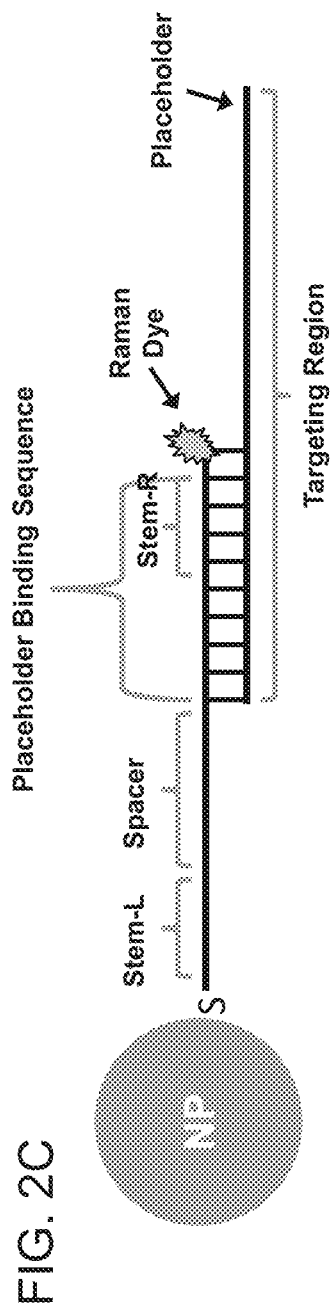

FIG. 2A shows the nanoprobe having an oligonucleotide attached at one end to a nanoparticle (NP), the oligonucleotide including a spacer, and a stem-L and a stem-R sequence capable of hybridizing to form a hairpin structure, a placeholder binding sequence in between the stem-L and stem-R sequences, the nanoprobe also including a placeholder complementary to the placeholder binding sequence and to the target (targeting region), and a Raman dye attached to the oligonucleotide. The nanoprobe in FIG. 2B is similar to that shown in FIG. 2A except that the spacer region is absent, a greater region of the placeholder is hybridized to the placeholder binding sequence, and the stem-R region overlaps with the placeholder binding sequence. The nanoprobe in FIG. 2C is similar to that shown in FIG. 2C except that the stem-R region overlaps with the placeholder binding sequence.

Figure 3B:
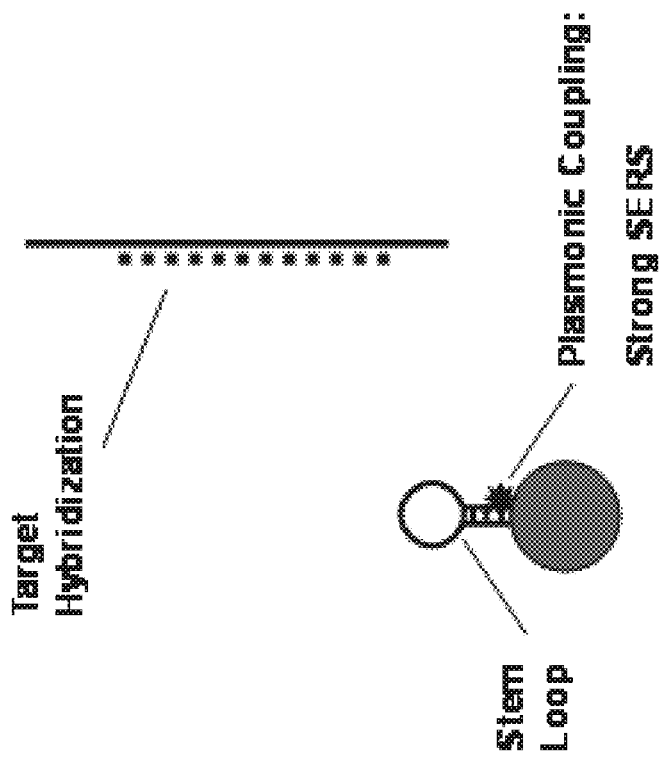
FIGS. 3A-3B are diagrams illustrating the mechanism of the iMS according to FIG. 2. 3A) The complementary "capture probe" serves as a placeholder strand by binding to the nucleic acid stem of the nanoprobe to keep the Raman label away from the nanoparticle surface in the 'Off' state. 3B) Upon exposure to the "target" sequence, the capture probe leaves the nanoprobe based on competitive binding to the target, allowing the stem-loop to "close" and move the Raman label onto the nanoparticle surface such that upon laser excitation, the Raman label experiences a strong plasmonic effect and generates an intense SERS signal, providing the 'On' state.
Figure 3A:
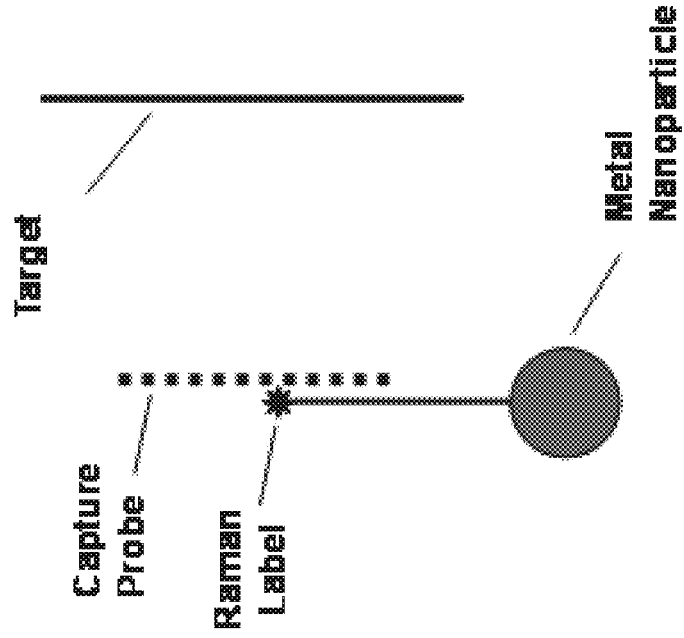

FIGS. 3A and 3B illustrate the mechanism of the iMS. FIG. 3A shows the complementary "capture probe" serving as a placeholder strand by binding to the nucleic acid stem of the nanoconstruct. The capture probe keeps the Raman label away from the nanoparticle surface; the probe is "open" with low SERS signal, which is the 'Off' state. FIG. 3B shows that upon exposure to the "target" sequence, the capture probe leaves the nanoconstruct based on competitive binding to the target, allowing the stem-loop to "close" and move the Raman label onto the nanoparticle surface. Upon laser excitation, the Raman label molecule experiences a strong plasmonic effect and generates an intense SERS signal, which is the "On" or "closed" state. Because the plasmon field enhancement decreases significantly from the surface of the NP, a molecule must be located within a very close range (0-10 nm) of the nanostructure surface in order to experience the enhanced local plasmon field. After hybridication with the target sequence the iMS can be regenerated by adding a new capture probe as a place holder.

Figure 4A:
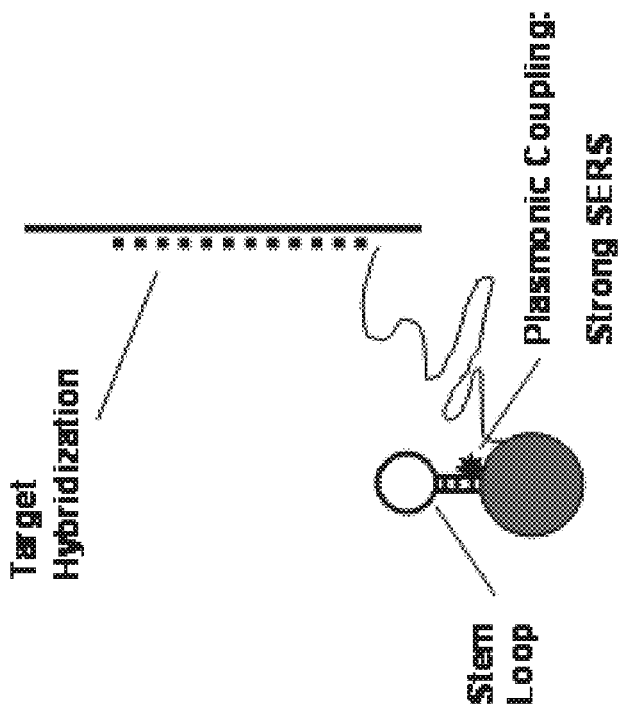
FIGS. 4A-4B are diagrams of the iMS nanoprobe according to FIGS. 3A-3B illustrating that the capture probe can be tethered to the nanoparticle such that the capture probe is kept near the nanoparticle and can be resused.
Figure 4B:
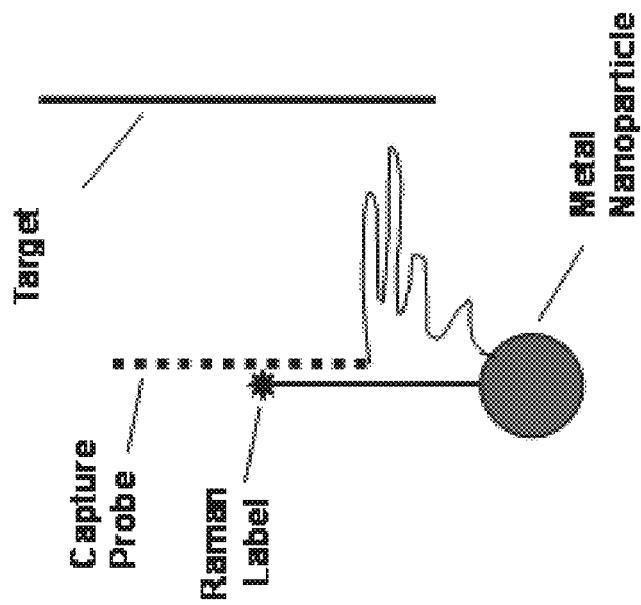

FIGS. 4A and 4B illustrate that the capture probe can be tethered to the nanoparticle such that the capture probe is kept near the nanoparticle and can be resused.

Figure 5A:
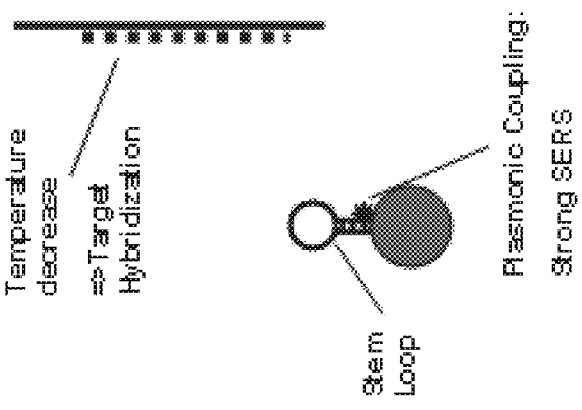
FIGS. 5A-5C are schematic diagrams depicting the iMS nanoprobe according to FIGS. 3A-3B using temperature cycling. A) Capture probe is used to keep the stem-loop in an open state. B) By increasing the sample temperature, the capture probe is dehybridized from the iMS nanoprobe. C) With temperature decrease and in the presence of the target sequence the capture probe hybridizes to the target allowing the stem-loop to close, bringing the Raman label to the nanoparticle surface for generation of a SERS signal.
Figure 5B:
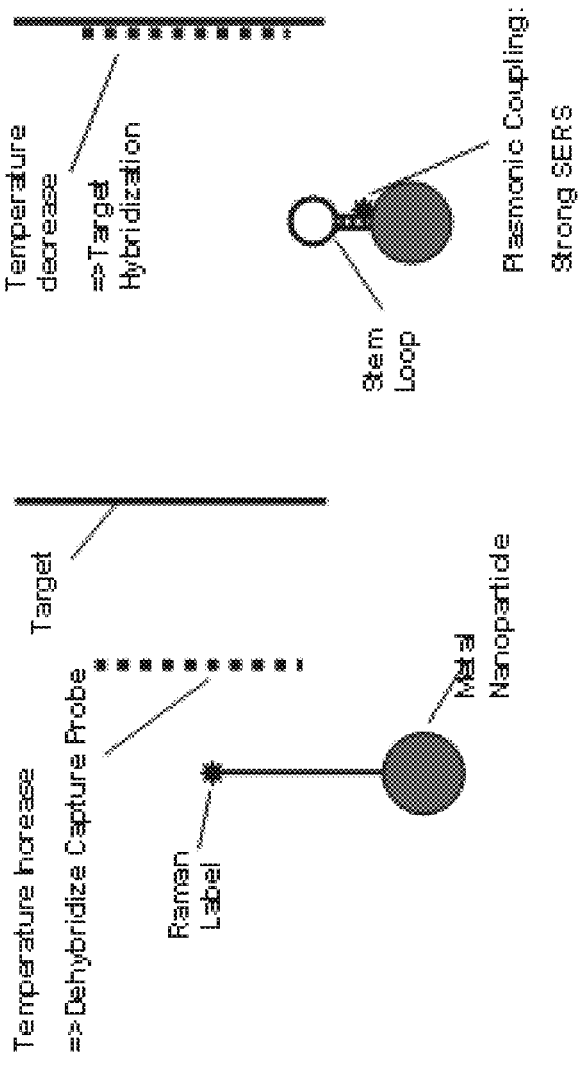
Figure 5C:
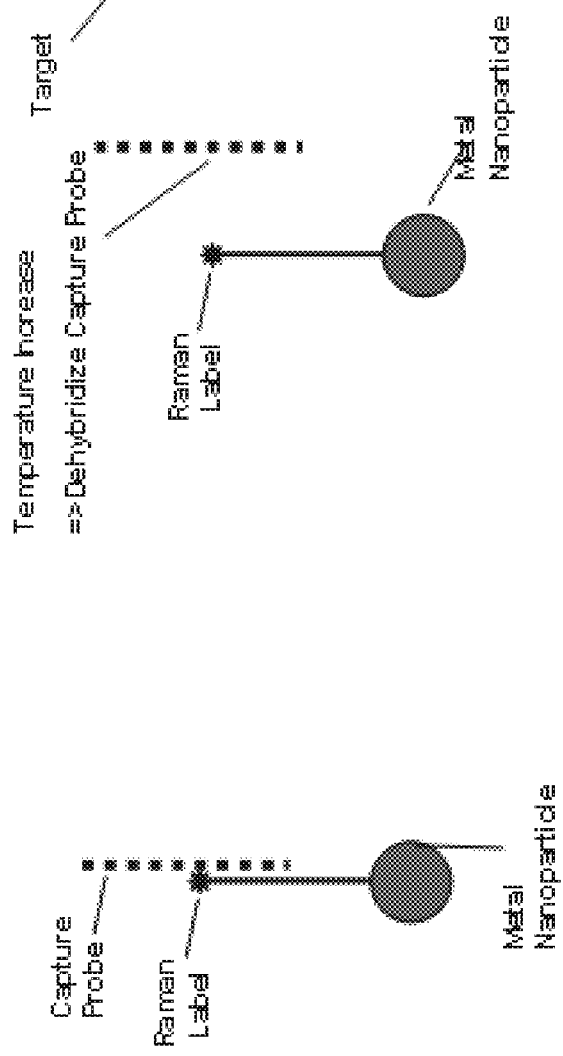

FIGS. 5A-5C are schematic diagrams depicting the iMS biosensor using temperature cycling. In FIG. 5A, the capture probe is shown being used to keep the stem-loop in an open state. FIG. 5B shows that by increasing the sample temperature, the capture probe is dehybridized from the iMS. FIG. 5C shows that with temperature decrease and in the presence of the target sequence the capture probe hybridizes to the target allowing the stem-loop to close, bringing the Raman label to the nanoparticle surface for generation of a SERS signal.

Figure 6A:
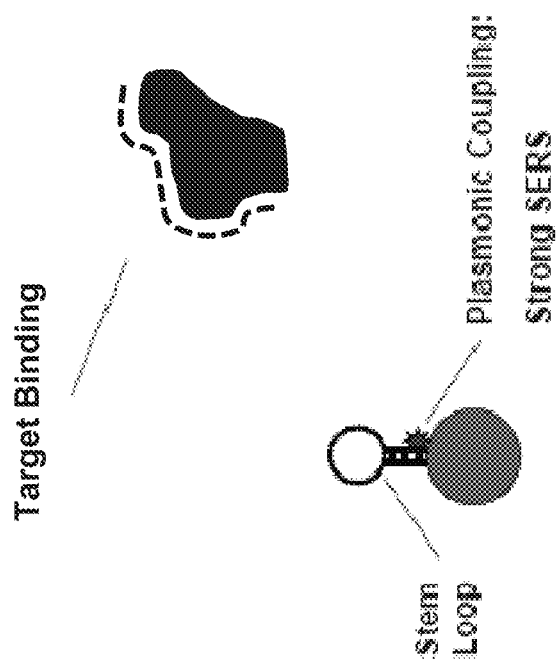
FIGS. 6A-6B are schematic diagrams illustrating the plasmonic nanoprobe for detection of protein and small molecule targets according to embodiments of the present disclosure.
Figure 6B:
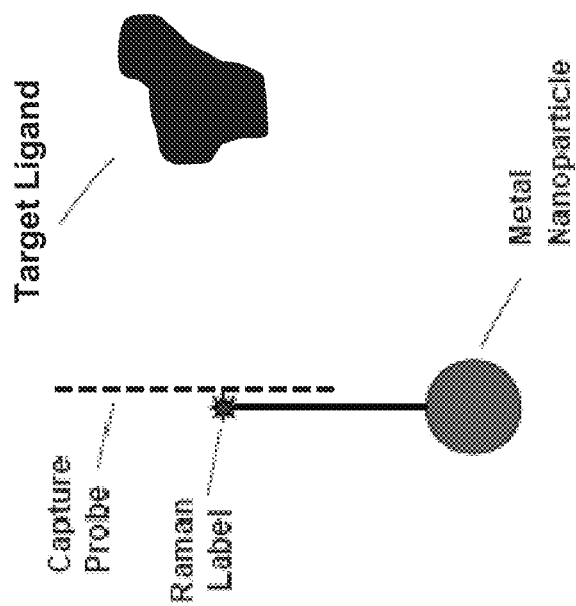

FIGS. 6A-6B are schematic diagrams illustrating the plasmonic nanoprobe for detection of protein and small molecule targets according to embodiments of the present disclosure. The nanoprobe depicted in FIGS. 6A-6B is similar to the nanoprobe shown in FIGS. 3A-3B except that the target can be a a small molecule as well as a protein and the capture probe (placeholder) is an aptamer.

Various nanoparticles including silver nanospheres, gold nanospheres, nanoshells and nanostars, can be used to yield intense SERS signal of a label at different plasmon resonance wavelengths. Looking at the iMS biosensor of FIG. 2, the nucleic acid stem can have a thiol group at one end for attaching to the nanoparticle and can have a Raman dye at the other end to act as a reporter. The nucleic acid stem reporter strand can have four segments: stem-L, stem-R, spacer and placeholder. The stem-L and stem-R segments allow the stem-loop structure to form after the placeholder strand binds to the target molecule and leaves the nanoconstruct. The "placeholder" or "placeholder strand" is herein used interchangeably with the term "capture probe". The spacer is designed to provide sufficient distance (over 10 nm) between the Raman dye and nanoparticle surface to reduce background SERS signal when the probe is in the open state. The placeholder (8-15 nucleotides) binds to the placeholder strand to prevent the formation of the stem-loop structure. The placeholder strand has two segments: placeholder-C and targeting region. The placeholder-C segment is complementary to the placeholder segment of the stem and to the target sequences. The targeting region (20-30 nucleotides) is complementary to the target sequence.

In one embodiment, a method is provided for detecting nucleic acid targets, comprising: contacting a nanoprobe directed to a nucleic acid target with the target under conditions suitable for the target to hybridize with the nanoprobe, wherein the nanoprobe comprises: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder nucleic acid complementary to the placeholder binding sequence and complementary to the target, wherein the placeholder nucleic acid is hybridized to the placeholder sequence in the absence of the target such that formation of the hairpin structure is prevented; and an optical label attached to the oligonucleotide, irradiating the sample with electromagnetic radiation from an excitation source; and detecting the electromagnetic radiation originated by the label, wherein a level of electromagnetic radiation originated by the label in the presence of the target is changed due to movement of the label into the vicinity of the nanoparticle electromagnetic enhancement upon formation of the hairpin structure.

In one embodiment, a nanoprobe is provided for detecting nucleic acid targets, comprising: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder nucleic acid complementary to the placeholder binding sequence and complementary to the target, wherein the placeholder nucleic acid is hybridized to the placeholder sequence in the absence of the target such that formation of the hairpin structure is prevented; and an optical label attached to the oligonucleotide.

In one embodiment, a method is provided for detecting nucleic acid targets, comprising: contacting a nanoprobe directed to a nucleic acid target with the target under conditions suitable for the target to hybridize with the nanoprobe, wherein the nanoprobe comprises: at least one silver-coated gold nanostar resulting from a process comprising reducing aqueous silver ($Ag^+$) to solid silver ($Ag^0$) onto gold nanostar seeds under conditions such that the silver-coated gold nanostars are produced; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder nucleic acid complementary to the placeholder binding sequence and complementary to the target, wherein the placeholder nucleic acid is hybridized to the placeholder sequence in the absence of the target such that formation of the hairpin structure is prevented; and an optical label attached to the oligonucleotide; irradiating the sample with electromagnetic radiation from an excitation source; and detecting the electromagnetic radiation originated by the label, wherein a level of electromagnetic radiation originated by the label in the presence of the target is changed due to movement of the label into the vicinity of the nanoparticle electromagnetic enhancement upon formation of the hairpin structure.

The optical label can comprises a Raman dye, 3,3'-Diethylthiadicarbocyanine iodide (DTDC), 3,3'-diethylthiatricarbocyanine iodide (DTTC), 1,1',3,3,3',3'-Hexamethylindotricarbocyanine iodide (HITC), CY3 dye, CY3.5 dye, CY5.5 dye, CY7 dye, CY7.5 dye, a positively-charged hydrophobic near infrared (NIR) dye, IR-780, IR-792, IR-797, IR-813, methylene blue hydrate (MB), 4-mercaptobenzoic acid (4-MBA), 5,5'-dithiobis-2-nitrobenzoic acid (DTNB), 4-aminothiophenol (4ATP), fluorescein, fluorescein isothiocyanate (FITC), thionine dyes, rhodamine-based dye, crystal violet, a fluorescence label, or an absorbance label.

Detecting the electromagnetic radiation originated by the label can be by one or more of surface enhanced Raman scattering (SERS) detection, surface-enhanced resonance Raman scattering (SERRS), fluorescence detection and absorbance detection.

The nucleic acid target can include a DNA, an RNA, a microRNA, a mRNA, or a single polynucleotide polymorphism (SNP). The placeholder nucleic acid can include an siRNA or an anti-microRNA. The placeholder nucleic acid can be tethered to the metal nanoparticle.

The contacting of the nanoprobe with the target can occur in an ki vitro assay. The method can include increasing the temperature during the contacting step to dehybridize the placeholder nucleic acid from the oligonucleotide.

In the method, the contacting of the nanoprobe with the target can include a second nanoprobe and a second target, and the second nanoprobe can include a second label that is directed to the second target. In the method, the detecting can be performed using multiplexing such that the first and the second targets are detected simultaneously.

The metal nanoparticle can include silver nanoparticles, gold nanoparticles, silver nanostars, gold nanostars, silver-coated gold nanostars, bimetallic nanoparticles, multi-metallic nanoparticles, dielectric nanoparticle cores covered with metal nanoshells, or multi-nanoparticle structures.

In the method, the contacting of the nanoprobe and the target can occur in vivo. The target nucleic acid can be a mRNA in a subject such as, for example, a human or an animal, and the placeholder nucleic acid can be siRNA such that the subject is treated with mRNA interference therapy.

The target nucleic acid can be a microRNA in a subject such as, for example, a human or an animal, and the placeholder nucleic acid can be an anti-microRNA such that the subject is treated with microRNA interference therapy.

The metal nanoparticle can include a NIPAM protective coating. The metal nanoparticle can be embedded in a hollow silica shell. The target nucleic acid can be in a subject such as, for example, a human or an animal, and the nanoprobe can have a coating that includes a drug for release upon a change in temperature or pH such that the subject is treated with the drug upon the change in the temperature or the pH.

In one embodiment, a method is provided for detecting protein and small molecule targets, comprising: contacting a nanoprobe directed to a protein target or a small molecule target with the target under conditions suitable for the nanoprobe to bind to the target, wherein the nanoprobe comprises: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; a placeholder aptamer bound to the placeholder binding sequence such that formation of the hairpin structure is prevented, wherein the placeholder aptamer is capable of binding to the target; and an optical label attached to the oligonucleotide, irradiating the sample with electromagnetic radiation from an excitation source; and detecting the electromagnetic radiation originated by the label, wherein a level of electromagnetic radiation originated by the label in the presence of the target is changed due to movement of the label into the vicinity of the nanoparticle electromagnetic enhancement upon formation of the hairpin structure. The protein target can be present on the surface of a cell such that detecting the protein results in detection of the cell. The cell can include a cancer cell.

It has been reported that the electromagnetic field (EM) is particularly strong in the interstitial space between metal nanoparticles [Ref: Xu, H. X.; Aizpurua, J.; Kall, M.; Apell, P., *Physical Review E* 2000, 62 (3), 4318-4324.] The anomalously strong Raman signal originates from "hot spots", i.e., regions where clusters of several closely-spaced nanoparticles are concentrated in a small volume. This effect, also referred to as interparticle coupling or plasmonic coupling in a network of NPs, can provide a further enhancement effect besides the enhancement from individual particles. In previous work, computation of the electric field in the gaps between two spheres and between two spheroids over a range of frequencies also indicate the occurrence of very large field enhancements [Ref: Norton, S. J.; Vo-Dinh, T., *Journal of the Optical Society of America A—Optics Image Science and Vision* 2008, 25 (11), 2767-2775]. While very large enhancement for a single hot spot can be achieved in such structures, the presence and location of such hotspots is not predictable and the density of the hotspots tends to be very low. It is widely believed that SERS hot spots are created at locations where the EM field is strongly concentrated by the metallic nanostructures or between nanostructures. Creating a high density of such hot spots calls for a systematic study in periodic nanostructures made out of metals.

To further underline the inter-particle plasmonic coupling effect, the EM field has been investigated at the hot spot between two nanoparticles (solid nanospheres or nanoshells) [T. Vo-Dinh, A. Dhawan, S. J. Norton, C. G. Khoury, H-N. Wang, V. Misra, and M. Gerhold, "*Plasmonic Nanoparticles and Nanowires: Design, Fabrication and Application in Sensing*" *J. Phys. Chem. C,* 114 (16), pp 7480-7488 (2010)]. The theoretical investigations dealt with dimers of nanoparticles and nanoshells using a semi-analytical method based on a multipole expansion (ME) and the finite-element method (FEM) in order to determine the electromagnetic enhancement, especially at the interface areas of two adjacent nanoparticles. Two types of dimmers are considered, one comprised of two solid nanospheres and the other of two nanoshells. Nanoshells have been previously investigated and developed for medical applications. The maximum electric-field enhancement in the gap between the particles occurs when the electric field of the incident light is polarized along the dimer axis. The calculations of the electric field were compared at a point in the gap midway between the two particles (solid sphere or shell) using two different numerical methods. The first calculation was performed using the FEM-based commercial software package COMSOL Multiphysics and the second was a semi-analytical solution based on a multipole expansion (ME) of the fields. In the latter approach, the quasi-static approximation was employed, which significantly simplified the ME analysis, but is known to give accurate results when the particle size is about a tenth of a wavelength or less. Comparing the FEM results to those of the ME method demonstrated that in this size range the quasi-static assumption is an excellent approximation. The quasi-static approximation also has the virtue of being computationally very fast as well as relatively simple to program.

Field calculations were performed using both the FEM and ME methods for two types of dimers: a pair of solid nanospheres and a pair of nanoshells. In all cases, the outer diameter of the particles was assumed to be 20 nm with a particle gap of 5 nm. In the first calculation, the magnitude of the electric field in the gap midway between the particles was computed over a wavelength range from 300 nm to 800 nm. Three particular cases were considered: a dimer whose particles are nanoshells with a shell thickness of 15% and 35% of the outer shell radius, and a dimer whose particles are solid spheres. For a pair of silver nanospheres with a 2% gap, the results showed an electric field enhancement in the gap of over 700 at the peak of the plasmon resonance. In SERS measurements, the total signal is approximately proportional to the fourth power of the electric field magnitude, giving a total SERS enhancement of over $4 \times 10^{10}$. The results underline the very strong inter-particle plasmonic coupling effect [T. Vo-Dinh, A. Dhawan, S. J. Norton, C. G. Khoury, H-N. Wang, V. Misra, and M. Gerhold, *"Plasmonic Nanopartides and Nanowires: Design, Fabrication and Application in Sensing"*, *J. Phys. Chem. C,* 114 (16), pp 7480-7488 (2010)].

Figure 7B:
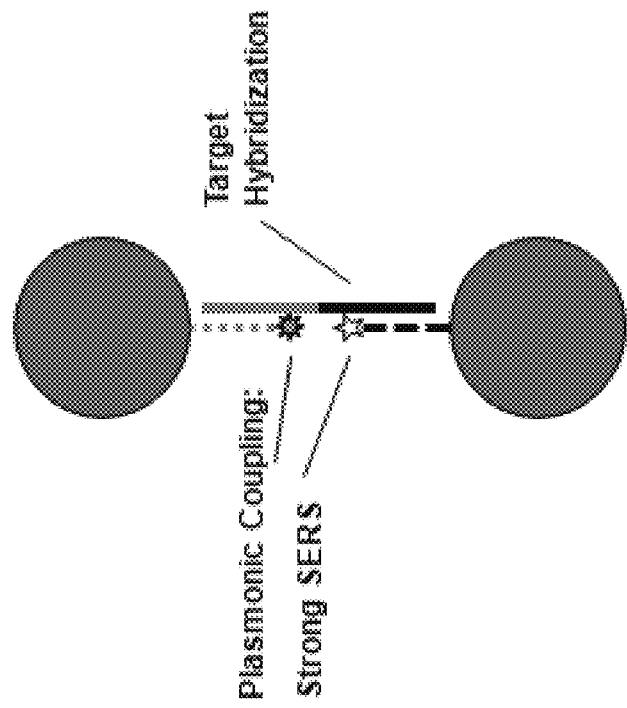
FIGS. 7A-7B are schematic diagrams illustrating the plasmonic nanoprobe for detection of nucleic acid targets according to embodiments of the present disclosure.
Figure 7A:
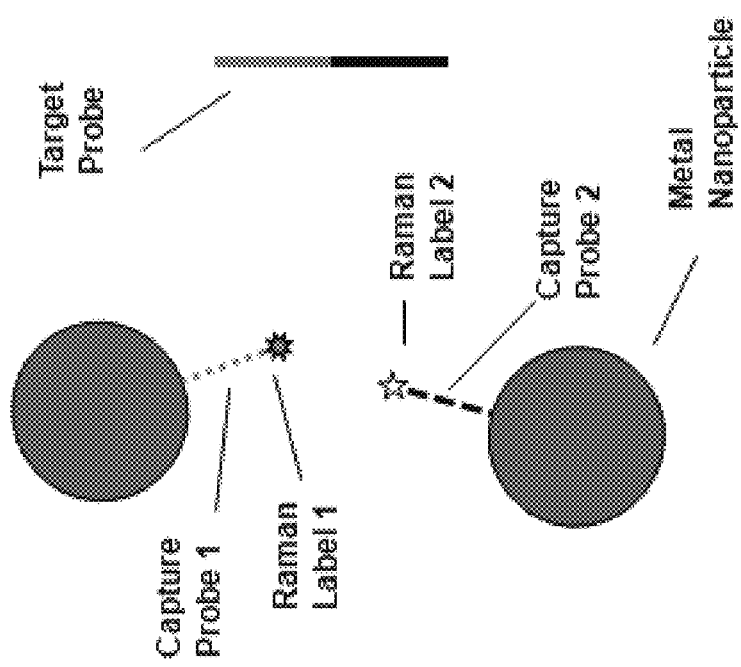

In one embodiment, the present disclosure provides plasmonics-active nanoprobes for nucleic acid targets. FIGS. 7A and 7B illustrate the plasmonic coupling detection concept for nucleic acid targets. FIG. 7A illustrates two plasmonics-active metal (e.g, silver or gold) nanoparticles (NPs), each having a separate olionucleotide probe sequence (which is also referred to herein as a "capture probe" or "capture probe DNA") represented by broken lines in a lighter and darker shade of grey in FIGS. 7A-7B. The first probe DNA on the first NP has a sequence identical to half of a target sequence of interest and has a first Raman label bound at the end of the probe. The second probe DNA on the second NP has a sequence identical to the other half of the target sequence of interest and has a second Raman label bound at the end of the probe.

When the first and second NPs are mixed with the target sequence, they hybridize to the target probe in such a way that the SERS labels are in the middle (FIG. 7B). As a result, the two Raman labels are "trapped" between the two metal nanoparticles. Due to the interparticle plasmonics coupling described above, upon excitation of the label molecules (e.g., using a laser or other appropriate energy source), the electromagnetic enhancement of the Raman signal is very intense, leading to extremely strong SERS signals of the two Raman label (FIG. 7B). The increase of the SERS signal intensities of the two Raman labels can be used as a to monitor and quantitatively detect the target nucleic acid sequence (e.g., DNA, RNA, microRNA, siRNA).

In one embodiment, a method is provided for detecting nucleic acid targets, comprising: contacting a first and a second nanoprobe directed to a nucleic acid target with the target under conditions suitable for the target to hybridize with the nanoprobes, wherein the first and the second nanoprobes comprise: at least one metal nanoparticle; an oligonucleotide probe attached at one end to the nanoparticle, the probe of the first nanoprobe including a sequence that is complementary to a first half of the target and the probe of the second nanoprobe including a sequence that is complementary to a second half of the target; and a first label attached to the first probe and a separate second label attached to the second probe, irradiating the sample with electromagnetic radiation from an excitation source; and detecting the electromagnetic radiation originated by both of the first and second labels, wherein a level of electromagnetic radiation originated by the labels in the presence of the target is changed upon hybridization of the probes with the target due to movement of the labels in between the nanoparticles.

In one embodiment, a pair of nanoprobes are provided for detecting nucleic acid targets, each of a first and a second nanoprobe comprising: at least one metal nanoparticle; an oligonucleotide probe attached at one end to the nanoparticle, the probe of the first nanoprobe including a sequence that is complementary to a first half of a target and the probe of the second nanoprobe including a sequence that is complementary to a second half of the target; and a first label attached to the first probe and a separate second label attached to the second probe.

Figure 8A:
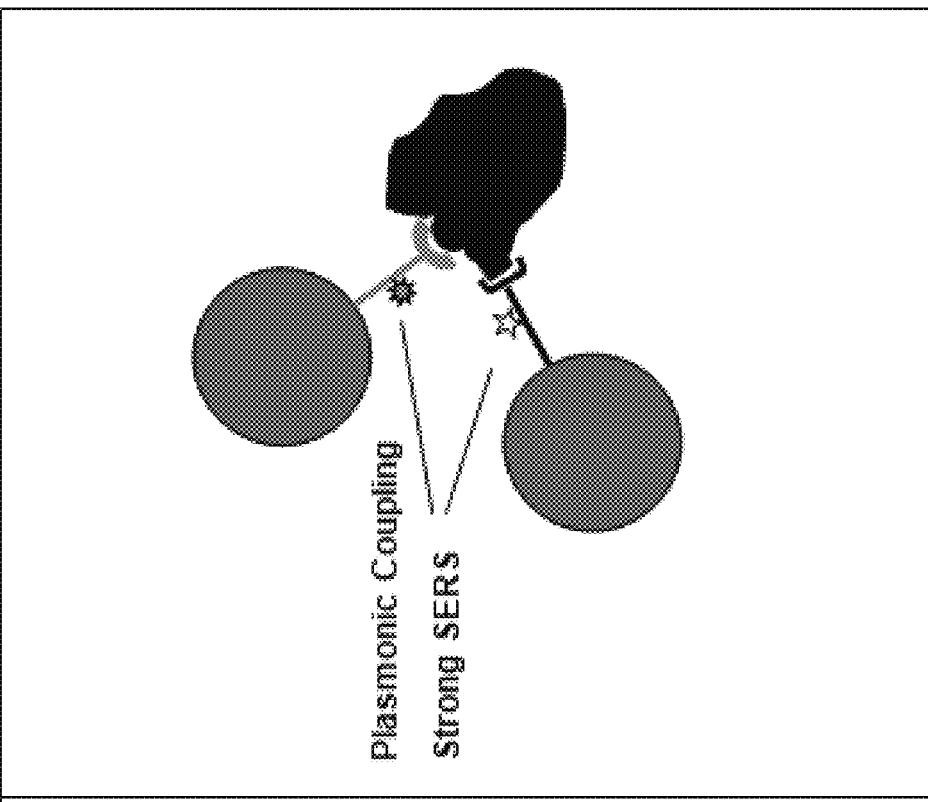
FIGS. 8A-8B are schematic diagrams illustrating the plasmonic nanoprobe for detection of protein targets according to embodiments of the present disclosure.
Figure 8B:
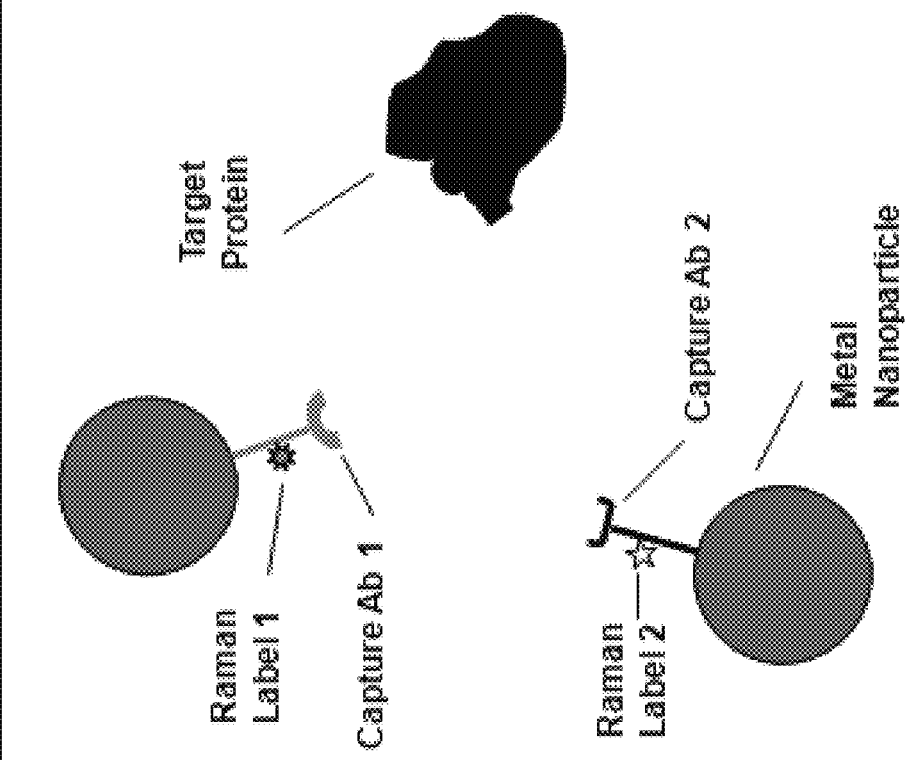

In one embodiment, the present disclosure provides plasmonics-active nanoprobes for protein targets. FIGS. 8A and 8B illustrate the plasmonic coupling detection concept for protein targets. FIG. 8A illustrates two plasmonics-active metal (e.g, silver or gold) nanoprobes, each having a different attached bioreceptor. In one example, the first bioreceptor can be an antibody that binds to a first site on a protein and the second bioreceptor can be an antibody that binds to a second site on the same protein. In another example, the first and second bioreceptors can bind to a protein on the surface of a cell such as a cancer cell. The two bioreceptors are represented by lighter and darker shades of grey as well as different shapes in FIGS. 8A-8B. The first nanoprobe has a first Raman label attached to the first bioreceptor and the second nanoprobe has a second Raman label bound to the second bioreceptor.

When the first and second nanoprobes are mixed with the target protein (or cancer cell having the target protein on the surface), the bioreceptor binding to the target brings the two Raman labels in between the two nanoparticles of each of the nanoprobes (FIG. 8B). As a result the two Raman labels are "rapped" between the two metal nanoparticles. Due to the interparticle plasmonics coupling described herein above, upon excitation of the labels (e.g., using a laser or other appropriate energy source), the electromagnetic enhancement of the Raman signal is very intense, leading to extremely strong SERS signals for the two Raman labels (FIG. 8B). The increase of the SERS signal intensities of the two Raman labels can be used to monitor and quantitatively detect the protein target.

In one embodiment, a method is provided for detecting protein targets, comprising: contacting a first and a second nanoprobe directed to a protein target with the target under conditions suitable for the nanoprobes to bind to the target, wherein the first and the second nanoprobes comprise: at least one metal nanoparticle; a bioreceptor attached to the nanoparticles, the bioreceptor of the first nanoprobe capable of binding to a first site on the protein target and the bioreceptor of the second nanoprobe capable of binding to a second site on the protein target; and a first label attached to the first bioreceptor and a separate second label attached to the second bioreceptor, irradiating the sample with electromagnetic radiation from an excitation source; and detecting the electromagnetic radiation originated by both of the first and second labels, wherein a level of electromagnetic radiation originated by the labels in the presence of the target is changed upon binding of each of the bioreceptors to the target due to movement of the labels in between the nanoparticles.

In one embodiment, a pair of nanoprobes are provided for detecting protein targets, each of a first and a second nanoprobe comprising: at least one metal nanoparticle; a bioreceptor attached to the nanoparticle, the bioreceptor of the first nanoprobe capable of binding to a first site on a protein target and the bioreceptor of the second nanoprobe capable of binding to a second site on the protein target; and a first label attached to the first bioreceptor and a separate second label attached to the second bioreceptor.

FIG. 9 depicts an alternative embodiment of the nanoprobe for detecting protein targets. As shown in FIG. 8, nanoparticles can be labeled with a SERS dye and functionalized with a ligand that binds to a protein target of interest. The intracellular environment causes nanoparticles to self assemble into closely packed arrays. This generates many "hot-spots" of electromagnetic field enhancement between neighboring particles, and thus high SERS from the dye label. Interaction of the targeting ligand (aptamer, nucleic acid, antibody) with the target increases the effective diameter of the nanoparticle probe, spacing the metal nanoparticle cores further apart. This results in a reduction of the "hot-spots" and a decrease in the SERS signal emitted from the dye label. Ideally, as the SERS from the label decreases, a new SERS signal from the target can also be observed.

In one embodiment, a method is provided for detecting protein targets, comprising: contacting a nanoprobe comprising: at least one metal nanoparticle; a ligand attached to the nanoparticle capable of binding to a protein target; and an optical label attached to the nanoparticle, with the target under conditions suitable for both the nanoprobe to bind to the target and for the nanoparticles to self assemble into closely packed arrays in the absence of the target such that electromagnetic field enhancement occurs between neighboring nanoparticles, irradiating the sample with electromagnetic radiation from an excitation source; and detecting the electromagnetic radiation originated by the label, wherein a level of electromagnetic radiation originated by the label is decreased upon binding of the ligand to the target due to movement of the metal nanoparticles further apart such that the label is less affected by electromagnetic field enhancement between neighboring nanoparticles.

In one embodiment, a nanoprobe is provided for detecting protein targets, comprising: at least one metal nanoparticle; a ligand attached to the nanoparticle capable of binding to a protein target; and an optical label attached to the nanoparticle.

The protein target can be present on the surface of a cell such that detecting the protein results in detection of the cell. The cell can include a cancer cell.

In one embodiment, the present disclosure provides plasmonics-active nanoprobes. Plasmon resonances arise within a metallic nanoparticle from the collective oscillation of free electrons driven by an incident optical field. The plasmonic response of nanoparticles has played a role in a growing number of applications, including surface-enhanced Raman scattering (SERS), chemical sensing, drug delivery, photothermal cancer therapy, new photonic devices, biological analysis and medical diagnostics. The plasmonics-active metal nanostructures include nanoparticles and semi-nanoshells consisting of a layer of nanoparticles coated by silver on one side (nanocaps or half-shells). Several groups have shown that plasmon resonances of spherical shells can be tuned by controlling the shell thickness [M. M. Kerker, *Acc. Chem. Res.*, 17, 370 (1984); J. B. Jackson, S. L. Westcott, L. R. Hirsch, J. L. West and N. H. Halas, "Controlling the surface enhanced Raman effect via the nanoshell geometry," *Appl. Phys. Lett.*, vol. 82, 257-259, 2003]. These shells consist typically of a metallic layer over a dielectric core. The analysis has been extended to spheroidal shells and shows how plasmon resonances (both longitudinal and transverse modes) are influenced by both shell thickness and aspect ratio. A number of researchers have examined the plasmonic response of the solid spheroidal particle in their analysis of surface-enhanced Raman scattering, although the spheroidal shell appears not to have been investigated. Prolate and oblate spheroidal shells have been investigated and show interesting qualitative features in their plasmon resonances. Results indicate that the spheroidal shell presents two degrees of freedom for tuning: the shell thickness and the shell aspect ratio [S. J. Norton and T. Vo-Dinh, "*Plasmonic Resonances of Nanoshells of Spheroidal Shape*", IEEE Trans. Nanotechnology, 6, 627-638 (2007)]. It has been shown that nanostar-shaped structures can also be plasmonics-active and induce strong SERS signals.

FIGS. 10A-10J are schematic diagrams showing the various embodiments of plasmonics-active nanoparticles of the present disclosure: A) Metal nanoparticle; B) Dielectric nanoparticle core covered with metal nanocap; C) Spherical metal nanoshell covering dielectric spheroid core; D) Oblate metal nanoshell covering dielectric spheroid core; E) Metal nanoparticle core covered with dielectric nanoshell; F) Metal nanoshell with protective coating layer; G) Multi layer metal nanoshells covering dielectric spheroid core; H) Multi-nanoparticle structures; I) Metal nanocube and nano-triangle/nanoprism; and J) Metal cylinder.

Figure 11:
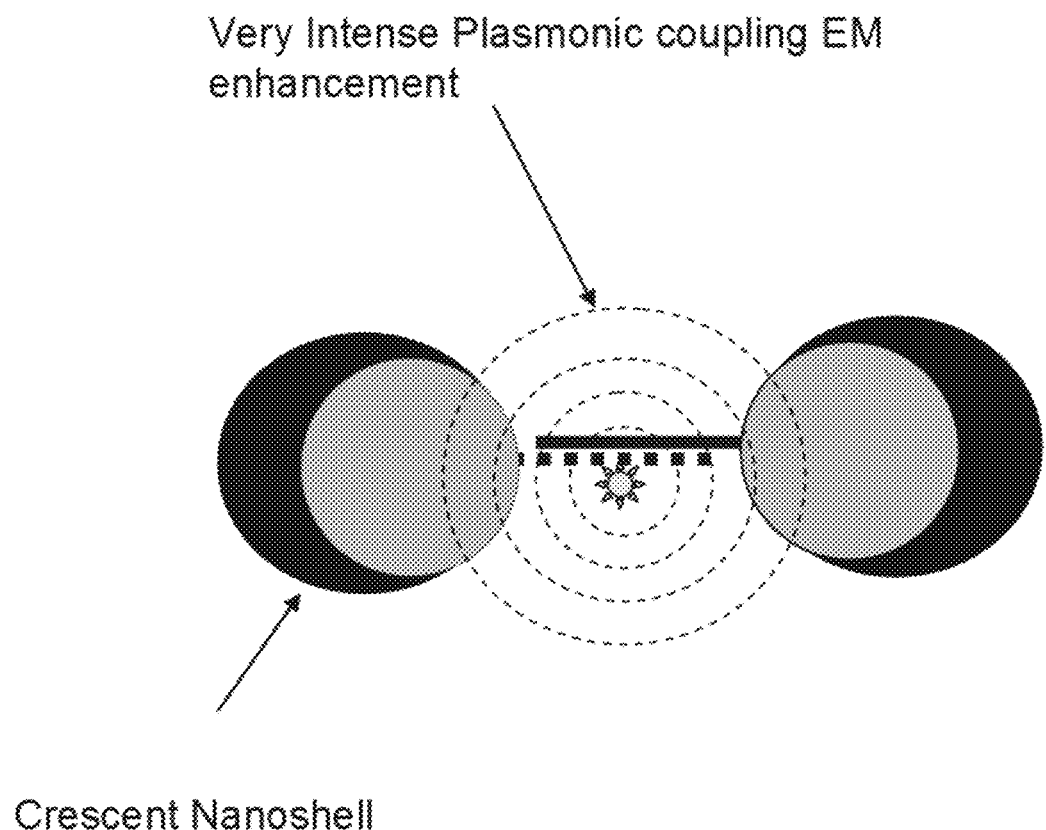
FIG. 11 is a schematic diagram showing the enhanced plasmonic coupling in crescent metal nanoparticles according to FIG. 10B.

FIG. 11 shows an embodiment where the plasmonics nanoparticles have a "crescent structure" partially covering a dielectric core (e.g., silica, polymeric material, etc.). The side of the crescent end produces extremely strong plasmonics enhancement. Furthermore the plasmonic coupling between these crescent-induced enhancements can produce a combined and very strong coupling effect.

The nanoprobes of the present disclosure can be prepared using either silver (or gold) nanoparticle colloids. Gold nanoshells can be fabricated using published methods using a mechanism involving nucleation and then successive growth of gold nanoparticles around a silica dielectric core. In addition, the nanoprobes can include use of nanospheres spin-coated on a solid support in order to produce and control the desired roughness. The nanostructured support can be subsequently covered with a layer of silver that provides the conduction electrons required for the surface plasmon mechanisms. Among the techniques based on solid substrates, the methods can include using simple nanomaterials, such as Teflon or latex nanospheres. Teflon and latex nanospheres are commercially available in a wide variety of sizes. The shapes of these materials are very regular and their size can be selected for optimal enhancement. These materials can consist of isolated dielectric nanospheres (30-nm diameter) coated with silver producing systems of half-nanoshells, referred to as nanocaps. The nanocaps can be 300-nm diameter polymer nanospheres covered by a 100-nm thick silver nanocap (half-nanoshell) coating. The nanoparticles can be sonicated to release them from the underlying substrate. The effect of the sphere size and metal layer thickness upon the SERS effect can be easily investigated. By rotating the platform supporting the nanospheres, one can extend the solver coverage and produce the "crescent structures" shown in FIG. 11. The silver coated nanospheres were found to be among the most plasmonics-active investigated. Gold can also be used instead of silver to coat over nanoparticle materials.

In one embodiment, a silver-coated gold nanostar is provided resulting from a process comprising reducing aqueous silver ($Ag^+$) to solid silver ($Ag^0$) onto gold nanostar seeds under conditions such that the silver-coated gold nanostars are produced.

In one embodiment, a nanoprobe is provided comprising: a silver-coated gold nanostar resulting from a process comprising reducing aqueous silver ($Ag^+$) to solid silver ($Ag^0$) onto gold nanostar seeds under conditions such that the silver-coated gold nanostars are produced; and an optical label capable of absorbing electromagnetic radiation originated as a result of excitation of the nanostar with excitation radiation.

Known methods can be employed to immobilize the bioreceptors to metal nanoparticles to prepare the nanoprobes of the present disclosure. By "bioreceptor" is meant the nucleic acid stem of the iMS nanoprobes of the present disclosure as well as the "bioreceptor" on the nanoprobes for detecting proteins shown in FIGS. 8 and 9 that can be amino acid based. The immobilization of biomolecules (such as, e.g., DNA, RNA, LNA, proteins, antibodies, etc.) to a solid support can use a wide variety of methods published in the literature. Binding can be performed through covalent bonds usually takes advantage of reactive groups such as amine (—NH$_2$) or sulfide (—SH) that naturally are present or can be incorporated into the biomolecule structure. Amines can react with carboxylic acid or ester moieties in high yield to form stable amide bonds. Thiols can participate in maleimide coupling, yielding stable dialkylsulfides.

A solid support of interest is gold (or silver) nanoparticles. The majority of immobilization schemes involving Au (Ag) surfaces utilize a prior derivatization of the surface with akylthiols, forming stable linkages. Alkylthiols readily form self-assembled monolayers (SAM) onto silver surfaces in micromolar concentrations. The terminus of the akylthiol chain can be used to bind biomolecules, or can be easily modified to do so. The length of the akyithiol chain has been found to be an important parameter, keeping the biomolecules away from the surface. Furthermore, to avoid direct, non-specific DNA adsorption onto the surface, alkylthiols can be used to block further access to the surface, allowing only covalent immobilization through the linker [Steel, A. B.; Herne, T. M.; Tarlov, M. J. Anal. Chem. 1998, 70, 4670-7; Herne, T. M.; Tarlov, M. J. J. Am. Chem. Soc. 1997, 119, 8916-20].

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6]. After SAM formation on gold/silver nanoparticles, akyfthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include:

Binding Procedure Using N-Hydroxysuccinimide (NHS) and its Derivatives.

The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [Boncheva, M.; Scheibler, L.; Lincoln, P.; Vogel, H.; Akerman, B. Langmuir 1999, 15, 4317-20]. NHS reacts almost exclusively with primary amine groups. Covalent immobilization can be achieved in as little as 30 minutes. Since H$_2$O competes with —NH$_2$ in reactions involving these very labile esters, it is important to consider the hydrolysis kinetics of the available esters used in this type of coupling. The derivative of NHS O—(N-succinimidyl)-N,N,N',N'-tetramethyluronium tetrafluoroborate, increase the coupling yield by utilizing a leaving group that is converted to urea during the carboxylic acid activation, hence favorably increasing the negative enthalpy of the reaction.

Binding Procedure Using Maleimide.

Maleimide can be used to immobilize biomolecules through available —SH moieties. Coupling schemes with maleimide have been proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfydryl groups is an alternative for biomolecules lacking them. Free sulfhydryls are immobilized to the maleimide surface by an addition reaction to unsaturated carbon-carbon bonds [Jordan, C. E., et al., 1997].

Binding Procedure Using Carbodiimide.

Surfaces modified with mercaptoaikyldiols can be activated with 1,1'-carbonyldiimidazole (CDI) to form a carbonylimidazole intermediate. A biomolecule with an available amine group displaces the imidazole to form a carbamate linkage to the akylthiol tethered to the surface [Potyrailo, R. A., et al., 1998].

In one embodiment, the present disclosure provides plasmonic nanoparticle biosensors with anti-biofouling properties. Biofouling is one of the most critical factors to consider for in vive nanosensors. Therefore, for in vive use of the nanosensors of the present disclosure, an anti-biofouling layer can be designed to protect nanoparticle-based nanosensors. Poly(ethylene glycol) (PEG) coating has been used to protect a wide variety of nanoprobes. One advantageof PEG is that PEG can prevent formation of the hair-pin loop structure. However, because the PEG layer is also degraded over time, it is not a good choice for long-term (e.g., up to 1 month) anti-biofouling.

Figure 12:
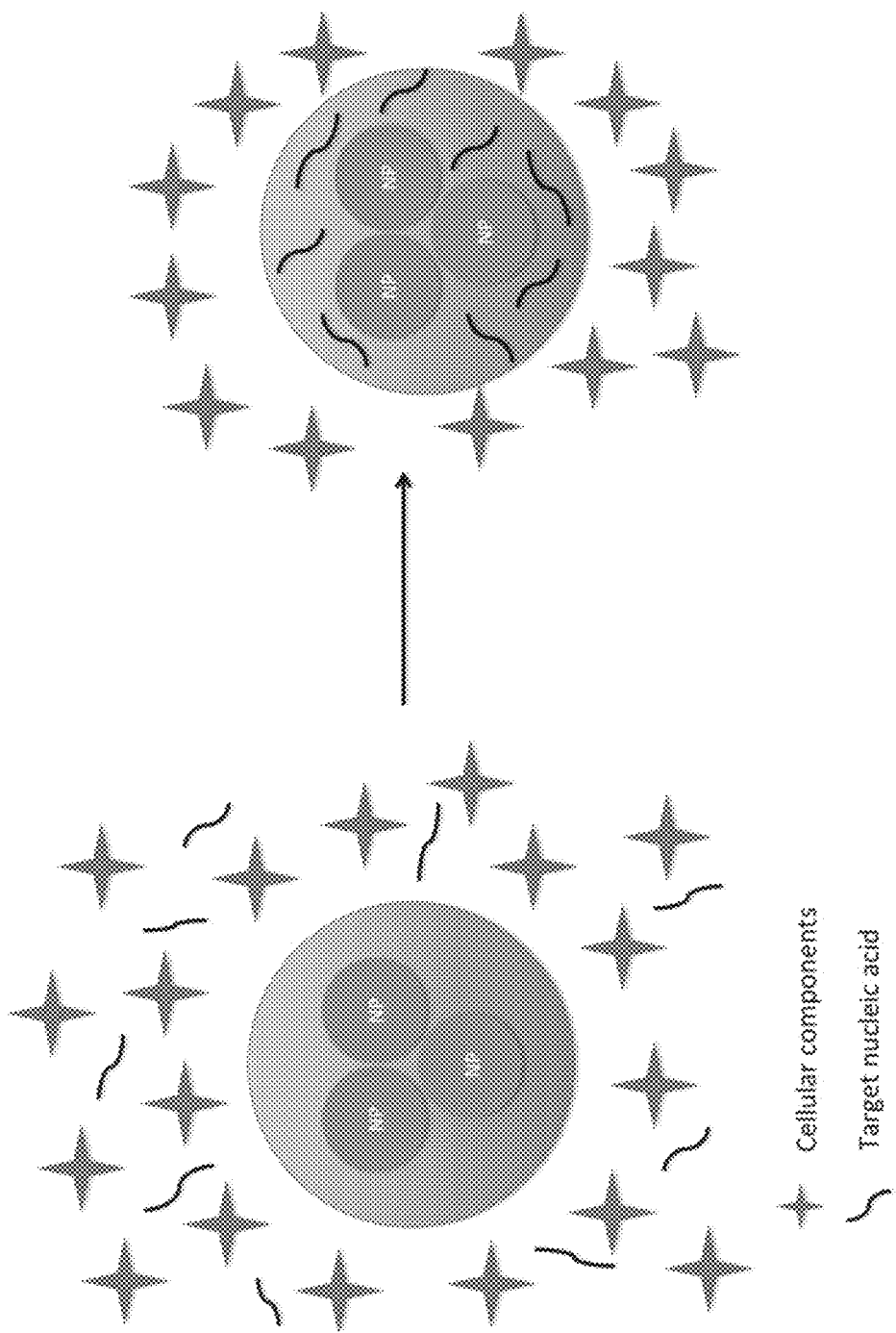
FIG. 12 is a schematic diagram illustrating plasmonic nanoprobes protected with an anti-biofouling layer made of NIPAM according to embodiments of the present disclosure. The star shape represents cellular components and the wavy line represents target nucleic acid molecules.

Therefore, another 'porous' biomaterial is herein provided for anti-biofouling protection of the nanosensors of the present disclosure. The porous biomaterial provided can be N-Isopropylacrylamide (NIPAM), which can act as an anti-biofouling layer but also allows small molecules to diffuse in to react with the nanosensors (FIG. 12). The NIPAM shell acts as a molecular sieve that can block the large cellular compounds (e.g. blood cells, albumin, etc.) but allow for the diffusion of the target nucleic acid. NIPAM shells have been shown to act as a molecular sieve, excluding any molecules larger than the pore sizes of the membrane. Pore size can be controlled by using a copolymer such as N,N'-Methylenebisacrylamide. With such a shell, immune cells and blood cells can be excluded from interacting with the nanosensors. Small molecules, such as mRNA, can diffuse through the capsule and react with the nanosensors. Encapsulation of the biosensors of the present disclosure with NIPAM can provide a robust nanosensing platform for use in living organisms.

Additional anti-biofouling strategies are provided that can be used to retain nanoprobe functionality in a biological environment. One method is to use thiol-PEG brushes to prevent protein adsorption on the particle surface. The thiol group binds strongly to the nanoparticle surface and can not be easily removed. Adding a small amount of thiol-PEG to the nanostar solution is sufficient for functionalization. Variation of brush density and length can be optimized so that little to no impact on sensor functionality is observed. Another anti-biofouling method involves the use of pNIPAM brushes. Functionalization can be performed in the same manner as the thiol-PEG, but in this case it is an amine group that is attracted to the gold or silver surface. The loading density and chain length of the pNIPAM brushes can be optimized in a similar manner to the thiol-PEG. The pNIPAM brush functionalized nanoparticles can be further protected by crosslinking the brushes with a copolymer to form a pNIPAM shell. The pore size within the shell can be controlled by varying the type of crosslinker and its amount.

This pNIPAM shell then acts as a molecular sieve, and pore size can be tuned depending on the analyte of interest.

Figure 13:
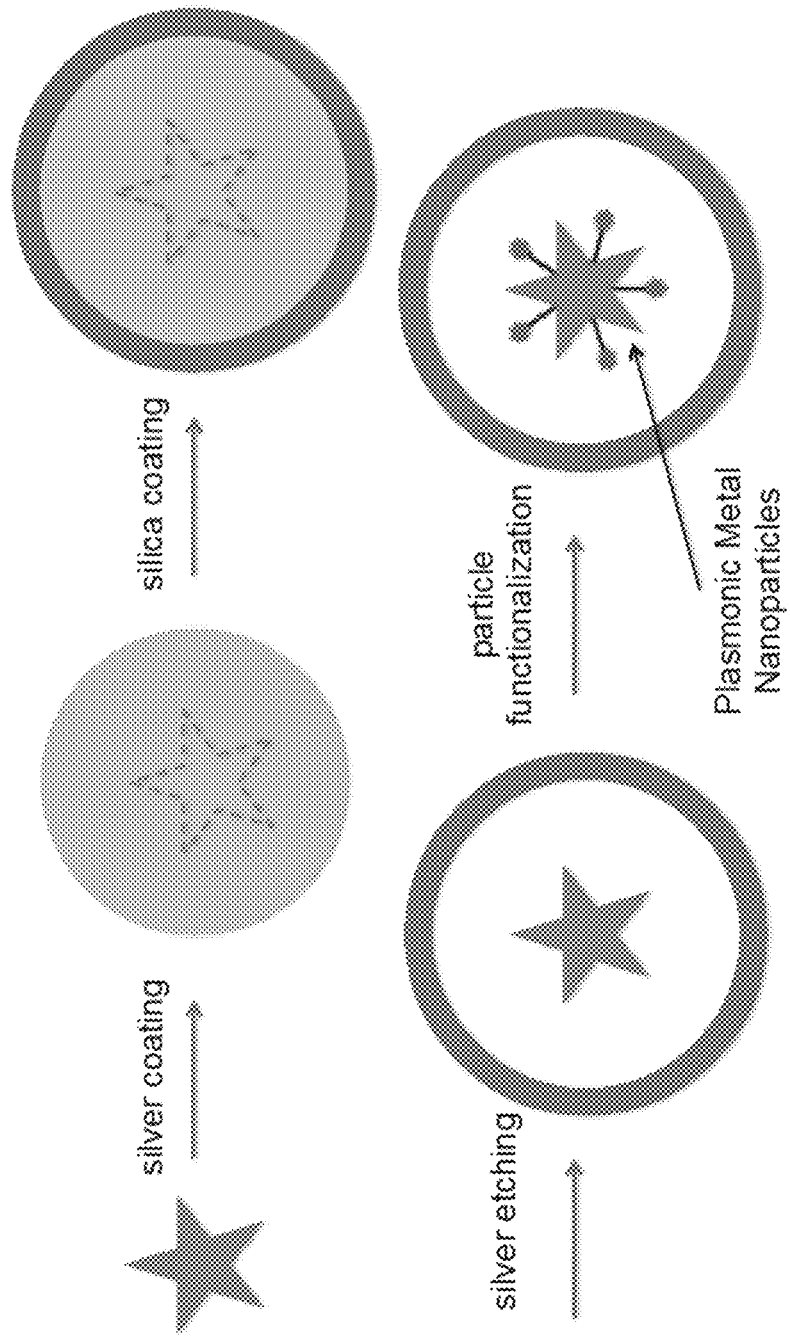
FIG. 13 is a schematic diagram showing preparation of plasmonic metal nanoparticles within a hollow silica shell according to embodiments of the present disclosure.

Silica coatings can also be used to protect the nanoprobe for sensing in complex environments. A mesoporous silica shell with tunable pore size can protect the nanosensor from interference, while allowing enough space for the nanoprobe to still operate. The nanorattle, or nanoparticle encapsulated within a hollow silica shell, is also a viable option to prevent biofouling. In one example of creating such a structure, gold nanostars can be coated with a spherical silver shell, and then a porous silica shell. Etching away the silver using $H_2O_2$ results in a nanostar within a hollow silica shell (FIG. 13).

Figure 14:
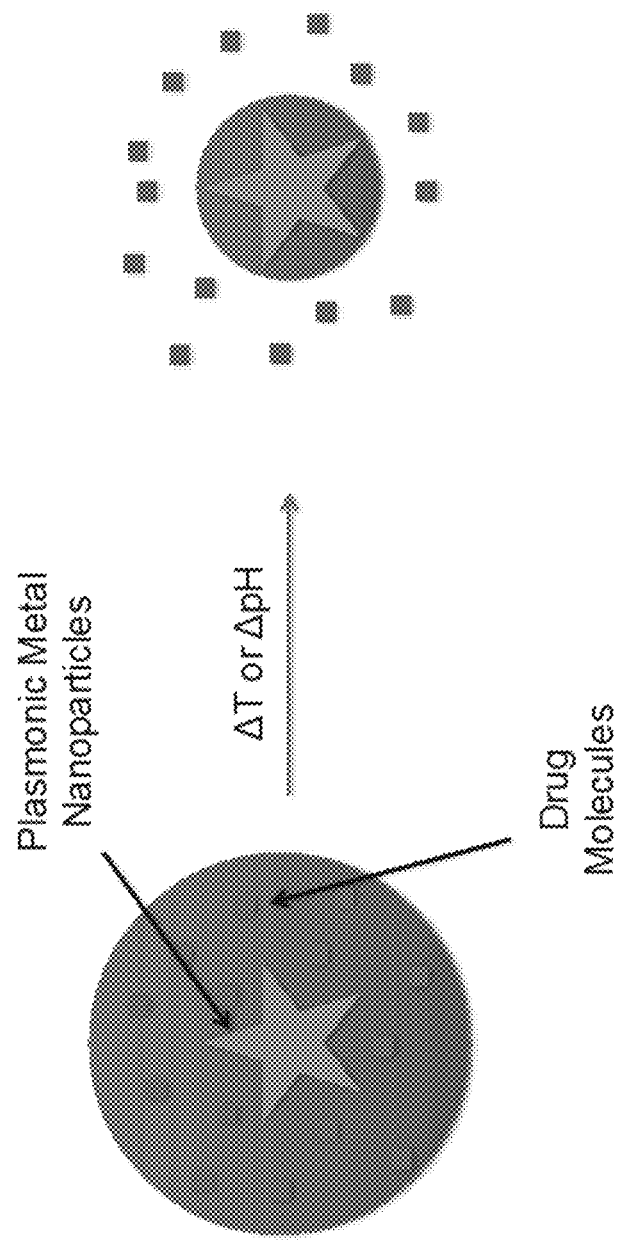
FIG. 14 is a schematic diagram showing release of drug molecules by a change in temperature or pH from plasmonic metal nanoparticles having a NIPAM shell according to embodiments of the present disclosure.

In another embodiment, the nanoprobes having a NIPAM shell as described above can be designed as drug carriers where a change in temperature or pH triggers drug release from the NIPAM shell (FIG. 14). The temperature change can be intrinsic (due to body temperature change) or can be extrinsically triggered outside the body using, for example, microwave, radio-frequency, MR signal or light.

One of the advantages of Raman/SERS is the ability for multiplex detection. Employment of the SERS technique permits the use of many different probe molecules, allowing the narrow band spectral characteristics of Raman-based probes to be used to advantage for sensitive, specific analysis of microarrays. Multiple probes, each designed to detect a specific DNA target can be used and detected simultaneously using a multiplex detection system as described herein.

Figure 15:
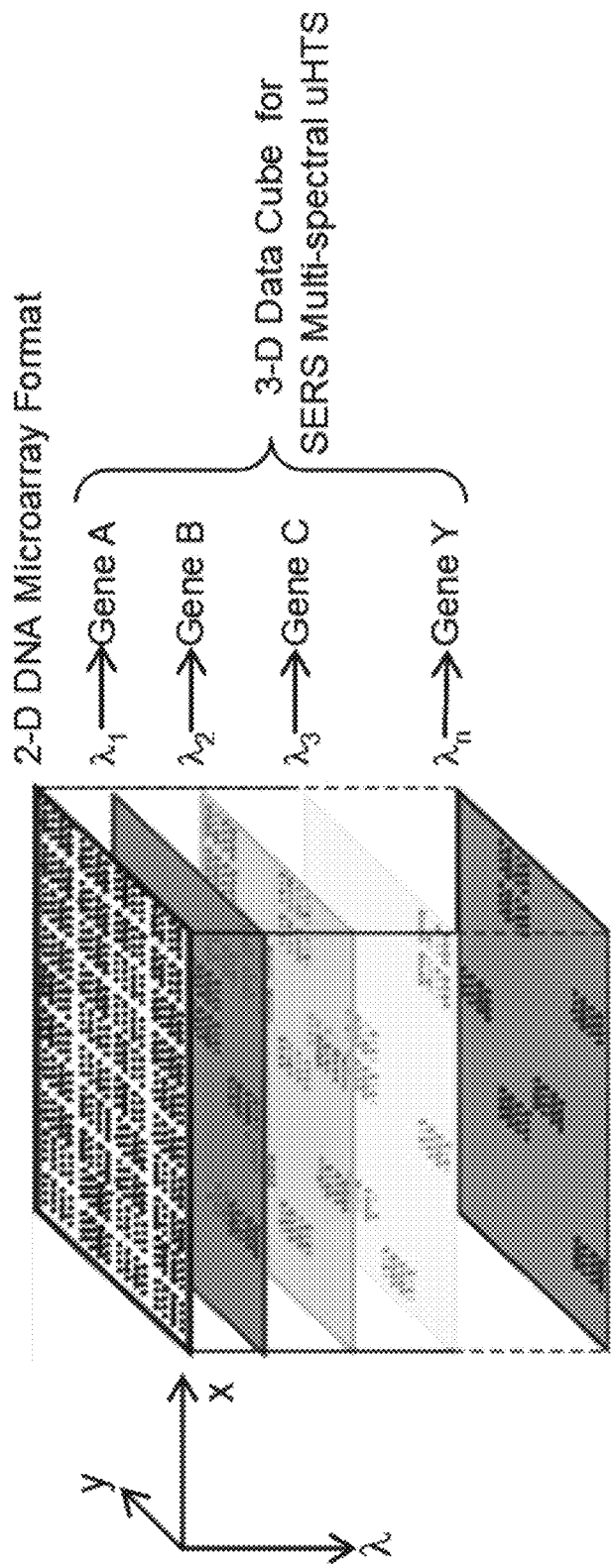
FIG. 15 is a schematic diagram showing a Raman data cube in multi-spectral imaging of a microarray for multiplex NPCI detection to simultaneously detect more than one target DNA in a solution according to embodiments of the present disclosure.

Raman spectroscopy can be used as a modality for detection in ultra-high throughput microarray systems. Using a multispectral Raman imaging system, the entire emission spectrum of multiple wavelengths (~10-100) can be collected on the entire image in the field of view. The resulting multispectral image can be presented as a 3-D data cube as shown in FIG. 15, consisting of two spatial dimensions (x, y) defining the image area of interest as well as wavelength ($\lambda$), as the third dimension indicated in the FIG. 15 on the Z axis.

Multiplex capability, which allows for monitoring of a large number of molecular processes simultaneously, is an important feature in systems biology research. A wide variety of luminescence labels (e.g., fluorescent labels, chemiluminescent labels, quantum dots, etc.) have previously been developed for bioassays. Although detection sensitivities achieved by luminescence techniques are adequate, the spectral overlap of the relatively large bandwidth of fluorescence spectra limit the number of labels that can be used simultaneously. Therefore, alternative techniques with improved multiplex capability are needed. Due to the narrow bandwidths of Raman bands, the multiplex capability of the SERS probes of the present disclosure is excellent in comparison to the other spectroscopic alternatives.

For comparison purposes, consider the detection of crystal fast violet (CFV) dye in fluorescence and SERS. The spectral bandwidth of CFV label in the fluorescence spectrum is relatively broad (approximately 50-60 nm halfwidth), whereas the bandwidth of the SERS spectrum of the same CFV label is much narrower (<0.5 nm or 3 cm$^{-1}$ halfwidth) (data note shown). In another example of the SERS advantage in "label multiplexing", HIV and Hepatitis C (HCV) gene sequences were simultaneously detected by acquiring SERS spectra of a mixture of a CFV-labeled HIV gene sequence and a BCB-labeled HCV gene sequence (data not shown). These results demonstrate the advantage of SERS as a practical tool for the identification and differentiation of multiple genes or gene expression in diagnostics or HTS applications.

The data also indicate that use of SERS can increase the multiplexing capability over currently used luminescence techniques by a factor of several orders of magnitude. In a typical Raman spectrum, a spectral interval of 3000 cm$^{-1}$ can provide 3000/3 or $10^3$ available individual spectral "intervals" at any given time. Even when allowing a deduction factor of 10 due to possible spectral overlaps, it should be possible to find 100 labels that can be used for labeling multiple probes simultaneously. This multiplex advantage is particularly useful in ultra-high-throughput analyses where multiple gene targets can be screened in a highly parallel multiplex modality. For example, a 10,000 ($10^4$) microarray can be labeled-multiplexed with 10-100 labels to provide a 3-D data cube of $10^5$-$10^6$ (one million) data.

A multiplex NPCI system primarily consists of an AOTF, an excitation laser, a long pass filter, and a detector. The basic system can be used to acquire images of samples at different wavelengths. To perform high throughput measurements, the RMS system can be coupled to an imaging optical system. A personal computer can be used to control a CCD, scan the RF signal applied to the AOTF, and perform data acquisition. The light emitted from the microarray platform can be collected by an imaging system, filtered by the AOTF, and then imaged onto a CCD. By changing the wavelength of the AOTF, a spectrum can be acquired as a series of images (one for each wavelength).

A $TeO_2$ AOTF purchased from Brimrose Corporation, Baltimore, MD (model TEAF 10-45-70-S) can be used. According to the manufacturer, the AOTF has an effective wavelength range of 450 nm to 700 nm (corresponding drive frequency 178-100 MHz). For visible wavelengths in a tellurium oxide crystal, the applied acoustic wave is RF and can be switched very quickly compared to other technologies. Unlike a liquid crystal tunable filter where the bandwidth is fixed by the design and construction, an AOTF can vary the bandwidth by using closely spaced RF simultaneously. The spectral resolution given by the manufacturer for the AOTF used in this study was 4 nm at 633 nm. The diffraction efficiency is relatively high, typically about 70% at 600 nm. The optical aperture is 10 by 10 mm and the acceptance angle is greater than 30°. The drive power range was 1.0 to 1.5 W. The RF generator used (Brimrose-model AT) could apply 0 to 10 W of RF power and is controlled by a DOS-based computer using a 16-bit computer controller board supplied by Brimrose.

The 2-D detection system uses an intensified CCD (Andor or Roper Scientific). The interface to the PC-compatible computer is accomplished via an RS232 system. The excitation source is a HeNe or a suitable diode laser. A CCD image of the emitted SERS is acquired and can serve as a map of gene expression (concentrations and distribution). By varying the bandpass of the AOTF, images can be acquired rapidly at selected wavelengths, enabling different gene expression to be screened. The 2-D detector is oriented 5.5° from the optical axis of the AOTF (due to the diffraction angle of the AOTF at a central wavelength: 550 nm). The AOTF is placed 30-cm from the 2D-detector to allow the separation of both the diffracted and reflection images and an iris will be placed in the optical path to block to undiffracted light. A long-pass filter can be placed flush against the iris to reject any remaining laser light that may have been scattered in the process of illumination. A glass lens (5 cm diameter) is used to collect the light and form an image on the CCD. The output end of the microarray platform is placed in the object plane of the lens. The lens systems is chosen to give a total magnification to match the 2-D detector.

Another advantage of the nanoprobe biosensors of the present disclosure is that they can be used for rapid in vitro diagnostics. For example, the color of a solution containing a nanoprobe biosensor of the present disclosure can change rapidly and visibly in the presence of the target of interest. As a result, the nanoprobes of the present disclosure can be used for rapid, simple and inexpensive detection. Such a test is appropriate for environmental sensing (e.g., detecting *E. coli* in waste streams) and global health (e.g., detecting infectious diseases) in underserved regions where access to sophisticated diagnostics facilities are not possible.

In one embodiment, a method is provided for detecting nucleic acid targets, comprising: contacting a nanoprobe directed to a nucleic acid target with the target under conditions suitable for the target to hybridize with the nanoprobe, wherein the nanoprobe comprises: at least one metal nanoparticle; an oligonucleotide attached at one end to the nanoparticle, the oligonucleotide including a stem-L and a stem-R sequence capable of hybridizing to form a hairpin structure and a placeholder binding sequence in between the stem-L and stem-R sequences; and a placeholder nucleic acid complementary to the placeholder binding sequence and complementary to the target, wherein the placeholder nucleic acid is hybridized to the placeholder sequence in the absence of the target such that formation of the hairpin structure is prevented; and detecting a color change in the presence of the target upon formation of the hairpin structure. The color change can be a visible color change.

In one embodiment, a method is provided for detecting nucleic acid targets, comprising: contacting a pair of nanoprobes having at least one metal nanoparticle and an oligonucleotide probe attached at one end to the nanoparticle, the probe of the first nanoprobe including a sequence that is complementary to a first half of a target and the probe of the second nanoprobe including a sequence that is complementary to a second half of the target, with a target under conditions suitable for the target to hybridize with the nanoprobes; and detecting a color change in the presence of the target upon hybridization of the probes with the target. The color change can be a visible color change.

In one embodiment, a method is provided for detecting nucleic acid targets, comprising: contacting a pair of nanoprobes having at least one metal nanoparticle and a bioreceptor attached to the nanoparticle, the bioreceptor of the first nanoprobe capable of binding to a first site on a protein target and the bioreceptor of the second nanoprobe capable of binding to a second site on the protein target, with a target under conditions suitable for the target to bind to the nanoprobes; and detecting a color change in the presence of the target upon binding of the bioreceptors to the target. The color change can be a visible color change.

In one embodiment, a method is provided for detecting nucleic acid targets, comprising: contacting a nanoprobe having at least one metal nanoparticle and a ligand attached to the nanoparticle capable of binding to a protein target, with a target under conditions suitable for the target to bind to the nanoprobe; and detecting a color change in the presence of the target upon binding of the ligand to the target. The color change can be a visible color change.

The nanosensors of the present disclosure can be used for in vivo diagnostics. FIGS. 16A-16B illustrate the use of the nanoprobes as an in vivo diagnostic. The nanoprobes can be used in this manner as a real time, permanent and continuous 'health monitor'. For example, the nanoprobes can be given to a person by injection using various methodologies including: 1) deposition under the skin to form a 'smart mole' that can monitor a target in tissue or in the blood stream (FIG. 16A); 2) nanoprobes having magnetic cores can be moved to and concentrated in an area suitable for detection; and 3) the nanoprobes can be attached to a biocompatible material inside the skin layer.

In one example the nanoprobes can be injected as a colloidal solution in which the nanoprobes are polymer-coated. The nanoprobes can be embedded into a NIPAM hydrogel implant. The implant can be placed immediately under the skin to allow for optical detection in situ. The porosity of the hydrogel allows for passage of the target, while excluding larger interfering molecules. In another example, the nanoparticles of the nanoprobes can be iron oxide-gold/silver core-shell particles and the nanoprobes can be embedded in a NIPAM shell. The superparamagneic iron oxide core can be used to concentrate the nanoprobes at a specific location in the body with a wearable magnet. Concentration of the nanoprobes at the skin surface allows for optical interrogation through the skin.

In one embodiment, the nanosensors can be used to detect the host response to various pathogens. Both the pathogenic nucleic acids as well as the host response can be detected. The detection can be performed in the cytosol of dermal cells. Nanosensors can be designed for detection of the human radical S-adenosyl methionine domain containing 2 (RSAD2) gene, which is involved in antiviral defense and is one of the most highly induced genes upon interferon stimulation or infection with various viruses, including human cytomegalovirus (HCMV), influenza virus, hepatilis C virus (HCV), dengue virus, alphaviruses, and retroviuses such as human immunodeficiency virus (HIV). The RSAD2 gene has emerged as a host-response biomarker for diagnosis of respiratory infections. In addition, nanosensors of the present disclosure can be prepared to detect critical pathogen biomarkers such as rlbE, fliC and mobA genes for *Escherichia coli* (*E. coli*) serotype O157:H7; mecA and femA genes for *Staphylococcus aureus* and *Staphylococcus epidermidis*; aroQ and 16S rRNA genes for *Erwinia herbicola*; protective antigen (PA) and anthrax toxin activator (atxA) genes for *Bacillus anthracis*.

Several diagnostics systems can be utilized, depending on the degree of miniaturization. For example, detection of the target can be performed using a portable Raman diagnostic system having excitation light source and an optical detector (FIG. 16B). An alternative diagnostic system can include a pocket-sized (or palm-sized) battery-operated Raman diagnostics system that is linked to the 'smart mole' by fiberoptics excitation and detection (FIG. 16B). The pocket-sized system can be operated remotely by an iPhone or similar device. Further miniaturization can shrink the size of the portable diagnostic system into the size of a 'wristwatch-sized' battery-operated Raman diagnostics device (FIG. 16B)

The nanoprobes and methods of use of the present disclosure are useful for a wide variety of applications based on DNA/RNA/protein detection including, but not limited to: biomedical applications, point-of-care diagnostics, food safety, environmental monitoring, industrial process sensing, quality control applications, biotechnology industrial control, quality control, global health, cancer research, heart disease diagnostics, homeland defense.

In addition to Raman and SERS, other photonic techniques can be used for excitation of the nanoprobes in the methods of the present disclosure. For example, other parts of the electromagnetic spectrum can be used for excitation, ranging from gamma rays and X rays throughout ultraviolet, visible, infrared, microwave and radio frequency energy.

The nanoprobes of the present disclosure can be integrated with biochip technology for proteomics and genomics applications. Rapid, simple, cost-effective medical devices for screening multiple medical diseases and infectious pathogens can be essential for early diagnosis and improved treatments of many illnesses. An important factor in medical diagnostics is rapid, selective, and sensitive detection of biochemical substances (such as, e.g., nucleic acids, proteins, metabolites, and nucleic acids), biological species or living systems (bacteria, virus or related components) at ultratrace levels in biological samples (such as, e.g., tissues, blood and other bodily fluids) or in vive in humans and animals using anti-biofouling schemes.

Figure 17:
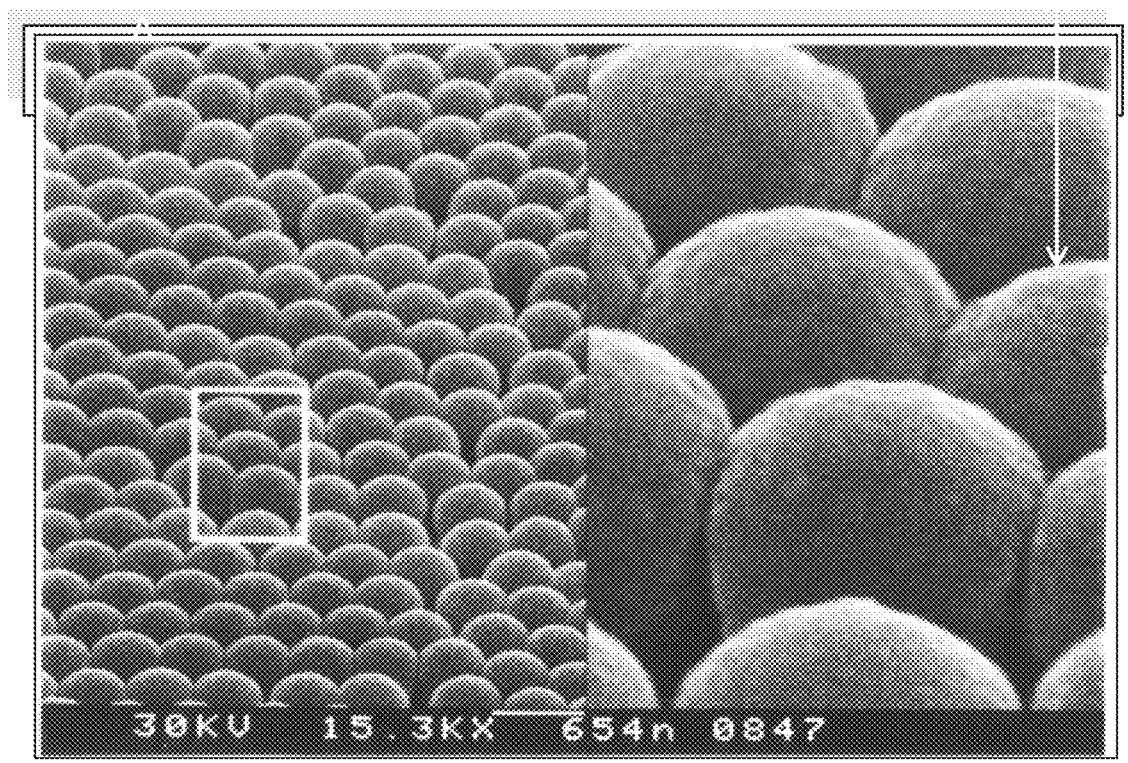
FIG. 17 is an SEM image of a plasmonics-active substrate comprising a close-packed array of nanospheres onto which a thin metal shell of silver or gold has been deposited according to embodiments of the present disclosure.

For example, the nanoprobes can be formed onto the surface of a plasmonics-active chip substrate. An example of chip substrate is a close-packed array of nanospheres onto which a thin metal shell of silver or gold has been deposited (FIG. 17). This chip substrate is an inexpensive, reproducible and effective plasmonics-active substrate that can be used for SERS studies requiring high detection sensitivity [T. Vo-Dinh, M. Y. K. Hiromoto, G. M. Begun, and R. L. Moody, "Surface-Enhanced Raman Spectroscopy for Trace Organic Analysis," Anal. Chem., 56: 1667 (1984); C. Khoury and T. Vo-Dinh, "Nanowave" Substrates for SERS: Fabrication and Numerical Analysis", J. Phys. Chem C, 116, 7534-7545 (2012)].

FIGS. 18A-18B are schematic diagrams illustrating the iMS-on-Chip system. In this case, the iMS hairpin nanoprobes are immobilized on a plasmonic-active substrate. The SERS signal is off as the iMS probes are in the "open" or "off" state in the presense of the capture probe (FIG. 18A). In the presence of target molecules, the capture probes are displaced by competitive hybridization and the SERS signal is turned on as the iMS probes are in the "closed" state (FIG. 18B).

The nanoprobes can be integrated onto a multi-functional biochip based on an integrated circuit photodiode array for use in medical diagnostics and pathogen detection. The biochip can be a self-contained device which allows simultaneous detection of various types of biotargets using different bioreceptors (e.g., antibodies, nucleic acids, enzymes, cellular probes) on a single system. The biochip sensor array device, which can be based on an integrated circuit (IC), can be designed using complementary metal oxide silicon (CMOS) technology and includes photosensors, amplifiers, discriminators and logic circuitry on board. The highly integrated biochip can be produced using the capability of fabricating multiple optical sensing elements and microelectronics for up to 100 sensing channels on a single IC. The capability of large-scale production using low-cost IC technology is an important advantage. The assembly process of various components is made simple by cost-effective integration of multiple elements on a single chip. The nanoplasmonic biochip can me miniaturized such that it can be implanted into the skin and deep in tissue for real time or near real-time in vivo detection.

Figure 19A:
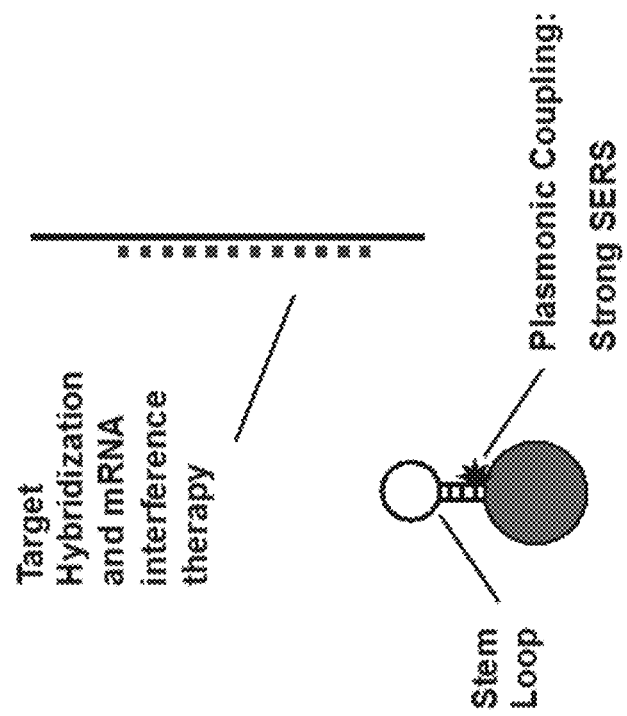
FIGS. 19A-19B are schematic diagrams illustrating use of the iMS nanoprobes for detection using SERS, and for treatment by RNA interference using siRNAs according to embodiments of the present disclosure.
Figure 19B:
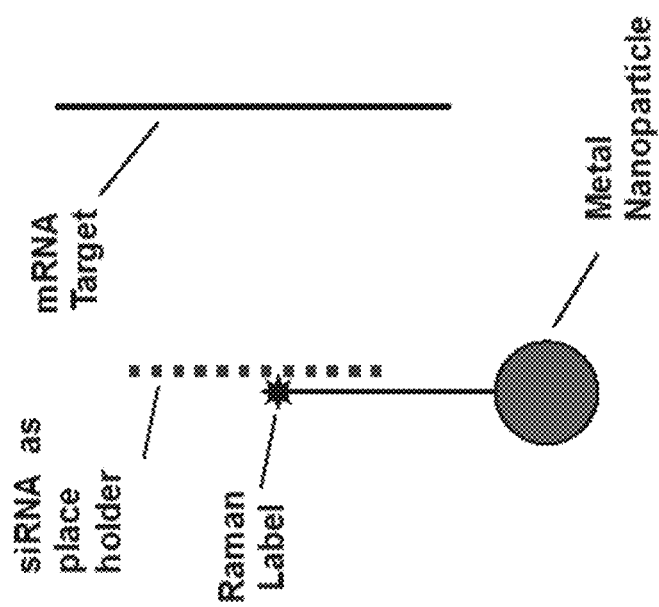
Figures 20A, 20B:
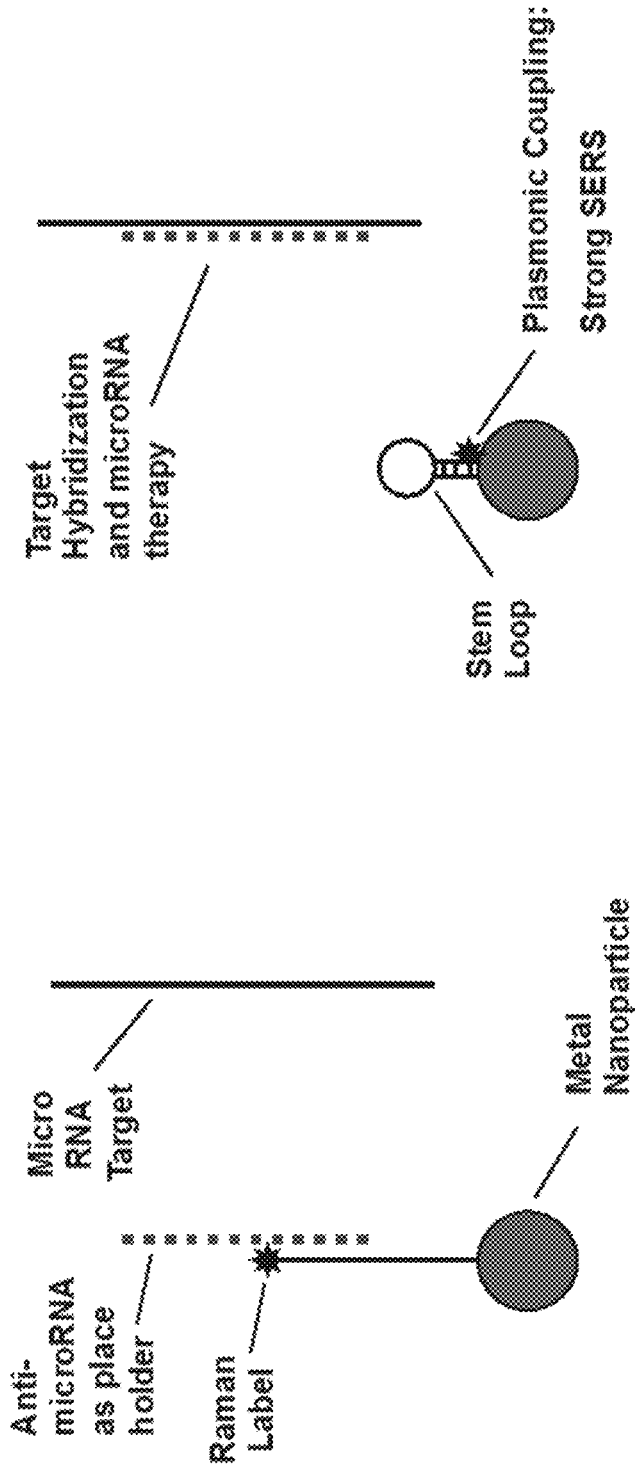
FIGS. 20A-20B are schematic diagrams illustrating use of the iMS nanoprobes for detection using SERS, and for treatment by RNA interference using anti-microRNAs according to embodiments of the present disclosure.

The nanoprobes of the present disclosure can also be used as a multifunctional nano-device for detection, imaging and therapy (theranostics). FIGS. 19 and 20 are schematic diagrams illustrating use of the iMS nanoprobes for detection using SERS, and for treatment by RNA interference using siRNAs (FIGS. 19A-19B) and anti-microRNAs (FIGS. 20A-20B). In this approach, the placeholder is a siRNA or an anti-microRNA for a specific mRNA or microRNA of interest as the therapeutic target.

The anti-biofouling strategies described herein above for retaining nanoprobe functionality in biological environments can also be employed with the theranostic nanoprobes. In addition, the theranostic nanoprobes can be encapsulated into nanocarriers. The family of nanocarriers can be broadly categorized as polymer, lipid, apoferritins, surfactant and nanomaterial-based systems. Compared to micrometer and sub-micrometer size carriers such as liposomes, nanocarriers provide higher surface area-to-volume ratio, and have the potential to increase solubility, enhance bioavailability, improve controlled release and enable precision targeting of the entrapped compounds to a greater extent. As a consequence of their improved stability and targeting, the amount of therapeutic molecules required to exert a specific effect when encapsulated in nanocarriers can be much less than the amount required when unencapsulated.

Figure 21A:
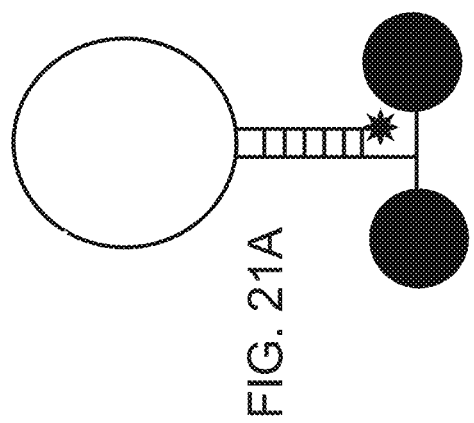
FIGS. 21A-21F are schematic diagrams showing various embodiments of plasmonics-active nanoprobes for improved sensitivity of the present disclosure: A) Nanoprobe having two metal nanoparticles; B) Nanoprobe having two metal nanotriangles; C) Nanoprobe having two metal nanocubes; D) Nanoprobe having three metal nanoparticles; E) Nanoprobe having six metal nanotriangles; and F) Nanoprobe having a dialetric nanoparticle core covered with a metal nanocap.
Figure 21B:
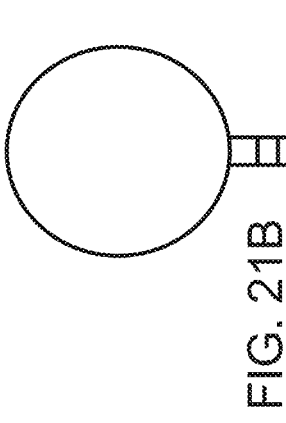
Figure 21C:
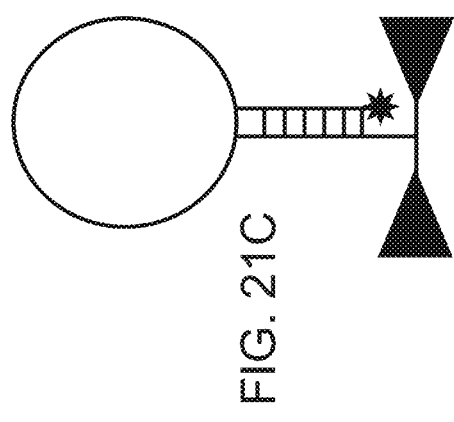
Figure 21D:
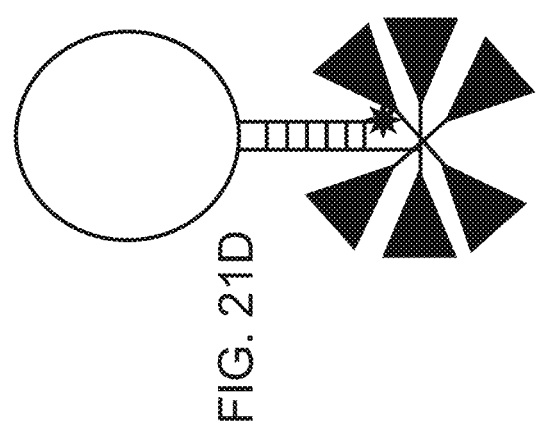
Figure 21E:
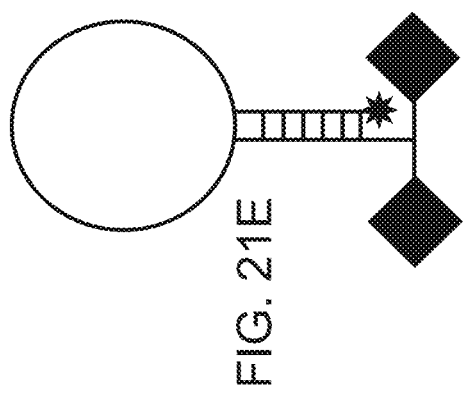
Figure 21F:
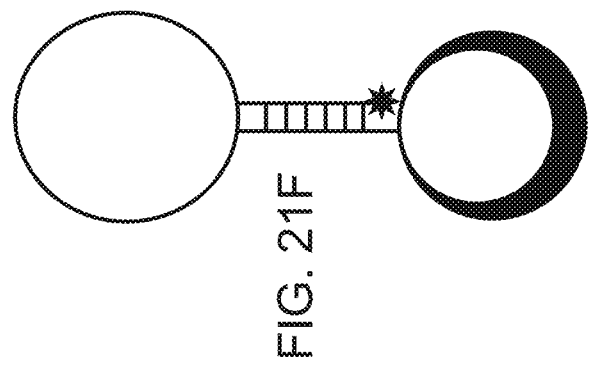

The plasmonics-active nanoprobes of the present disclosure can be designed for improved sensitivity. FIGS. 21A-20F are schematic diagrams showing various embodiments of plasmonics-active nanoprobes for improved sensitivity. For example, the nucleic acid stem of the iMS nanoprobe or the bioreceptor of the nanoprobe for detection of proteins can be attached to more than one nanoparticle. This is illustrated in FIGS. 21A-21F: A) Nanoprobe having two metal nanoparticles; B) Nanoprobe having two metal nanotriangles; C) Nanoprobe having two metal nanocubes; D) Nanoprobe having three metal nanoparticles; and E) Nanoprobe having six metal nanotriangles. In another example, the nanoparticle of the nanoprobe can be a dialetric nanoparticle core covered with a metal nanocap F).

In one embodiment, a method is provided for treating undesirable cells comprising: contacting an undesirable cell with the silver-coated gold nanostar resulting from a process comprising reducing aqueous silver ($Ag^+$) to solid silver ($Ag^0$) onto gold nanostar seeds under conditions such that the silver-coated gold nanostars are produced and having an optical label; and irradiating the sample with electromagnetic radiation from an excitation source, wherein the optical label is capable of absorbing electromagnetic radiation from one or both of electromagnetic radiation originated as a result of excitation of the nanostar and directly from the excitation radiation, and wherein the undesirable cells are damaged by one or both of thermal energy direct from the radiation and thermal energy emitted as a result of excitation of the nanostar.

In one embodiment, a method is provided for treating undesirable cells comprising: contacting an undesirable cell with a nanoprobe of the present disclosure; and irradiating the sample with electromagnetic radiation from an excitation source, wherein the optical label is capable of absorbing electromagnetic radiation from one or both of electromagnetic radiation originated as a result of excitation of the nanoparticle and directly from the excitation radiation, and wherein the undesirable cells are damaged by one or both of thermal energy direct from the radiation and thermal energy emitted as a result of excitation of the nanoparticle.

In the method for treating undesirable cells, the optical label can include a Raman dye, 3,3'-Diethylthiadicarbocyanine iodide (DTDC), 3,3'-diethylthiatricarbocyanine iodide (DTTC), 1,1',3,3,3',3'-Hexamethylindotricarbocyanine iodide (HITC), CY3 dye, CY3.5 dye, CY5.5 dye, CY7 dye, CY7.5 dye, a positively-charged hydrophobic near infrared (NIR) dye, IR-780, IR-792, IR-797, IR-813, methylene blue hydrate (MB), 4-mercaptobenzoic acid (4-MBA), 5,5'-dithiobis-2-nitrobenzoic acid (DTNB), 4-aminothiophenol (4ATP), fluorescein, fluorescein isothiocyanate (FITC), thionine dyes, rhodamine-based dye, crystal violet, a fluorescence label, or absorbance label. The method can further include detecting the electromagnetic radiation originated by the optical label by one or more of surface enhanced Raman scattering (SERS) detection, surface-enhanced resonance Raman scattering (SERRS), fluorescence detection, and absorbance detection.

In the method for treating undesirable cells, detecting the electromagnetic radiation originated by the optical label can serve to locate the targeted undesirable cells such that the irradiating can be better localized to the undesirable cells. The nanoparticle can include a protective layer surrounding the nanoparticle having within the layer one or more of a photosensitizer, a photoactivator, and a chemotherapy drug such that the photosensitizer, the photoactivator, and the chemotherapy drug is released or activated via one or more of passive diffusion release, photochemically triggered release, thermal triggered release, pH triggered release, photochemical activation, and thermal activation. The protective layer can include NIPAM. The undesireable cells can include cancer cells.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Preparation of Sliver (Gold) Nanoparticles

Silver (or gold) colloids were prepared according to the standard Lee-Meisel method: 200 mL of $10^{-3}$ M $AgNO_3$ aqueous solution was boiled under vigorous stirring, then 5 mL of 35-mM sodium citrate solution were added and the resulting mixture was kept boiling for 1 h. This procedure was reported to yield ~$10^{11}$ particles/mL of homogenously sized colloidal particles with a diameter of 35-50 nm and an absorption maximum at 390 nm. The colloidal solutions were stored at 4° C. and protected from room light. Further dilutions of the colloidal solutions were carried out using distilled water.

Example 2

Fabrication/Preparation of Metal Nanocaps

The approach used involved the use of nanospheres spin-coated on a solid support in order to produce and control the desired roughness. The nanostructured support was subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex nanospheres are commercially available in a wide variety of sizes. The shapes of these materials are very regular and their size can be selected for optimal enhancement. These materials consist of isolated dielectric nanospheres (30-nm diameter) coated with silver producing systems of hal-nanoshells, referred to as nanocaps. The nanoparticles can be sonicated to release them from the underlying substrate. The effect of the sphere size and metal layer thickness upon the SERS effect can be easily investigated. By rotating the platform supporting the nanospheres, one can extend the solver coverage and produce the "crescent structures" shown in FIG. 11. The silver coated nanospheres were found to be among the most plasmonics-active investigated. Gold can also be used instead of silver to coat over a nanoparticles materials.

Example 3

Fabrication of Gold Nanoshells

Gold nanoshells were prepared using the method described by Hirsch et al. [Hirsch L R, Stafford R J, Bankson J A, Sershen S R, Price R E, Hazie J D, Halas N J, West J L (2003) Nanoshell-mediated near infrared thermal therapy of tumors under MR Guidance. Proc Natl Acad Sci 100: 13549-13554]. A mechanism was used involving nucleation and then successive growth of gold nanoparticles around a silica dielectric core. Gold nanoparticles, the seed, prepared as described above using the Frens method, were used to grow the gold shell. Silica nanoparticles (100 nm) used for the core of the nanoshells were monodispersed in solution of 1% APTES in EtOH. The gold "seed" colloid synthesized using the Frens method were grown onto the surface of silica nanoparticles via molecular linkage of amine groups. The "seed" covers the aminated silica nanoparticle surface, first as a discontinuous gold metal layer gradually growing forming a continuous gold shell. Gold nanoparticles used as the "seed" were characterized using optical transmission spectroscopy (UV-Vis Spectrophotometer, Beckman Coulter, Fullerton, CA) and atomic force microscopy (Atomic Force Microscope, Veeco Instruments, Woodbury, NY) while gold nanoshells were characterized using optical transmission spectroscopy and scanning electron microscopy (Scanning Electron Microscope, Hitachi S-4700, Hitachi High Technologies America, Inc. Pleasanton, NY).

Example 4

SERS-Based "Off-to-On" Inverse Molecular Sentinel (IMS) Plasmonic Nanoprobes

The SERS-based "off-to-on" iMS nanoprobes are based on DNA strand-displacement reaction and hybridization with target (see FIGS. 2-4). The iMS nanoprobe is composed of a iMS hairpin nucleic acid stem attached to a plasmonic-active metallic (e.g. silver or gold) nanoparticle and a placeholder or capture probe. One end of the iMS stem was tagged with a SERS-active label as a signal reporter.

In this experiment, 1 µM complementary target or non-complementary single-stranded DNA (negative control) was added to the iMS-Placeholder (signal-OFF) solution and incubated at room temperature for 2 hours followed by SERS measurements. In the presence of the target sequences, a strong SERS signal was detected (data not shown). In contrast, only weak background signal was observed both in the blank (absence of analytes) sample and in the presence of non-complementary sequences (negative control). This result demonstrates that the placeholder was released from the iMS allowing the iMS hairpin structure to form and switching the SERS signal "ON".

Example 5

Improved Inverse Molecular Sentinel (IMS) Plasmonic Nanoprobes

Figure 22:
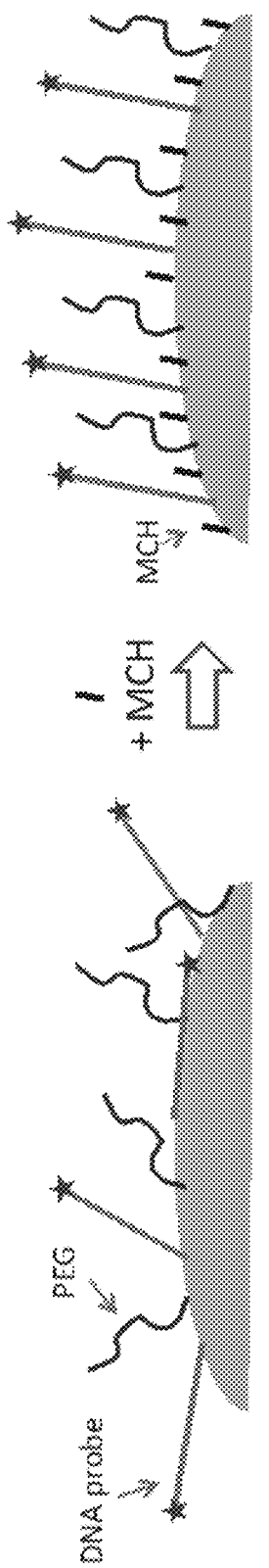
FIG. 22 is a schematic diagram of an improved iMS nanoprobe design according to embodiments of the present disclosure.

The effect of MCH (mercaptohexanol) on the hybridization efficiency of the iMS was investigated (FIG. 22). The results indicated that the addition of MCH displaced non-specific interactions between the DNA and Ag (or Au) and caused the DNA to stand up from the surface (data not shown). MCH improved the hybridization efficiency of the immobilized probes. In addition, addition of MCH was shown to aid in producing an effective "off" signal (data not shown).

Several designs were investigated to optimize the capability to turn "OFF" iMS SERS signal using placeholder. In this experiment, PEGylated-iMS nanoprobes were compared with and without the addition of MCH (mercaptohexanol). In the first case, the iMS nanoprobe was functionalized with 10-µM mPEG-350. The iMS nanoprobed in 2.5 mM $MgCl_2$-Tris buffer exhibited the SERS signal "ON" state. The SERS signal could not be completely turned "OFF" in the presence of 100 nM placeholder (data not shown). In the second case, the iMS nanoprobe was functionalized with 2-µM mPEG-350, and then incubated with 20 µM-MCH. The iMS nanoprobed in 5 mM $MgCl_2$-Tris buffer exhibited the SERS signal "ON" state. The SERS signal was completely turned "OFF" in the presence of 100 nM placeholder (data not shown).

Example 6

Preparation of a Plasmonics-Active Chip Substrate

The nanowave substrate fabrication involved two separate steps. The first step involved washing glass cover slips by incubating them in nitric acid, followed by a careful rinsing process with ultrapure DI water. This ensured removal of organic residue on the glass surface and populated the surface with hydroxyl groups. The cover slips were dried in a stream of nitrogen and placed on a spin coater. Silica nanospheres (100-nm diameter, Polysciences), dispersed in a ethanol:ethylene glycol solvent (85%:15% v/v), were dropcast on the cover slip and spun at 6000 rpm for 5 seconds. The nanospheres adhered to the coverslip, producing a close-packed array of silica nanospheres. The second step entailed coating the sphere-covered slides with a metal (gold or silver), achieved by transfer to an E-beam evaporator. To ensure uniform metal coating the substrates were rotated above the silver source during deposition, which was conducted at a vacuum pressure below $5 \times 10^{-6}$ Torr. The desired thickness of metal was evaporated onto the array of nanospheres, producing an array of silica@metal half-nanoshells, referred to as the Nanowave.

Example 7

Inverse Molecular Sentinel (IMS) Plasmonic Nanoprobes for Nucleic Acid Detection To further extend the use of SERS for nucleic acid detection, MS nanosensors were developed with unique properties, i.e. an "Off-to-On" detection scheme referred to as the "Inverse Molecular Sentinel" (iMS) nanoprobes (FIG. 2). In this study, the iMS detection method was implemented using gold nanostars as the SERS-active platform. The nanostars are surfactant-free nanoparticles with tunable plasmon resonances and multiple sharp branches making them ideal monomeric SERS platform due to their superior SERS enhancement factor. As shown in FIG. 2, the "stem-loop" DNA probe of the iMS, having a Raman label at one end of the stem, is immobilized onto a gold nanostar via a gold-thiol bond formed on the other end of the stem. A complementary DNA probe, serving as a "placeholder" strand bound to the iMS nanoprobe, keeps the Raman dye away from the nanostar surface. Because the plasmon field enhancement decreases significantly from the surface, a dye molecule must be located very close to the metal surface in order to experience the enhanced local plasmon field. Thus, in the absence of the target, the probe is denoted "Off" with low SERS signal, which is the "open" or "off" state. Upon exposure to the target sequences, the placeholder strand leaves the nanostar surface based on DNA strand displacement by the complementary target strand, allowing the stem-loop to close and moving the Raman label onto the gold surface; this yields a strong SERS signal, and is thus denoted "On" or "closed" state.

In this study, the human radical S-adenosyl methionine domain containing 2 (RSAD2) gene was used as the model system to demonstrate feasibility of the method. This gene is well known for its critical role in host immune response to viral infection. For infectious disease diagnosis, this approach involves detecting the host response to various pathogens by evaluating changes in gene expression in response to infection. For example, upon viral infection, type I interferons (IFNs) are produced and secreted by infected cells to initiate a complex signaling cascade, leading to the induction of hundreds of genes that limit viral infection. Among these antiviral genes, the RSAD2 gene encoding a protein known as Viperin has been recognized as one of the most highly induced genes upon interferon stimulation or infection with various viruses. Thus, it is an excellent host-response biomarker for diagnosis of viral infections.

To test the effectiveness of the designed iMS nanoprobes for RSAD2, the Cy5-labeled iMS nanoprobes were first conjugated with placeholders in PBS overnight at 37° C. to ensure that the stem-loop probes are open (signal "Off"). The iMS-placeholder conjugates were then tested with their complementary target DNA in PBS for 1 hour at 37° C. FIG. 23 shows the SERS spectra of the iMS nanoprobes in the presence or absence of target DNA sequences: A) blank (no target DNA present); B) in the presence of 1 µM non-complementary DNA (negative control); and C) in the presence of 1 µM complementary target DNA. In the presence of target DNA (FIG. 23C), the SERS intensity of the major Raman bands was significantly increased indicating that the Cy5 dyes were in close proximity to the nanostar surface. The increased SERS signal indicates that hybridization between the targets and placeholder strands enabled the stem-loop structure of the DNA probes to close, thereby moving the SERS dye Cy5 onto the nanostar surface. In this case, the SERS signal of the iMS nanoprobes was turned "On". On the other hand, in the presence of non-complementary DNA (negative control: FIG. 23B), the SERS intensity of the major Raman bands remained similar to the blank sample (FIG. 23A), indicating that the dye molecules were separated from the gold surface by the placeholder strands; that is, the iMS nanoprobes adopted an open stem-loop configuration (SERS "Off") in the absence of targets.

In another experiment, the iMS nanoprobes were designed as described above. However, in this case, the iMS-placeholder conjugates were incubated with their complementary target DNA for only 10 minutes rather than 1 hour prior to measurement of the SERS spectra. Again, in the presence of the target DNA, the SERS intensity of the major Raman bands was significantly increased relative to that in the absence of the target DNA indicating that hybridization between the target and placeholder strands enabled the stem-loop structure of the DNA probes to close such that the Raman dye moved onto the nanosphere surface (data not shown).

In another experiment, the iMS nanoprobes were designed as described for the first experiment above. However, in this case, 10 nM rather than 1 μM target DNA was used. Again, in the presence of the target DNA, the SERS intensity of the major Raman bands was significantly increased relative to that in the absence of the target DNA indicating that hybridization between the target and placeholder strands enabled the stem-loop structure of the DNA probes to close such that the Raman dye moved onto the nanosphere surface (data not shown).

In another experiment, Raman dye-labeled and PEGlyated iMS nanoprobes were generated using silver nanosphere cores. As described above, the nanoprobes were first conjugated with placeholders to ensure that the stem-loop probes were open (signal "Off"). The SERS spectra of the iMS-placeholder conjugates were measured in the presence or absence of 1 μl target DNA sequences. In the presence of the target DNA, the SERS intensity of the major Raman bands was significantly increased relative to that in the absence of the target DNA indicating that hybridization between the target and placeholder strands enabled the stem-loop structure of the DNA probes to close such that the Raman dye moved onto the nanosphere surface (data not shown).

In conclusion, the utility has been demonstrated of using the "Off-to-On" iMS nanoprobes to detect nucleic acid targets using SERS and plasmonic gold nanostars. Moreover, this iMS approach does not require labeling targets and post-hybridization washing steps, making the assay procedure simple and rapid. The results from this study demonstrate the utility of the iMS approach as a diagnostic tool to detect nucleic acid biomarkers for medical applications.

EXPERIMENTAL SECTION

DNA Sequences:

The stem-loop and placeholder DNA probes used for RSAD2 detection were 5'-thiol-CTCTATAAGTGGTG-TAGGGATTATAGAG-Cy5-3' (SEQ ID NO: 1) and 5'-GAAAGCGACTCTATAATCCCTACACCAC-3' (SEQ ID NO: 2), respectively. The synthetic RSAD2 DNA target and non-complementary sequences used for the demonstration were 5'-AAAGCTGAGGAGGTGGTGTAGGGAT-TATAGAGTCGCTTTCAAGATAAATT-3' (SEQ ID NO: 3) and 5'-TCATCCATGACAACTTTGGTATCGTGGAAGG-ACTCATGAC-3' (SEQ ID NO: 4), respectively. All oligonucleotides were purchased from Integrated DNA Technologies, Inc (Coralville, IA).

Preparation of Gold Nanostars:

The gold nanostars were prepared as described previously. Briefly, 12 nm seed solution was first prepared using a modified Turkevich method. Gold nanostars were then grown from the seed by simultaneous addition of 100 μL of 2 mM $AgNO_3$ and 50 μL of 0.1 M ascorbic acid to a solution containing 10 mL of 0.25 mM $HAuCl_4$, 10 μL of 1 N HCl, and 100 μL of the 12 nm gold seed solution under vigorous stirring. After 10 s, the solution turned from light red to a dark gray. The stock concentration of nanoparticles is approximately 0.1 nM, as determined by nanoparticle tracking analysis (NTA).

Synthesis of Inverse Molecular Sentinel (IMS) Nanoprobes:

The stem-loop DNA probes were first treated with 0.1 M dithiothreitol (DTT) at room temperature for 1 hr followed by desalting in NAP-5 columns (GE Healthcare) to remove the disulfide protecting groups. The deprotected stem-loop probes (at final concentration of 0.1 μM) were then incubated with gold nanostars in 0.25 mM $MgCl_2$ solution overnight at room temperature. To stabilize the nanoprobes, 1 μM of O-[2-(3-mercaptopropionylamino)ethyl]-O'-methylpolyethylene glycol (mPEG-SH, 5000) was added to the solution for 30 min. The gold surface of nanostars was then passivated using 0.1 mM 6-mercapto-1-hexanol (MCH). The functionalized nanoprobes were washed with Tris-HCl buffer (10 mM, pH 8.0) containing Tween 20 (0.01%) using repeated centrifugation at 7,000 rpm for 10 min. The purified nanoprobes were finally resuspended in Tris-HCl buffer (10 mM, pH 8.0).

IMS Assay Procedure:

To turn off the iMS SERS signal, the nanoprobes were incubated with 0.1 mM placeholder probes in PBS buffer solution overnight at 37° C. The "Off" iMS nanoprobes were then incubated with 1 μM target or non-complementary sequences at 37° C. for 1 hr followed by SERS measurements using a Renishaw InVia confocal Raman microscope equipped with a 632.8 nm HeNe laser. The light from the laser was passed through a laser line filter, and focused into the sample solution with a 10× microscope objective. The Raman scattered light was then detected by a 1024×256 pixel R.

Example 8

Synthesis of IMS Nanoprobes with Sliver-Coated Gold Nanostars for SERS Detection Nanostar Synthesis (AuNS).

Two sizes of AuNS were synthesized as previously reported. A 12 nm gold seed solution was prepared by adding 15 mL of 1% trisodium citrate to 100 mL of a boiling solution of 1 mM $HAuCl_4$. This solution was kept boiling for an additional 15 minutes, cooled to room temperature in an ice bath, filtered through a 0.22 μm nitrocellulose membrane, and stored at 4° C. until use. To produce the larger AuNS, designated S30, 100 μL of the gold seed was added to a 10 mL solution of 0.25 mM $HAuCl_4$ containing 10 μL of 1 N HCl, immediately followed by the simultaneous addition of 50 μL 0.1 M AA and 100 μL 3 mM $AgNO_3$ under moderate stirring. The smaller AuNS, designated S5, were produced in the same manner as above, but using 0.5 mM $AgNO_3$ in place of 3 mM $AgNO_3$. After synthesis, 100 μL of 0.1 M CTAB was added to the AuNS solution and left stirring for 5 minutes. The particles were then centrifuged at 2000 rcf for 20 minutes at 4° C., the supernatant discarded, and the particles re-dispersed in 10 mL of 1 mM CTAB solution.

Silver Coating of Gold Nanostars (AuNS@Ag).

A 1 mL aliquot of the washed AuNS solution was transferred into a 1.5 mL centrifuge tube. The sample was briefly vortexed after each subsequent chemical addition. A small volume (varied between 0 and 15 μL) of 0.1 M $AgNO_3$ and an equivalent volume of 0.1 M AA were added to the solution. The reduction of silver by AA was initiated by the addition of $NH_4OH$ (same volume as above), at which point the color of the solution began to darken. After about 5 minutes, the solution color had stabilized, indicating completion of the reaction. The various silver-coated AuNS samples were designated according to the volume of $AgNO_3$ added (e.g., S30@Ag5 for S30 AuNS coated using 5 µL of 0.1 M $AgNO_3$). The silver coated AuNS were then labeled with dye by adding 1 µM final concentration of the desired dye (dissolved in EtOH) to the solution, allowing it to sit for 15 minutes, centrifuging at 2000 rcf for 10 minutes, discarding the supernatant, and re-dispersing in water.

Synthesis of Inverse Molecular Sentinel (IMS) Nanoprobes:

The stem-loop DNA probes were first treated with 0.1 M dithiothreitol (DTT) at room temperature for 1 hr followed by desalting in NAP-5 columns (GE Healthcare) to remove the disulfide protecting groups. The deprotected stem-loop probes (at final concentration of 0.1 µM) were then incubated with gold nanostars in 0.25 mM $MgCl_2$ solution overnight at room temperature. To stabilize the nanoprobes, 1 µM of O-[2-(3-mercaptopropionylamino)ethyl]-O'-methylpolyethylene glycol (mPEG-SH, 5000) was added to the solution for 30 min. The gold surface of nanostars was then passivated using 0.1 mM 6-mercapto-1-hexanol (MCH). The functionalized nanoprobes were washed with Tris-HCl buffer (10 mM, pH 8.0) containing Tween 20 (0.01%) using repeated centrifugation at 7,000 rpm for 10 min. The purified nanoprobes were finally resuspended in Tris-HCl buffer (10 mM, pH 8.0).

IMS Assay Procedure:

To turn off the iMS SERS signal, the nanoprobes were incubated with 0.1 mM placeholder probes in PBS buffer solution overnight at 37° C. The "Off" iMS nanoprobes were then incubated with 1 µM target or non-complementary sequences at 37° C. for 1 hr followed by SERS measurements using a Renishaw InVia confocal Raman microscope equipped with a 632.8 nm HeNe laser. The light from the laser was passed through a laser line filter, and focused into the sample solution with a 10× microscope objective. The Raman scattered light was then detected by a 1024×256 pixel R.

The iMS-placeholder conjugates were incubated with their complementary target DNA (1 µM) and SERS spectra were measured. As described above in Example 6, in the presence of the target DNA, the SERS intensity of the major Raman bands was significantly increased relative to that in the absence of the target DNA indicating that hybridization between the target and placeholder strands enabled the stem-loop structure of the DNA probes to close such that the Raman dye moved onto the nanosphere surface (data not shown).

In a similar experiment, the silver coated iMS nanoprobes were used to distinguish targets having a single G/C base mismatch (the signal observed was ~45% less than that observed for the exact-match target).

In a similar experiment, the silver coated iMS nanoprobes were embedded in a NIPAM-hydrogel protective coating. These nanoprobes were demonstrated to possess similar target detection capability as described for the iMS nanoprobes without the NIPAM-hydrogel (data not shown).

Example 9

Hybrid Sliver-Coated Gold Nanostars for Surface-Enhanced Raman Scattering (SERS)

In the ongoing search for ever-brighter surface-enhanced Raman scattering (SERS) nanoprobes, gold nanostars (AuNSs) have emerged as one of the best geometries for producing SERS in a non-aggregated state. However, for in vivo applications, optical extinction from tissue and plasmon-matched nanoparticles can greatly attenuate the SERS intensity. Herein, the development of a new hybrid bimetallic nanostar-based platform that exhibits superior SERS properties is reported. In this new nanoplatform, coating AuNSs with a subtotal layer of silver (AuNS@Ag) further increased their SERS brightness by an order of magnitude when being interrogated by an off-resonant excitation source. Silica-encapsulated AuNS@Ag nanoprobes were injected intra-dermally into a rat pelt, where SERS was readily detected with higher signal-to-noise than nanoprobes prepared from AuNS. Moreover, these off-resonance AuNS@Ag nanoprobes did not cause any gross photothermal damage to tissue, which was observed with the plasmon-matched AuNSs. This SERS-active hybrid nanoprobe exhibits high SERS brightness and offers promising properties for future applications in sensing and molecular imaging.

In recent years, much effort has been devoted to the development of nanoparticles with the brightest SERS possible. While gold and silver nanosphere colloids have long been used in SERS studies, aggregation is typically required to generate the "hot-spots" of electromagnetic field for high SERS enhancement. Although this can give extremely low limits of detection, reproducibility becomes an issue when aggregation is relied upon. To overcome this problem, nanoparticles with intrinsic hotspots, such as nanorods and AuNSs, can be employed. AuNSs exhibit superior SERS properties owing to their tunable plasmon, for matching the excitation wavelength, and multiple sharp branches, each with a strongly enhanced electromagnetic (EM) field localized at its tip.

The present experiment describes the development of nanosensor for ex vivo and in vive applications, which presented several challenges. The first issue was the extremely high attenuation of SERS signal when attempting to detect the particles through tissue. The second issue found was the efficient photothermal transduction of AuNS solution, causing unwanted localized tissue burning. It was interesting to note that when using a commercially available SERS nanoprobes based on aggregated gold nanospheres, the signal attenuation due to self-absorption was lower and heating of the solution after laser excitation was minimal. Such phenomena can be explained by the mismatch between the extinction maximum of these nanoparticles and the wavelength of the incident laser, hence limiting photothermal transduction and self-absorption of the Raman scattered light Other reports have recently shown that plasmon matching is not as desirable as once thought when performing SERS measurements in solution. It was therefore of interest to develop highly SERS active (i.e., highest brightness factor) nanoparticles without the aforementioned disadvantages.

Two strategies were employed in this study. One was to use resonant dyes to generate resonant SERS (SERRS). The other was to modify the composition and plasmon band of the nanoparticles to enhance their optical properties through silver coating. This process allowed the monodispersity of gold nanoparticles to be preserved while taking advantage of the superior optical properties of silver. Although silver coating has previously been applied to various gold nanoparticles, there have been no reports about the coating of silver on AuNSs for making SERS nanoprobes. Herein, we describe a method to coat AuNSs with different amounts of silver, resulting in an order of magnitude increase in SERS brightness. By blue-shifting the plasmon of the particles, there is a significant decrease in the amount of self-absorption and heat generated when irradiating with a NIR laser. These silver-coated gold nanostars (AuNS@Ag) were used to make silica-coated SERS nanoprobes that were injected into rat skin ex vivo to demonstrate the utility of thisl SERS platform in biological applications.

EXPERIMENTAL

Materials. Gold(III) chloride trihydrate ($HAuCl_4 \cdot 3H_2O$), L(+)-ascorbic acid (AA), tetraethyl orthosilicate (TEOS), trisodium citrate dihydrate, 1 N hydrochloric acid solution (HCl), hexadecyltrimethylammonium bromide (CTAB, product H9151), Dulbecco's phosphate buffered saline (PBS), O-[2-(3-Mercaptopropionylamino)ethyl]-O'-methylpolyethylene glycol (mPEG-SH, MW 5k), IR-780 iodide, 3,3'-Diethylthiadicarbocyanine iodide (DTDC), 3,3'-Diethylthiatricarbocyanine iodide (DTTC), and 1,1',3,3,3',3'-Hexamethylindotricarbocyanine iodide (HITC) were purchased from Sigma-Aldrich (St. Louis, MO, USA) at the highest purity grade available. Silver nitrate ($AgNO_3$, 99.995%) was supplied by Alfa Aesar (Ward Hill, MA, USA). Ammonium hydroxide ($NH_4OH$, 29.5%), carbon-coated copper TEM grids, 1 mL disposable syringes, 27 G×½" needles, and 200 proof ethanol (EtOH) were obtained through VWR (Radnor, PA). All glassware and stir bars were thoroughly cleaned with aqua regia and dried prior to use. Ultrapure water (18 M$\omega \vdash$ cm) was used in all preparations.

Instrumentation. Raman spectra were recorded with a PIXIS:100BReX CCD mounted to a LS-785 spectrograph (1200 g mm$^1$ grating), controlled by LightField software, from Princeton Instruments (Trenton, NJ). A 785 nm diode laser was fiber-coupled to an InPhotonics RamanProbe (Norwood, MA) for excitation, with a power of 150 mW at the sample; the collection fiber of the RamanProbe was coupled to the entrance slit of the LS-785 spectrograph. Absorption spectra were collected with a FLUOstar Omega plate reader (BMG LABTECH GmbH, Germany). A FEI Tecnai G$^2$ Twin transmission electron microscope (Hillsboro, OR, USA) was used to acquire transmission electron microscopy (TEM) micrographs. Particle size distributions were measured by Nanoparticle Tracking Analysis (NTA) on a NanoSight NS500 (Amesbury, UK).

Nanostar Synthesis (AuNS). Two sizes of AuNS were synthesized as previously reported. A 12 nm gold seed solution was prepared by adding 15 mL of 1% trisodium citrate to 100 mL of a boiling solution of 1 mM $HAuCl_4$. This solution was kept boiling for an additional 15 minutes, cooled to room temperature in an ice bath, filtered through a 0.22 µm nitrocellulose membrane, and stored at 4° C. until use. To produce the larger AuNS, designated S30, 100 µL of the gold seed was added to a 10 mL solution of 0.25 mM $HAuCl_4$ containing 10 µL of 1 N HCl, immediately followed by the simultaneous addition of 50 µL 0.1 M AA and 100 µL 3 mM $AgNO_3$ under moderate stirring. The smaller AuNS, designated S5, were produced in the same manner as above, but using 0.5 mM $AgNO_3$ in place of 3 mM $AgNO_3$. After synthesis, 100 µL of 0.1 M CTAB was added to the AuNS solution and left stirring for 5 minutes. The particles were then centrifuged at 2000 rcf for 20 minutes at 4° C., the supernatant discarded, and the particles re-dispersed in 10 mL of 1 mM CTAB solution.

Silver Coating of Gold Nanostars (AuNS@Ag). A 1 mL aliquot of the washed AuNS solution was transferred into a 1.5 mL centrifuge tube. The sample was briefly vortexed after each subsequent chemical addition. A small volume (varied between 0 and 15 µL) of 0.1 M $AgNO_3$ and an equivalent volume of 0.1 M AA were added to the solution. The reduction of silver by AA was initiated by the addition of $NH_4OH$ (same volume as above), at which point the color of the solution began to darken. After about 5 minutes, the solution color had stabilized, indicating completion of the reaction. The various silver-coated AuNS samples were designated according to the volume of $AgNO_3$ added (e.g., S30@Ag5 for S30 AuNS coated using 5 µL of 0.1 M $AgNO_3$). The silver coated AuNS were then labeled with dye by adding 1 µM final concentration of the desired dye (dissolved in EtOH) to the solution, allowing it to sit for 15 minutes, centrifuging at 2000 rcf for 10 minutes, discarding the supernatant, and re-dispersing in water.

Silica Coating (AuNS@Ag@$SiO_2$). Silica was coated onto the labeled AuNS@Ag using an established protocol. To the 1 mL sample of dye-labeled particles prepared above, 5 µL of 1 mM mPEG-SH was added and allowed to react for 1 hour. The solution was washed once by centrifugation (2500 rcf, 10 min) and then dispersed in 900 µL of EtOH with 200 µL of water. Silica coating was initiated by adding 18 µL of $NH_4OH$ followed by 5 µL of 10% TEOS in EtOH to the solution. The reaction was allowed to proceed for 12 hours, at which point the sample was washed twice by centrifugation at 3000 rcf for 5 minutes and re-dispersed in water.

SERS Nanoprobe Injections. A shaved rat pelt was provided by Dr. Bruce Klitzman. Prior to injection, 1 mL of AuNS@Ag@$SiO_2$ were centrifuged at 3000 rcf for 5 minutes and the supernatant discarded. The particles were then re-dispersed in 100 µL of PBS, giving a particle concentration of about 1 nM. A 1 mL disposable syringe with a 27 G needle was used to draw up ~50 µL of the PBS particle solution. The needle was inserted tangentially to the skin (intradermal) with the bevel facing upward and ~25 µL of the solution was injected. The rat pelt was then placed under the focus of the RamanProbe to collect SERS spectra.

Synthesis and Characterization. The AuNSs used in this study were prepared as described previously above. To better characterize the silver coating process, two types of AuNSs were prepared: S5, which have low branch numbers, an average particle size around 50 nm, and an extinction maximum at 650 nm; and S30, which have high branching, an average particle size around 70 nm, and an extinction maximum at 850 nm. After synthesis, CTAB was added as a surfactant to stabilize the particles, which were then purified by centrifugation to remove any unreacted reagents. Nanoparticle samples are designated as described in the experimental section.

Silver coating of the AuNSs was performed in a similar manner to previous reports on the coating of gold nanorods with silver. In this method, the CTAB-stabilized AuNSs are used as seeds for the growth of a silver shell. Ascorbic acid serves as the reducing agent, with silver nitrate used as the precursor to elemental silver. After adding AA and $AgNO_3$ to the AuNS seed solution, $NH_4OH$ is introduced to increase the pH, initiating the reduction of $Ag^+$ to $Ag^0$ by AA. An immediate color change is observed after the pH is adjusted and the extinction maximum of the solution begins to blue-shift from the NIR region. After about 5 minutes, the color of the solution stabilizes, indicating completion of the silver coating reaction. The morphology of these particles after coating with different amounts of silver was investigated by TEM (data not shown). It was observed that the silver deposition begins mainly on the core of the particles, spreading outward as the amount of silver is increased until the branches are completely covered, resulting in a quasispherical shape. As can be expected, the smaller S5 have their branches mostly covered at lower amounts of silver than the larger S30.

To further confirm the growth of silver onto the AuNS, as opposed to nucleation of isolated silver nanospheres, UV/Vis absorption spectroscopy was employed (data not shown). For both S5@Ag and S30@Ag, the extinction maximum was blue-shifted to ~500 nm and increased in intensity with increasing amounts of silver. No peak was observed at ~420 nm, where the plasmon peak of silver nanospheres occurs. The blue-shifting AuNS plasmon, along with the absence of a plasmon peak at ~420 nm are indicative of silver shell formation on the AuNS.

To fabricate the strong SERS nanoprobes with the highest brightness, several factors were taken into consideration. Resonant SERS was employed because it generates multiple orders of magnitude higher SERS signal than non-resonant SERS on non-aggregated AuNS. In addition, it has been demonstrated that when using resonant dyes, a plasmon that is blue-shifted from the excitation provides the highest signal, as self-absorption effects are minimized when the plasmon is off-resonance from the excitation. Previously, sodium dodecyl sulfate (SDS) was used as a surfactant on AuNSs to aid in stabilization and dye adsorption. It is believed that the hydrophobic bilayer formed by the SDS helps to entrap dyes near the particle surface. It has also been demonstrated that CTAB can act in the same manner, and exhibits about two to three times higher signal intensity than particles stabilized with SDS. The longer hydrophobic chain of CTAB (16 carbons) versus SDS (12 carbons) likely provides a larger volume for trapping dye molecules.

For SERS intensity evaluation, the overall SERS brightness of the nanoparticle samples was compared in lieu of calculating their enhancement factors, which tend to be inaccurate as a consequence of assumptions made in their determination. Factors that would interfere with an enhancement factor calculation include: the irregular shape of the nanoparticles making it difficult to calculate their surface area to determine the number of dye molecules that can bind per particle, the use of CTAB leading to more than a monolayer of dye coverage per particle, and self-absorption of the particles reducing the measured Raman signal.

To investigate the effect of the various silver coatings on Raman enhancement, AuNSs@Ag samples were labeled with a NIR resonant dye, IR-780, for surface-enhanced resonant Raman scattering (SERRS) measurements (data not shown). At its highest intensity, with S5@Ag3, the signal was enhanced 16±2 times over the S5@Ag0. For S30@Ag samples, the highest intensity was observed at S30@Ag7, which is 9±1 times higher than the signal of S30@Ag0. It is worth noting that the maximal SERS brightness was found on AuNS with sub-total silver coating. It was apparent that the maximum Raman signal enhancement occurs right before the gold tips become completely embedded in the silver shell. More silver does not always lead to higher SERS response. Thus, a near-total silver coverage can add the benefit of silver enhancement while retaining the hot-spots from the AuNS tips to yield the strongest SERS. The lower self-absorption from the surrounding off-resonant nanoparticles plays a significant role as well. In contrast, spherical silver coating with a mismatched plasmon maximum but no sharp tips had a SERS brightness that was only slightly greater than NS@Ag0.

In order to make sure that the particles were not aggregated, which would cause anomalously high Raman signals, the size distributions of S30@Ag were evaluated by NTA, both before and after dye labeling (data not shown). No significant increase in particle size was observed after dye labeling, adding confidence that the particles remained in a non-aggregated state. The observed drop-off in Raman signal intensity after a certain amount of silver coating further supports the claim that particles remain non-aggregated after dye labeling. With mostly spherical-shaped particles found in solution after the optimum amount of silver coating is surpassed, any type of aggregation would result in a marked increase in Raman signal.

Figure 24A:
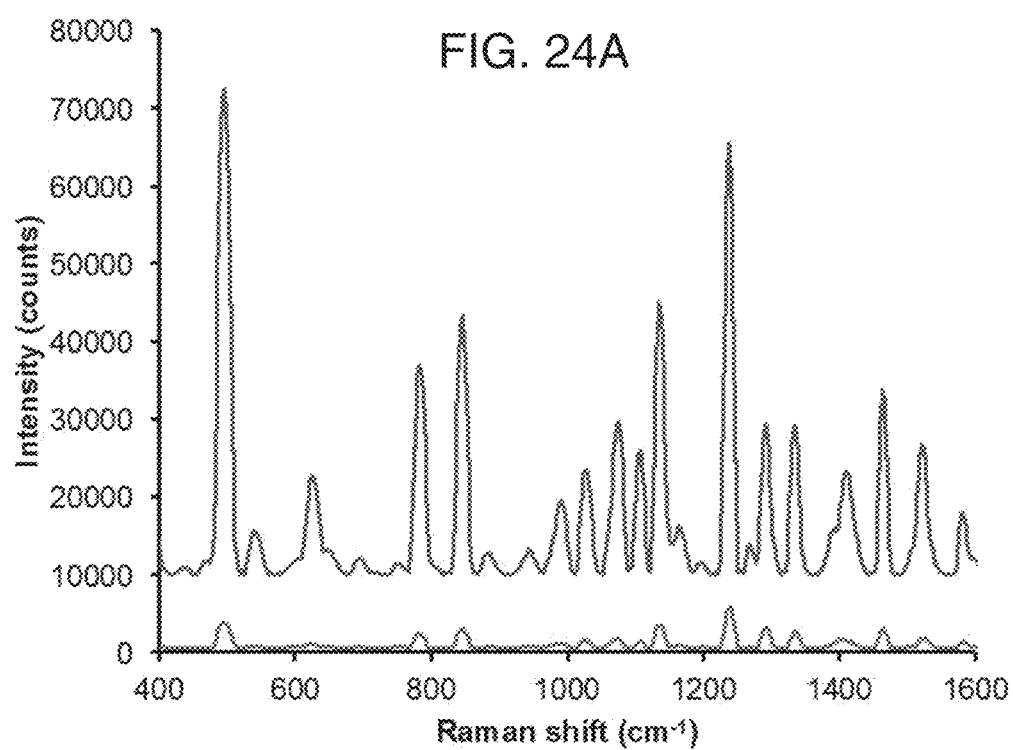
FIGS. 24A-24C are spectra and TEM micrographs of the Ag0 and Ag7 SERS nanoprobes according to embodiments of the present disclosure. A) Comparison of Raman signal intensity from S30@Ag0-DTTC@SiO$_2$ (lower spectrum) and S30@Ag7-DTTC@SiO$_2$ (upper spectrum), collected with a 100 ms exposure time. The spectra have been background subtracted and offset for clarity. B) TEM micrograph of the Ag0 nanoprobes. Scale bars are 100 nm. C) TEM micrograph of the Ag7 SERS nanoprobes. Scale bars are 100 nm.
Figures 24B, 24C:
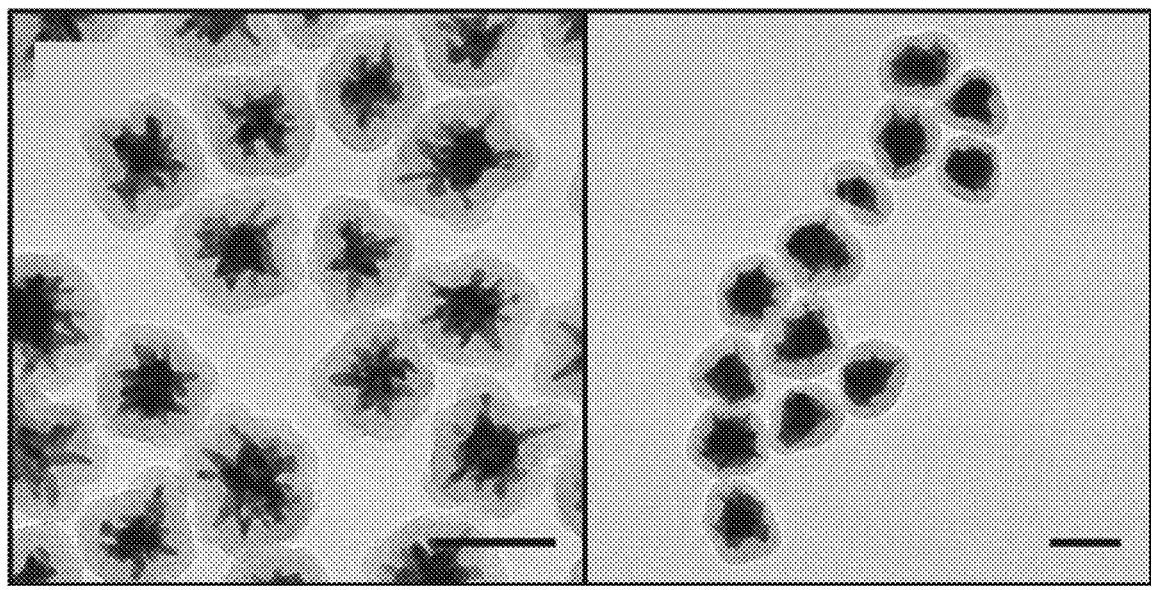

SERS Nanoprobe Preparation. In order to make Raman-labeled particles suitable for bio-applications, it is necessary to encapsulate the particles in an inert material, e.g. silica. Coating the Raman nanoprobes with silica helped to keep the dye trapped on the particle surface, making them more stable, and prevented unwanted adsorption of other molecules that may generate their own Raman signal. SERS nanoprobes were prepared using three different carbocyanine dyes (DTDC, DTTC, and HITC) to demonstrate the potential for multiplex detection. Thiol-PEG was used to stabilize the particles when transferred into ethanol for silica coating by a modified Stöber method. The PEG layer also acted to facilitate silica condensation onto the surface of the particles, presumably through hydrogen bonding. This method was found to be equally effective at encapsulating both silver-coated and bare AuNS. The measured particle size distribution showed no obvious signs of aggregation after silica coating. FIG. 24A shows a comparison of the Raman signal intensity from silica-coated, DTTC-labeled S30@Ag0 and S30@Ag7. It is shown that after silica coating, the order of magnitude in signal difference between the Ag0 and Ag7 S30 is maintained. The TEM micrographs shown in FIGS. 24B and 24C demonstrate that both particle types were completely coated and in a non-aggregated state.

Intradermal Injection of SERS Nanoprobes Ex Vivo. To show the potential of the new AuNS@Ag in biological applications, the prepared SERS nanoprobes were injected into a rat pelt for ex vive detection. To prepare the particles for injection, the solutions were concentrated ten times and dispersed in sterile PBS. The particle solutions were drawn up into 1 mL syringes with a 27 G needle. About 25 µL of each SERS nanoprobe was injected into the skin at different locations. The injection volume produced a small welt, with the particle solutions clearly visible through the skin (data not shown). The injection area was then swabbed with an alcohol pad before optical interrogation with the Raman-Probe.

A Raman signal was observed for the three AuNS@Ag SERS nanoprobes (DTTC, HITC, and DTDC), as well as the DTTC AuNS SERS nanoprobe (data not shown). The S30@Ag7-DTTC@SiO$_2$ nanoprobe showed a higher signal-to-noise ratio than the S30@Ag0-DTTC@SiO$_2$ nanoprobe, demonstrating enhanced signal generation from the silver-coated AuNS. The difference in signal intensity from resonant (DTTC and HITC) and non-resonant (DTDC) dyes was also observed, with the resonant dyes providing an order of magnitude higher signal than the non-resonant dye.

Another benefit of the AuNS@Ag SERS nanoprobes is that the extinction maximum no longer occurs in the region of the laser excitation. No adverse effects on the tissue were seen for the AuNS@Ag nanoprobes after laser interrogation. However, a small area of burnt tissue was observed in the center of the S30@Ag0-DTTC@SiO$_2$ injection site after the measurement had been performed. It has previously been shown that the AuNS are efficient photothermal transducers due to their high absorption:scattering ratio. In this case, the power of the incident laser was high enough to cause burning of the tissue when non-silver coated AuNS were used. Although matching the laser excitation to the surface plasmon resonance of nanoparticles will generate the highest electromagnetic field enhancement for SERS, this study demonstrates that this is not always desirable, as doing so can lead to unintended tissue damage.

This report described the synthesis, characterization, and application of a hybrid bimetallic platform, AuNS@Ag, for SERS detection. The amount of silver coating was optimized to give the greatest SERS brightness. The morphology of the particles was assessed by TEM, while the optical properties were characterized with UV/Vis absorption spectroscopy and Raman spectroscopy. In the optimized configuration, AuNS@Ag provided over an order of magnitude of signal enhancement compared to uncoated AuNS. Three different dye-labeled AuNS@Ag were coated with a silica shell to create SERS nanoprobes, entrapping the dye and preserving the non-aggregated state of the particles. To demonstrate the utility of these particles in bio-labeling applications, ex vive detection was performed following intradermal injection of the SERS nanoprobes into a rat pelt. Raman signal was detected from all three SERS nanoprobes, and the measurements did not cause any noticeable damage to the skin. The SERS nanoprobe created from non-silver-coated AuNS caused burning of the tissue after laser irradiation, due to photothermal conversion caused by the overlap between the particles' surface plasmon resonance and the wavelength of the incident light.

Any patents or publications mentioned in this specification are indicative of the levels of those skilled in the art to which the present disclosure pertains. These patents and publications are herein incorporated by reference in their entiretly to the same extent as if each individual publication was specifically and individually indicated to be incorporated by reference.

One skilled in the art will readily appreciate that the present present disclosure is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

We claim:

1. An inverse molecular sentinel nanoprobe for detecting a nucleic acid target, comprising
   a metal nanoparticle,
   an oligonucleotide molecule comprising a sequence that forms a stem loop, wherein the sequence comprises from 5' to 3' a stem-L sequence, a loop, and a stem-R sequence, wherein the stem-L sequence is complementary to the stem-R sequence, wherein the sequence that forms a stem loop or a portion thereof is a placeholder binding sequence, a separate placeholder strand comprising a first region complementary to a target sequence in the nucleic acid target and a second region complementary to the placeholder binding sequence, wherein the first region is 20-30 nucleotides in length, wherein the placeholder binding sequence is 8-15 contiguous nucleotides of the target sequence, and wherein the second region overlaps the first region; and an optical label wherein the oligonucleotide molecule comprises a first end linked to the metal nanoparticle and a second end linked to the optical label, wherein in the absence of the nucleic acid target the placeholder strand binds the placeholder binding sequence and the stem loop is open, and wherein in the presence of the nucleic acid target the placeholder strand binds the target sequence and the stem-L sequence and the stem-R sequence base pair to form the stem loop.

2. The nanoprobe of claim 1, wherein the optical label comprises a Raman label, a positively-charged hydrophobic near infrared (NIR) dye, a fluorescence label, or absorbance label.

3. The nanoprobe of claim 1, wherein the nucleic acid target comprises a DNA or an RNA.

4. The nanoprobe of claim 3, wherein the nucleic acid target comprises an microRNA or mRNA.

5. The nanoprobe of claim 1, wherein the placeholder strand is an siRNA or an anti-microRNA.

6. The nanoprobe of claim 1, wherein the metal nanoparticle comprises silver nanoparticles, gold nanoparticles, silver nanostars, gold nanostars, silver-coated gold nanostars, bimetallic nanoparticles, multi-metallic nanoparticles, dielectric nanoparticle cores covered with metal nanoshells, or multi-nanoparticle structures.

7. The nanoprobe of claim 1, wherein the metal nanoparticle comprises a gold nanostar.

8. The nanoprobe of claim 1, wherein the metal nanoparticle is embedded in a hollow silica shell.

9. The nanoprobe of claim 1, wherein the loop comprises the placeholder binding sequence.

10. The nanoprobe of claim 1, wherein the loop and the stem-R sequence comprise the placeholder binding sequence.

11. The nanoprobe of claim 1, wherein electromagnetic excitation of the nanoprobe yields an optical signal that is higher in the presence of the nucleic acid target as compared to the absence of the nucleic acid target.

12. The nanoprobe of claim 11, wherein the optical signal is detectable by surface enhanced Raman scattering (SERS) or surface enhanced resonance Raman scattering (SERRS).

13. The nanoprobe of claim 1, wherein the optical label comprises a Raman label.

14. The nanoprobe of claim 1, wherein the optical label comprises a positively-charged hydrophobic near infrared (NIR) dye.

15. The nanoprobe of claim 1, wherein the optical label is selected from 3,3'-Diethylthiadicarbocyanine iodide (DTDC), 3,3'-diethylthiatricarbocyanine iodide (DTTC), 1,1',3,3,3',3'-Hexamethylindotricarbocyanine iodide (HITC), CY3 dye, CY3.5 dye, CY5.5 dye, CY7 dye, CY7.5 dye, IR-780, IR-792, IR-797, IR-813, methylene blue hydrate (MB), 4-mercaptobenzoic acid (4-MBA), 5,5'-dithiobis-2-nitrobenzoic acid (DTNB), 4-aminothiophenol (4ATP), fluorescein, fluorescein isothiocyanate (FITC), a thionine dye, a rhodamine-based dye, and crystal violet.

16. The nanoprobe of claim 1, wherein the metal nanoparticle comprises a polymer coating.

17. The nanoprobe of claim 16, wherein the polymer coating comprises PEG or NIPAM.

18. A composition comprising the nanoprobe of claim 1.

19. The composition of claim 18, comprising at least one second nanoprobe for detecting a second nucleic acid target.

20. An inverse molecular sentinel nanoprobe for detecting a nucleic acid target, comprising a metal nanoparticle, an oligonucleotide molecule comprising a sequence that forms a stem loop, wherein the sequence comprises from 5' to 3' a stem-L sequence, a loop, and a stem-R sequence, wherein the stem-L sequence is complementary to the stem-R sequence, wherein the sequence that forms a stem loop or a portion thereof is a placeholder binding sequence, a separate placeholder strand of 20-30 nucleotides in length comprising a first region complementary to a target sequence in the nucleic acid target and a second region complementary to the placeholder binding sequence, wherein the placeholder binding sequence is 8-15 contiguous nucleotides of the target sequence, wherein the first region extends from a 5' end to a 3' end of the placeholder strand, and wherein the second region is shorter than and overlapping the first region; and an optical label wherein the oligonucleotide molecule comprises a first end linked to the metal nanoparticle and a second end linked to the optical label, wherein in the absence of the nucleic acid target the placeholder strand binds the placeholder binding sequence and the stem loop is open, and wherein in the presence of the nucleic acid target the placeholder strand binds the target sequence and the stem-L sequence and the stem-R sequence base pair to form the stem loop.

\* \* \* \* \*